(12) United States Patent
Haley et al.

(10) Patent No.: US 11,021,489 B2
(45) Date of Patent: Jun. 1, 2021

(54) POLYCYCLIC AROMATIC COMPOUND EMBODIMENTS AND METHODS OF MAKING AND USING THE SAME

(71) Applicant: University of Oregon, Eugene, OR (US)

(72) Inventors: Michael Haley, Eugene, OR (US); Justin Dressler, Eugene, OR (US); Joshua Barker, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 16/805,382

(22) Filed: Feb. 28, 2020

(65) Prior Publication Data

US 2020/0277302 A1 Sep. 3, 2020

Related U.S. Application Data

(60) Provisional application No. 62/812,797, filed on Mar. 1, 2019.

(51) Int. Cl.

| | | |
|---|---|---|
| *C07D 495/04* | (2006.01) | |
| *C07D 493/04* | (2006.01) | |
| *C07D 487/04* | (2006.01) | |
| *H01L 51/00* | (2006.01) | |
| *H01L 51/05* | (2006.01) | |
| *H01L 51/42* | (2006.01) | |
| *H01L 51/50* | (2006.01) | |
| *C07D 491/048* | (2006.01) | |

(52) U.S. Cl.
CPC ......... *C07D 495/04* (2013.01); *C07D 487/04* (2013.01); *C07D 493/04* (2013.01); *H01L 51/0072* (2013.01); *H01L 51/0073* (2013.01); *H01L 51/0074* (2013.01); *H01L 51/0094* (2013.01)

(58) Field of Classification Search
CPC .. C07D 495/04; C07D 493/04; C07D 487/04; C07D 491/048; H01L 51/0094; H01L 51/0072; H01L 51/0073; H01L 51/0074; H01L 51/42; H01L 51/50; H01L 51/0558
See application file for complete search history.

(56) References Cited

U.S. PATENT DOCUMENTS

| | | |
|---|---|---|
| 6,506,505 B1 | 1/2003 | Weber et al. |
| 6,690,029 B1 | 2/2004 | Anthony et al. |
| 7,208,567 B2 | 4/2007 | Oguma et al. |
| 7,385,221 B1 | 6/2008 | Anthony et al. |
| 8,921,578 B2 | 12/2014 | Haley et al. |
| 8,927,117 B2 | 1/2015 | Buesing |
| 9,099,660 B2 | 8/2015 | Haley et al. |
| 9,773,988 B2 | 9/2017 | Haley et al. |
| 9,876,182 B2 | 1/2018 | Haley et al. |
| 2008/0220285 A1 | 9/2008 | Vestweber et al. |
| 2009/0149627 A1 | 6/2009 | Pan et al. |
| 2010/0331550 A1 | 12/2010 | Moawia et al. |
| 2013/0096336 A1 | 4/2013 | Haley et al. |
| 2013/0150592 A1 | 6/2013 | Haley et al. |

FOREIGN PATENT DOCUMENTS

| | | |
|---|---|---|
| WO | WO 2010/020329 | 2/2010 |
| WO | WO 2011/159763 | 12/2011 |
| WO | WO 2013/010614 | 1/2013 |

OTHER PUBLICATIONS

Registry No. 2035406-55-2; entered STN Registry Database Nov. 21, 2016 [Database Registry Chemical Abstracts Service, Columbus, Ohio]; 1 p.*
Chan et al., "Synthesis, characterization, and photovoltaic properties of novel semiconducting polymers with thiophene-phenylene-thiophene (TPT) as coplanar units," *Macromolecules*, 41(15): 5519-5526, Jul. 8, 2008.
Chase et al., "Indeno[1,2-b]fluorenes: fully conjugated antiaromatic analogues of acenes," *Angew. Chem. Int. Ed.*, 50(5): 1127-1130, Feb. 1, 2011.
Dressler et al., "Thiophene and its sulfur inhibit indenoindenodibenzothiophene diradicals from low-energy lying thermal triplets," *Nat. Chem.*, No. 10, pp. 1134-1140, Sep. 17, 2018.
Haley "Indenofluorenes—A new Class of Electron-Accepting Materials," Presentation given on Jul. 29, 2013.
Haley et al. "Quinoidal diindenothienoacenes: synthesis and properties of new functional organic materials," *Chem. Sci.* 2014, 5, 3627-3633, Jun. 16, 2014.
International Search Report and Written Opinion issued for International Application No. PCT/US2011/040451 dated Oct. 14, 2011.
International Search Report and Written Opinion issued for International Application No. PCT/US2014/048262 dated Nov. 14, 2014.
Miyawaki et al., "Multiple cycloaromatization of novel aromatic enediynes bearing a triggering device on the terminal acetylene carbon," *Tetrahedron Letters*, 39(38): 6923-6926, Sep. 17, 1998.
Padwa et al., "A comparative study of the decomposition of o-alkynyl-substituted aryl diazo ketones. Synthesis of polyunsubstituted β-naphthols via arylketene intermediates," *J. Org. Chem.*, 58(23): 6429-6437, Nov. 1, 1993.
Payne et al., "Stable crystalline acenedithiophenes with up to seven linearly fused rings," *Org. Lett.*, 6(19): 3325-3328, Aug. 24, 2004.
Shi et al. "Antiaromatic bisindeno-[n]thienoacenes with small singlet biradical characters: syntheses, structures and chain length dependent physical properties," *Chem. Sci.* 2014, 5, 4490-4503, Jul. 11, 2014.

(Continued)

*Primary Examiner* — John M Mauro
(74) *Attorney, Agent, or Firm* — Klarquist Sparkman, LLP

(57) ABSTRACT

Disclosed herein are polycyclic aromatic compound embodiments and methods of making and using such compounds. In some embodiments, the polycyclic aromatic compounds comprise an indenoindenodi(benzothiophene) skeleton. The polycyclic aromatic compound embodiments can be used in a variety of devices, such as electronic and/or electrooptical devices.

20 Claims, 15 Drawing Sheets

(56) References Cited

OTHER PUBLICATIONS

Zhang et al., "Indacenodithiophene semiconducting polymers for high-performance, air-stable transistors," *JACS*, 132(33): 11437-11439, Aug. 2, 2010.

* cited by examiner

Skeleton of 310

Skeleton of 7,14-dimesitylfluoreno[3,2-b]fluorene

Skeleton of 308a 7,14-dimesitylfluoreno[3,2-b]fluorene

POLYCYCLIC AROMATIC COMPOUND EMBODIMENTS AND METHODS OF MAKING AND USING THE SAME

CROSS REFERENCE TO RELATED APPLICATION

This application claims the benefit of the earlier filing date of U.S. Provisional Patent Application No. 62/812,797, filed on Mar. 1, 2019, the entirety of which is incorporated herein by reference.

ACKNOWLEDGMENT OF GOVERNMENT SUPPORT

This invention was made with government support under grant No. NSF CHE-1565780 awarded by the National Science Foundation. The government has certain rights in the invention.

FIELD

Disclosed herein are polycyclic aromatic compound embodiments and methods of making and using the same.

BACKGROUND

Polyaromatic hydrocarbon compounds, such as pentacene, are a class of compounds that have been explored as conducting organic materials for use in device applications, such as organic light-emitting diodes (OLEDs), field-effect transistors (OFETs), and solar cells. However, such materials are difficult to make and pentacene, in particular, readily oxidizes to its respective quinone in aerobic conditions and reacts with itself to afford a butterfly dimer. The driving force for both reactions is the formation of two aromatic naphthalene units, which ultimately disrupts overall conjugation and thus leads to poor device performance. While degradation can be slowed in such compounds, these processes are not completely suppressed. As such, efficient electron transfer can be disrupted. There exists a need in the art for different organic compounds that can be used in various electronic and electrooptical devices.

SUMMARY

Disclosed herein are embodiments of a polycyclic aromatic compound and methods of making and using the same. The compound embodiments are described herein. Also disclosed herein are embodiments of an apparatus, comprising an electronic or electrooptical device selected from an organic light-emitting diode (OLED), an organic field-effect transistor (OFET), or an organic photovoltaic cell (OPV) and further comprising a compound (or compounds) as described herein. Also disclosed are embodiments of thin films comprising the compounds. Methods for making various compound embodiments of the present disclosure also are described.

The foregoing and other objects and features of the present disclosure will become more apparent from the following detailed description, which proceeds with reference to the accompanying figures.

BRIEF DESCRIPTION OF THE DRAWINGS

FIG. 1 is a UV-vis spectrum for compound 406a.

FIG. 7 depicts two canonical open-shell resonance forms between the thiophene groups for compound 308a.

FIG. 11 shows data obtained from using variable temperature $^1$H NMR to analyze compound 406a.

FIG. 13 is a thermogravimetric analysis plot for compound 308a.

FIG. 15 is a thermogravimetric analysis plot for compound 406a.

DETAILED DESCRIPTION

I. Overview of Terms

Figure 1:
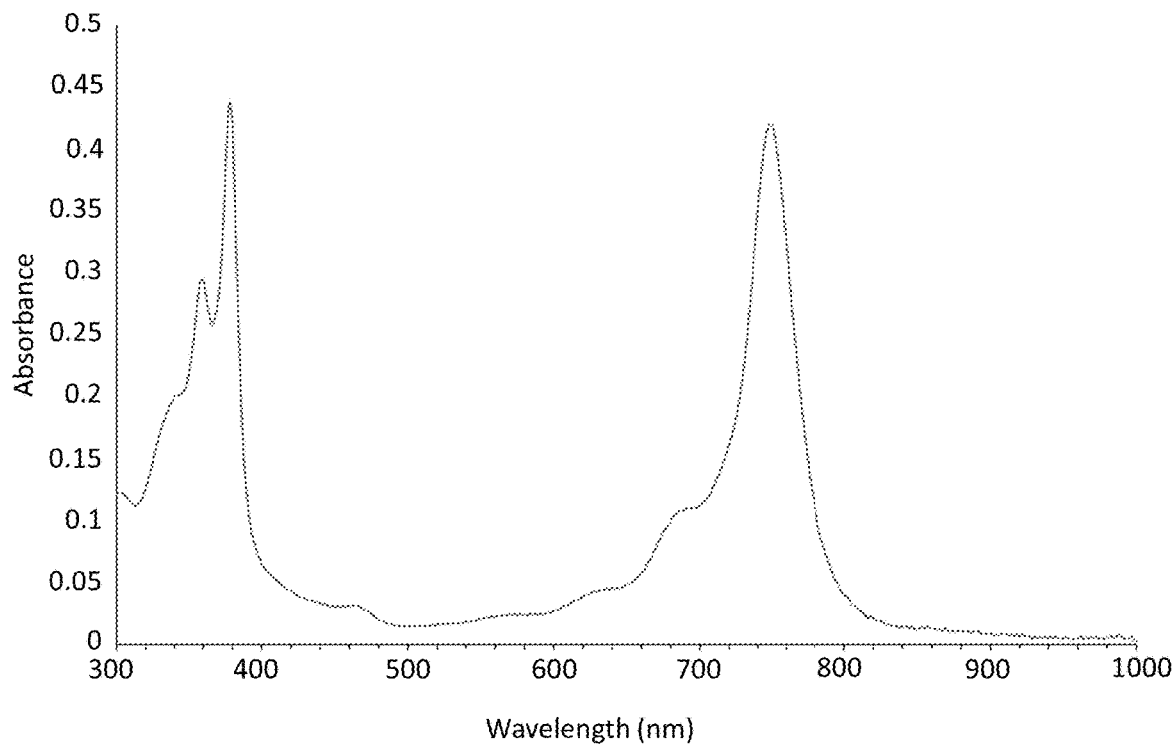

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the compound to which it is bound. Also, a dashed bond (i.e., "—") as used in certain formulas described herein indicates an optional bond (that is, a bond that may or may not be present). A person of ordinary skill in the art would recognize that the definitions provided below and the compounds and formulas included herein are not intended to include impermissible substitution patterns (e.g., methyl substituted with 5 different groups, and the like). Such impermissible substitution patterns are easily recognized by a person of ordinary skill in the art. When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

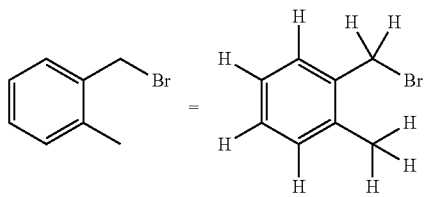

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aromatic: An aromatic group that is or can be coupled to a compound disclosed herein, wherein the aromatic group is or becomes coupled through an aliphatic group.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_{2-50}$, such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, such as —O-alkyl, —O-alkenyl, —O-alkynyl; with exemplary embodiments including, but not limited to, methoxy, ethoxy, n-propoxy, isopropoxy, n-butoxy, t-butoxy, sec-butoxy, n-pentoxy (wherein any of the aliphatic components of such groups can comprise no double or triple bonds, or can comprise one or more double and/or triple bonds).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or —NR$^a$C(O)R$^b$ wherein each of R$^a$ and R$^b$ independently is selected from hydrogen, aliphatic, heteroaliphatic, haloaliphatic, haloheteroaliphatic, aromatic, or an organic functional group.

Amino: —NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

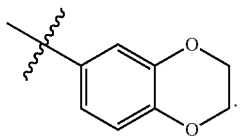 [SMILES: *c1ccc2c(c1)OCCO2]

However, in certain examples, context or express disclosure may indicate that the point of attachment is through a non-aromatic portion of the condensed ring system. For example,

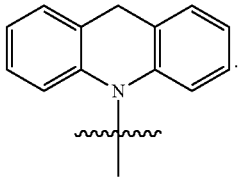 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, haloaliphatic, haloheteroaliphatic, aromatic, or an organic functional group.

Aroxy: —O-aromatic.

Azo: —N=NR$^a$ wherein R$^a$ is hydrogen, aliphatic, heteroaliphatic, haloaliphatic, haloheteroaliphatic, aromatic, or an organic functional group Carbamate: —OC(O)NR$^a$R$^b$, wherein each of R$^a$ and R$^b$ independently is selected from hydrogen, aliphatic, heteroaliphatic, haloaliphatic, haloheteroaliphatic, aromatic, or an organic functional group Carboxyl: —C(O)OH.

Carboxylate: —C(O)O$^-$ or salts thereof, wherein the negative charge of the carboxylate group may be balanced with an M$^+$ counter ion, wherein M$^+$ may be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as [Ca$^{2+}$]$_{0.5}$, [Mg$^{2+}$]$_{0.5}$, or [Ba$^{2+}$]$_{0.5}$.

Cyano: —CN.

Disulfide: —SSR$^a$, wherein R$^a$ is selected from hydrogen, aliphatic, heteroaliphatic, haloaliphatic, haloheteroaliphatic, aromatic, or an organic functional group.

Dithiocarboxylic acid: —C(S)SR$^a$ wherein R$^a$ is selected from hydrogen, aliphatic, heteroaliphatic, haloaliphatic, haloheteroaliphatic, aromatic, or an organic functional group.

Ester: —C(O)OR$^a$ or —OC(O)R$^a$, wherein R$^a$ is selected from aliphatic, heteroaliphatic, haloaliphatic, haloheteroaliphatic, aromatic, or an organic functional group.

Halo (or halide or halogen): Fluoro, chloro, bromo, or iodo.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a CX$_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino, disulfide, peroxy, and thioether groups are exemplary (but non-limiting) examples of heteroaliphatic.

Heteroaliphatic-aryl: An aryl group that is or can be coupled to a compound disclosed herein, wherein the aryl group is or becomes coupled through a heteroaliphatic group.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, haloaliphatic, haloheteroaliphatic, aromatic, or an organic functional group. In some embodiments, a fluorophore can also be described herein as a heteroaryl group.

Heteroatom: An atom other than carbon or hydrogen, such as (but not limited to) oxygen, nitrogen, sulfur, silicon, boron, selenium, or phosphorous. In particular disclosed embodiments, such as when valency constraints do not permit, a heteroatom does not include a halogen atom.

Ketone: —C(O)$R^a$, wherein $R^a$ is selected from aliphatic, heteroaliphatic, haloaliphatic, haloheteroaliphatic, aromatic, or an organic functional group.

Lower Aliphatic: An aliphatic group having 1 to 10 carbon atoms, such as 1 to 8 carbon atoms, or 1 to 6 carbon atoms, or 1 to 4 carbon atoms. In some embodiments, lower aliphatic includes lower alkyl groups, such as methyl, ethyl, propyl, isopropyl, butyl, and isobutyl, tert-butyl.

Organic Functional Group: A functional group that may be provided by any combination of an aliphatic, heteroaliphatic, aromatic, haloaliphatic, and/or haloheteroaliphatic, or that may be selected from, but not limited to, aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

Oxime: —C$R^a$=NOH, wherein $R^a$ is hydrogen, aliphatic, heteroaliphatic, haloaliphatic, haloheteroaliphatic, aromatic, or an organic functional group.

Peroxy: —O—O$R^a$ wherein $R^a$ is hydrogen, aliphatic, heteroaliphatic, haloaliphatic, haloheteroaliphatic, aromatic, or an organic functional group.

Phosphate: —O—P(O)(O$R^a$)$_2$, wherein each $R^a$ independently is hydrogen, aliphatic, heteroaliphatic, haloaliphatic, haloheteroaliphatic, aromatic, or an organic functional group; or wherein one or more $R^a$ groups are not present and the phosphate group therefore has at least one negative charge, which can be balanced by a counterion, $M^+$, wherein each $M^+$ independently can be an alkali ion, such as $K^+$, $Na^+$, $Li^+$; an ammonium ion, $^+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Phosphonate: —P(O)(O$R^a$)$_2$, wherein each $R^a$ independently is hydrogen, aliphatic, heteroaliphatic, haloaliphatic, haloheteroaliphatic, aromatic, or an organic functional group; or wherein one or more $R^a$ groups are not present and the phosphate group therefore has at least one negative charge, which can be balanced by a counterion, $M^+$, wherein each $M^+$ independently can be an alkali ion, such as $K^+$, $Na^+$, $Li^+$; an ammonium ion, such as $^+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Silyl Ether: —OSi$R^aR^b$, wherein each of $R^a$ and $R^b$ independently is selected from hydrogen, aliphatic, heteroaliphatic, haloaliphatic, haloheteroaliphatic, aromatic, or an organic functional group.

Sulfinyl: —S(O)$R^a$, wherein $R^a$ is selected from hydrogen, aliphatic, heteroaliphatic, haloaliphatic, haloheteroaliphatic, aromatic, or an organic functional group.

Sulfonyl: —SO$_2R^a$, wherein $R^a$ is selected from hydrogen, aliphatic, heteroaliphatic, haloaliphatic, haloheteroaliphatic, aromatic, or an organic functional group.

Sulfonamide: —SO$_2$N$R^aR^b$ or —N($R^a$)SO$_2R^b$, wherein each of $R^a$ and $R^b$ independently is selected from hydrogen, aliphatic, heteroaliphatic, haloaliphatic, haloheteroaliphatic, aromatic, or an organic functional group.

Sulfonate: —SO$_3^-$, wherein the negative charge of the sulfonate group may be balanced with an $M^+$ counter ion, wherein $M^+$ may be an alkali ion, such as $K^+$, $Na^+$, $Li^+$; an ammonium ion, such as $^+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Thial: —C(S)H.

Thiocarboxylic acid: —C(O)SH, or —C(S)OH.

Thiocyanate: —S—CN or —N=C=S.

Thioester: —C(O)S$R^a$ or —C(S)O$R^a$ wherein $R^a$ is selected from hydrogen, aliphatic, heteroaliphatic, haloaliphatic, haloheteroaliphatic, aromatic, or an organic functional group.

Thioether: —S-aliphatic or —S-aromatic, such as —S-alkyl, —S-alkenyl, —S-alkynyl, —S-aryl, or —S-heteroaryl; or -aliphatic-S-aliphatic, -aliphatic-S-aromatic, -aromatic-S-aliphatic, or -aromatic-S-aromatic.

Thioketone: —C(S)$R^a$ wherein $R^a$ is selected from hydrogen, aliphatic, heteroaliphatic, haloaliphatic, haloheteroaliphatic, aromatic, or an organic functional group.

II. Introduction

Diradical polycyclic aromatic hydrocarbons (PAHs) have attracted considerable attention in recent years because of possible uses as organic electronic materials. Diradicaloids often display narrow HOMO-LUMO energy gaps, low-energy electronic absorptions due to a low-lying doubly-excited electronic configuration, redox amphoterism and multicenter bonding, and electron spin resonance (ESR) signal(s) and peak broadening in the proton NMR spectrum. These unique electronic and magnetic characteristics have sparked interest in potential applications such as molecular electronics and spintronics, lithium ion batteries, nonlinear optics and singlet fission materials; however, the diradical nature of compounds exhibiting such characteristics very often imparts high reactivity that can present a significant challenge in their synthesis. Open-shell PAHs known to-date, such as super-heptazethrene and diindenoanthracene, exhibit a thermally accessible triplet state. And, while there are molecules that show radical reactivity and/or large Δ ES-T gap, they typically exhibit low y index values and/or low-energy UV-vis absorptions but with distinct quinoidal bond lengths in X-ray analysis. Such compounds thus are not persistent singlet diradicaloids (which are compounds that do not exhibit a thermally accessible triplet state yet still display pronounced diradical character).

Disclosed herein are compound embodiments that are persistent singlet diradicaloids and that have structural features that facilitate the compounds' ability to exhibit strong diradical character and unusually large singlet-triplet energy gaps. The compounds are stable under oxidative conditions and can be readily synthesized using scalable methods.

III. Compound Embodiments

Disclosed herein are embodiments of polycyclic aromatic compounds. In particular embodiments, the compounds have structures satisfying Formula I or Formula II. Compounds of Formula I are referred to as "syn" compound embodiments and have a backbone wherein $X^1$ and $R^3$ are attached to adjacent carbon atoms (and $X^2$ and $R^4$ are attached to adjacent carbon atoms). Compounds of Formula II are referred to as "anti" compound embodiments and have a backbone wherein $X^1$ and $R^3$ are attached to carbon atoms that are separated by one intervening carbon atom (and $X^2$ and $R^4$ are attached to carbon atoms that are separated by one intervening carbon atom).

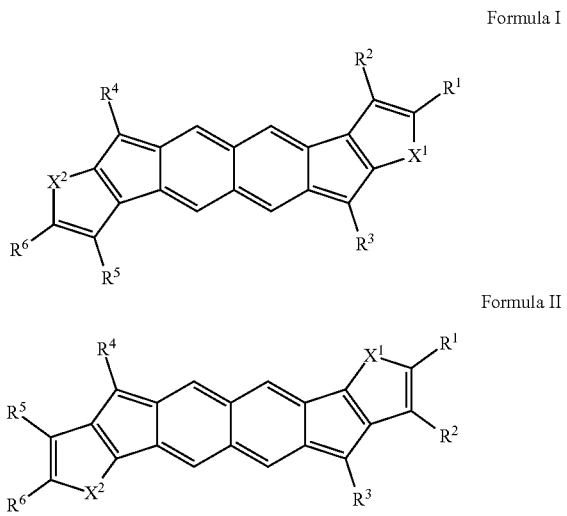

Formula I

Formula II

With reference to Formulas I and II, the following definitions can apply:

each of $X^1$ and $X^2$ independently are selected from S (and oxidized forms thereof, such as $SO_2$, SO, or the like), O, or NR, wherein each R independently is selected from hydrogen, aliphatic, heteroaliphatic, haloaliphatic, haloheteroaliphatic, aromatic, or an organic functional group;

each of $R^3$ and $R^4$ independently is selected from hydrogen, aliphatic, aromatic, heteroaliphatic, or an organic functional group;

each of $R^1$, $R^2$, $R^5$, and $R^6$ independently is selected from hydrogen, aliphatic, aromatic, heteroaliphatic, or an organic functional group; or $R^1$ and $R^2$ together, and/or $R^5$ and $R^6$ together, provide an aromatic ring.

In some embodiments, the following variable definitions can apply for Formulas I and II:

each of $X^1$ and $X^2$ independently are selected from S, O, SO, $SO_2$, NR, wherein each R independently is selected from hydrogen, alkyl, alkynyl, or alkenyl, heteroalkyl, heteroalkynyl, or heteroalkenyl, aryl, or heteroaryl;

each of $R^3$ and $R^4$ independently is selected from hydrogen; alkyl; alkynyl; alkenyl; heteroalkyl; heteroalkynyl; heteroalkenyl; benzyl; phenyl; naphthyl; pyridinyl; halogen, such as Br, F, I, Cl; nitro; cyano; thiol; or hydroxyl; and each of $R^1$, $R^2$, $R^5$, and $R^6$ independently is selected from hydrogen; alkyl; alkynyl; alkenyl; heteroalkyl; heteroalkynyl; heteroalkenyl; benzyl; phenyl; naphthyl; pyridinyl; halogen, such as Br, F, I, Cl; nitro; cyano; thiol; or hydroxyl; or $R^1$ and $R^2$ together, and/or $R^5$ and $R^6$ together, provide an aryl or heteroaryl ring.

In some embodiments, the following variable definitions can apply for Formulas I and II:

each of $X^1$ and $X^2$ independently are selected from S, O, $SO_2$, NR, wherein each R independently is selected from H, lower alkyl (e.g., methyl, ethyl, propyl, butyl, pentyl, and isomers thereof), lower alkenyl (e.g., a methyl, ethyl, propyl, butyl, or pentyl group comprising one or more double bonds), lower alkynyl (e.g., a methyl, ethyl, propyl, butyl, or pentyl group comprising one or more triple bonds), phenyl, naphthyl, or pyridinyl;

each of $R^3$ and $R^4$ independently is selected from hydrogen; lower alkyl (e.g., methyl, ethyl, propyl, butyl, pentyl, and isomers thereof); lower alkenyl (e.g., a methyl, ethyl, propyl, butyl, or pentyl group comprising one or more double bonds); lower alkynyl (e.g., a methyl, ethyl, propyl, butyl, or pentyl group comprising one or more triple bonds); alkoxy, such as lower alkoxy (e.g., —$OCH_3$, —$OCH_2CH_3$, —$OCH_2CH_2CH_3$, —$OCH_2CH_2CH_2CH_3$, —$OCH_2CH_2CH_2CH_2CH_3$, and the like); amino (such as —$NR^aR^b$, wherein $R^a$ is aliphatic, heteroaliphatic, haloaliphatic, haloheteroaliphatic, aromatic, or an organic functional group and $R^b$ is hydrogen, aliphatic, heteroaliphatic, haloaliphatic, haloheteroaliphatic, aromatic, or an organic functional group; or —$NR^aR^b$, wherein $R^a$ and $R^b$ are hydrogen); ether; peroxy; aroxy; disulfide; silyl ether; Br; F; I; Cl; phenyl (e.g., 2,4,6-$Me_3C_6H_2$, 2,4,6-$iPr_3C_6H_2$, 4-t-$Bu_3C_6H_4$, and 4-t-Bu-2,6-$Me_2CH_6H_2$); pyridinyl; furanyl; pyrroyl; nitro; cyano; thiol; thioether, such as lower thioether (e.g., —$SCH_3$, —$SCH_2CH_3$, —$SCH_2CH_2CH_3$, —$SCH_2CH_2CH_2CH_3$, —$SCH_2CH_2CH_2CH_2CH_3$, and the like); or hydroxyl;

$R^1$ and $R^2$ together provide a phenyl group, a naphthyl group, an anthracenyl group, a tetracenyl group, a pentacenyl group, a phenanthrenyl group, a chrysenyl group, a pyrenyl group, or other aromatic ring system; and $R^5$ and $R^6$ together provide a phenyl group, a naphthyl group, an anthracenyl group, a tetracenyl group, a pentacenyl group, a phenanthrenyl group, a chrysenyl group, a pyrenyl group, or other aromatic ring system.

In any of the above embodiments, if any one or more of $R^1$, $R^2$, $R^3$, $R^4$, $R^5$, or $R^6$ are aromatic groups, such as aryl or heteroaryl groups, the aromatic group can further comprise one or more substituents. In some embodiments, substituents that can be included with an aromatic group include, but are not limited to, aliphatic groups, heteroaliphatic groups, aromatic groups, haloaliphatic groups, or organic functional groups. In some embodiments, the substituents can be organic functional groups including, but not limited to, halogen atoms, nitro groups, cyano groups, ester groups, azide groups, acyl halide groups, aldehyde groups, carboxyl (or carboxylate) groups, amide groups, ketone groups, carbonate groups, imine groups, azo groups, carbamate groups, hydroxyl groups, thiol groups, sulfoxide groups, sulfone groups, sulfonamide groups, sulfonyl (or sulfonate) groups, oxime groups, carbamate ester groups, thiocyanate groups, thioketone groups, thiocarboxylic acid groups, thioester groups, a thial group, dithiocarboxylic groups, a phosphate, phosphonate groups, or combinations thereof.

In some embodiments, the compound can have a structure satisfying Formula III or IV, illustrated below.

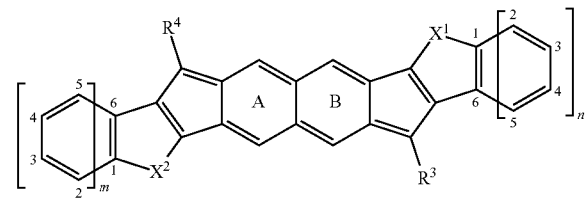

Formula III

Formula IV

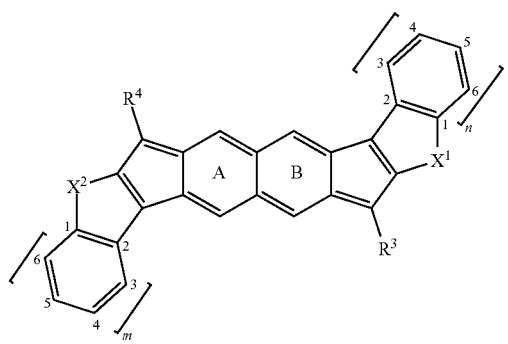

With reference to Formulas III and IV, each of $X^1$, $X^2$, $R^3$, and $R^4$ can be as recited above for Formulas I or II and each of n and m independently can be an integer ranging from 1 to 5, such as 1 to 4, or 1 to 3, or 1 to 2, or 1, 2, 3, 4, or 5. In some embodiments of Formulas III and IV, each of $X^1$ and $X^2$ independently are selected from S, O, SO, $SO_2$, NR, wherein each R independently is selected from hydrogen, aliphatic, heteroaliphatic, haloaliphatic, haloheteroaliphatic, aromatic, or an organic functional group; each of $R^3$ and $R^4$ independently is selected from hydrogen, aliphatic, aromatic, heteroaliphatic, or an organic functional group; and each of n and m independently can be an integer selected from 1 to 3, such as 1, 2, or 3.

In some embodiments, each of $X^1$ and $X^2$ independently are selected from S, O, $SO_2$, NR, wherein each R independently is selected from H, alkyl, alkynyl, alkenyl, heteroalkyl, heteroalkynyl, heteroalkenyl, aryl, or heteroaryl; each of $R^3$ and $R^4$ independently is selected from hydrogen; alkyl; alkynyl; alkenyl; heteroalkyl; heteroalkynyl; heteroalkenyl; benzyl; phenyl; naphthyl; pyridinyl; halogen, such as Br, F, I, Cl; nitro; cyano; thiol; or hydroxyl; n is an integer ranging from 1 to 3, such as 1, 2, or 3; and m is an integer ranging from 1 to 3, such as 1, 2, or 3.

In some embodiments, each of $X^1$ and $X^2$ independently are selected from S, O, $SO_2$, NR, wherein each R independently is selected from H, lower alkyl (e.g., methyl, ethyl, propyl, butyl, pentyl, and isomers thereof), lower alkenyl (e.g., a methyl, ethyl, propyl, butyl, or pentyl group comprising one or more double bonds), lower alkynyl (e.g., a methyl, ethyl, propyl, butyl, or pentyl group comprising one or more triple bonds), phenyl, naphthyl, or pyridinyl; each of $R^3$ and $R^4$ independently is selected from hydrogen; lower alkyl (e.g., methyl, ethyl, propyl, butyl, pentyl, and isomers thereof); lower alkenyl (e.g., a methyl, ethyl, propyl, butyl, or pentyl group comprising one or more double bonds); lower alkynyl (e.g., a methyl, ethyl, propyl, butyl, or pentyl group comprising one or more triple bonds); alkoxy, such as lower alkoxy (e.g., $-OCH_3$, $-OCH_2CH_3$, $-OCH_2CH_2CH_3$, $-OCH_2CH_2CH_2CH_3$, $-OCH_2CH_2CH_2CH_2CH_3$, and the like); amino (such as $-NR^aR^b$, wherein $R^a$ is aliphatic, heteroaliphatic, haloaliphatic, haloheteroaliphatic, aromatic, or an organic functional group and $R^b$ is hydrogen, aliphatic, heteroaliphatic, haloaliphatic, haloheteroaliphatic, aromatic, or an organic functional group; or $-NR^aR^b$, wherein $R^a$ and $R^b$ are hydrogen); ether; peroxy; aroxy; silyl ether; disulfide; Br; F; I; Cl; phenyl (e.g., 2,4,6-$Me_3C_6H_2$, 2,4,6-$iPr_3C_6H_2$, 4-t-$Bu_3C_6H_4$, and 4-t-Bu-2,6-$Me2CH_6H_2$); pyridinyl; furanyl; pyrroyl; nitro; cyano; thiol; thioether, such as lower thioether (e.g., $-SCH_3$, $-SCH_2CH_3$, $-SCH_2CH_2CH_3$, $-SCH_2CH_2CH_2CH_3$, $-SCH_2CH_2CH_2CH_2CH_3$, and the like); or hydroxyl; n is an integer ranging from 1 to 3, such as 1, 2, or 3; and m is an integer ranging from 1 to 3, such as 1, 2, or 4.

As discussed above for Formulas I and II, some embodiments of the compounds can comprise one or more substituents on the 6-membered rings illustrated in Formulas III and IV (excluding rings A and B). Such substituents can be as described above for Formulas I and II and can be located on any one or more of the carbon atoms labeled 2, 3, 4, or 5 for each ring that is present. In embodiments where one or more substituents are present, the compound can have a structure further satisfying Formula IIIA or Formula IVA, illustrated below.

Formula IIIA

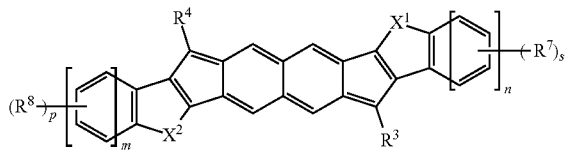

Formula IVA

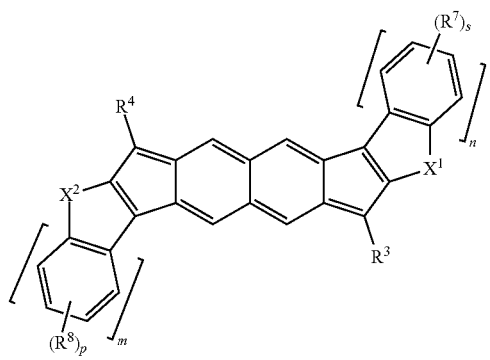

With reference to Formulas IIIA and IVA, each $R^7$ independently can be selected from an aliphatic group (e.g., alkyl, alkenyl, or alkynyl groups), heteroaliphatic group (e.g., alkoxy, amino, ether, peroxy, thioether, or disulfide groups), an aromatic group, haloaliphatic group, or organic functional groups. In some embodiments, the substituents can be organic functional groups including, but not limited to, halogen atoms, nitro groups, cyano groups, ester groups, azide groups, acyl halide groups, aldehyde groups, carboxyl (or carboxylate) groups, amide groups, ketone groups, carbonate groups, imine groups, azo groups, carbamate groups, hydroxyl groups, thiol groups, sulfoxide groups, sulfone groups, sulfonamide groups, sulfonyl (or sulfonate) groups, oxime groups, carbamate ester groups, thiocyanate groups, thioketone groups, thiocarboxylic acid groups, thioester groups, a thial group, dithiocarboxylic groups, a phosphate, phosphonate groups, or combinations thereof; each $R^8$ independently can be selected from aliphatic groups (e.g., alkyl, alkenyl, or alkynyl groups), heteroaliphatic groups (e.g., alkoxy, amino, ether, peroxy, thioether, or disulfide groups), aromatic groups, haloaliphatic groups, or organic functional groups. In some embodiments, the substituents can be organic functional groups including, but not limited to, halogen atoms, nitro groups, cyano groups, ester groups, azide groups, acyl halide groups, aldehyde groups, carboxyl (or carboxylate) groups, amide groups, ketone groups, carbonate groups, imine groups, azo groups, carbamate groups, hydroxyl groups, thiol groups, sulfoxide groups, sulfone groups, sulfonamide groups, sulfonyl (or sulfonate) groups, oxime groups, carbamate ester groups, thiocyanate groups, thioketone groups, thiocarboxylic acid groups, thioester groups, a thial group, dithiocarboxylic groups, a phosphate, phosphonate groups, or combinations thereof; and each of p and s independently can be an integer ranging from 1 to 12, such as 1 to 10, or 1 to 8, or 1 to 6, or 1 to 4, or 1, 2, 3, 4, 5, 6, 7, 8, 9, 10, 11, or 12.

Representative compound embodiments are illustrated in Table 1 below.

TABLE 1

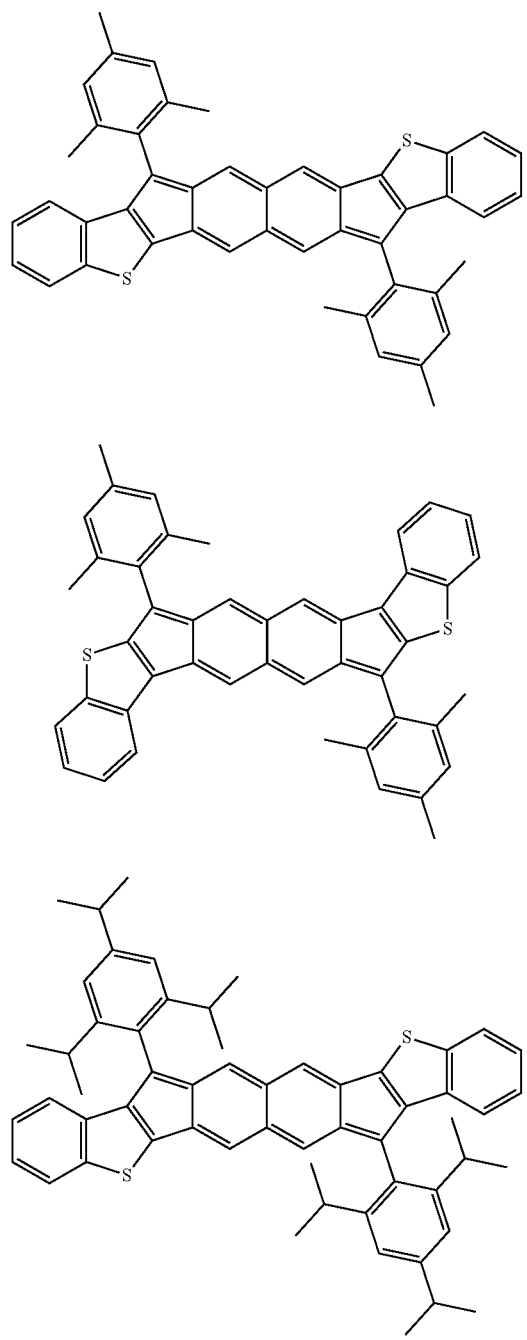

TABLE 1-continued

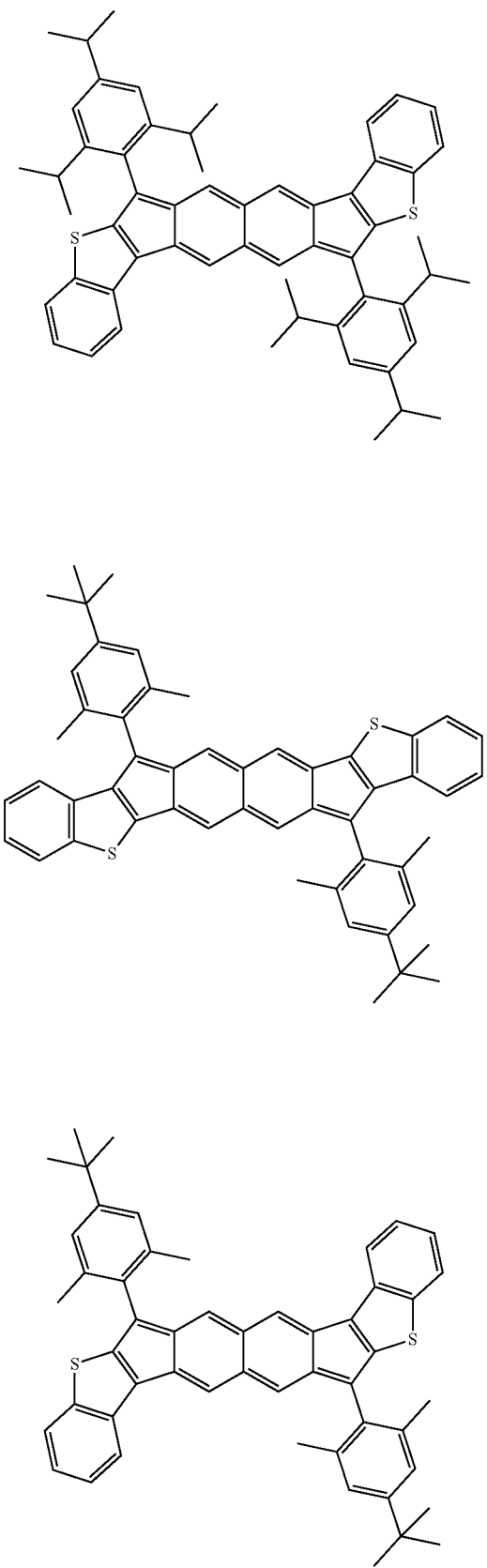

TABLE 1-continued
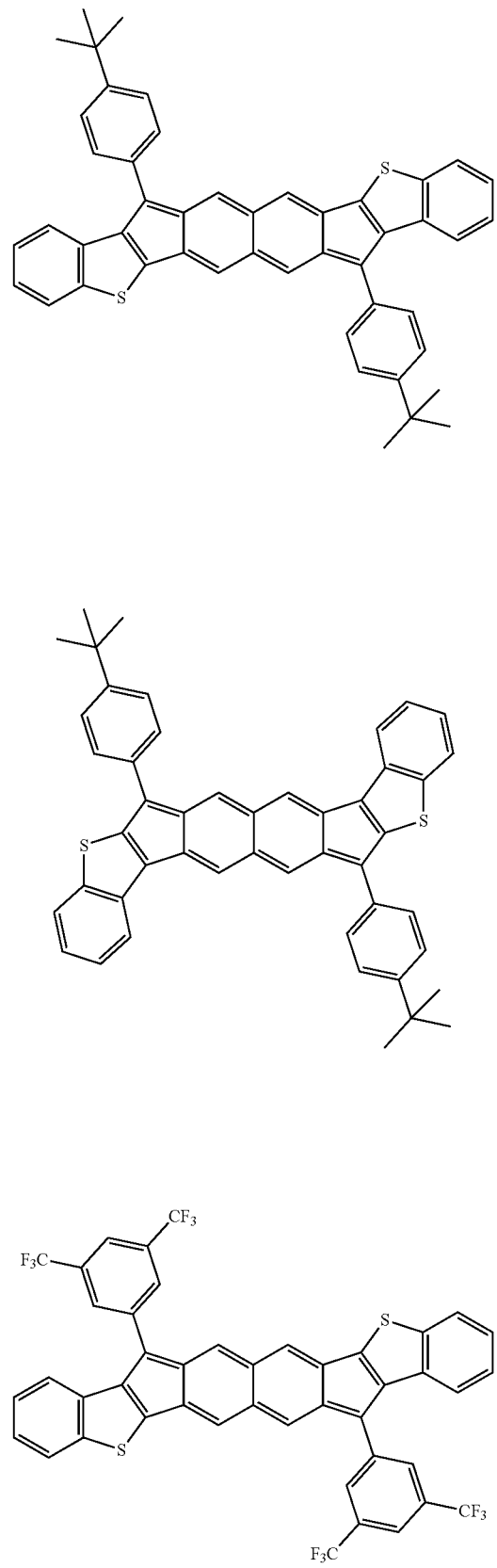
TABLE 1-continued
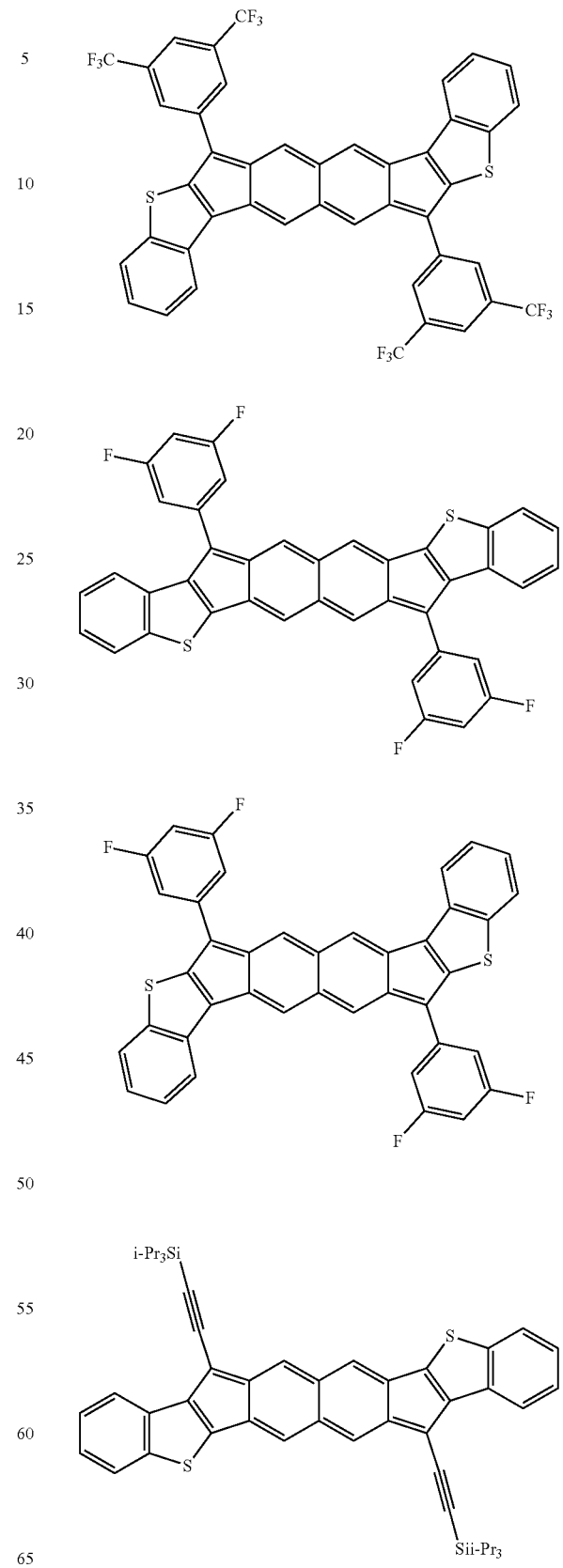

TABLE 1-continued
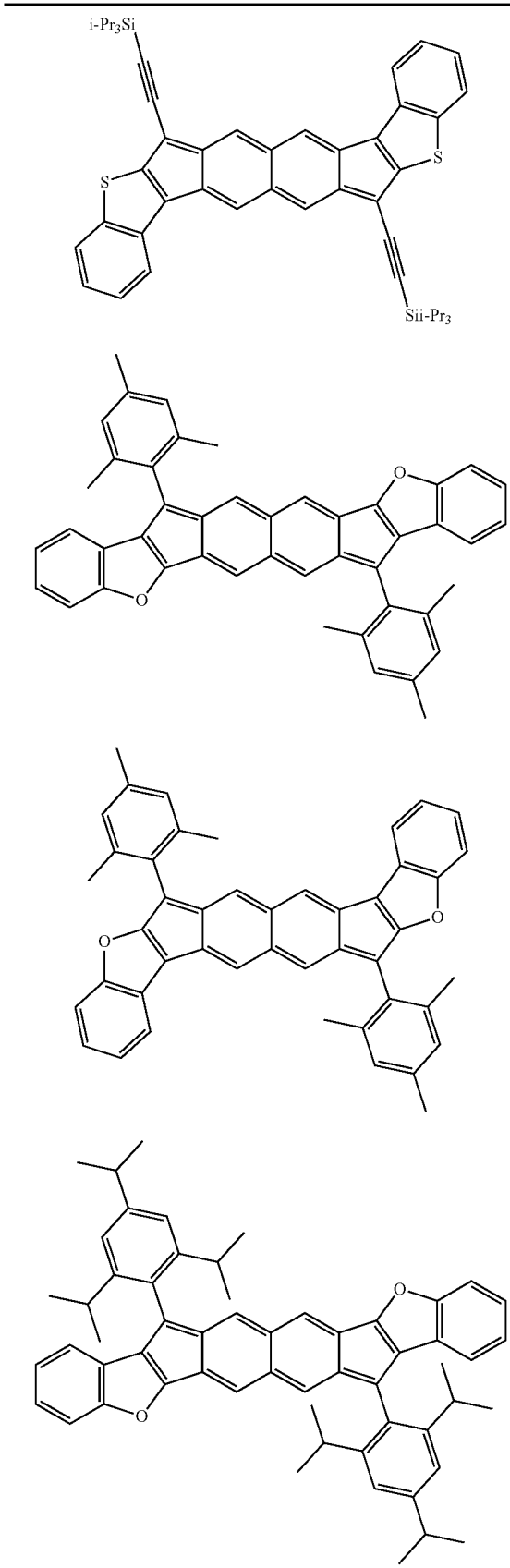
TABLE 1-continued
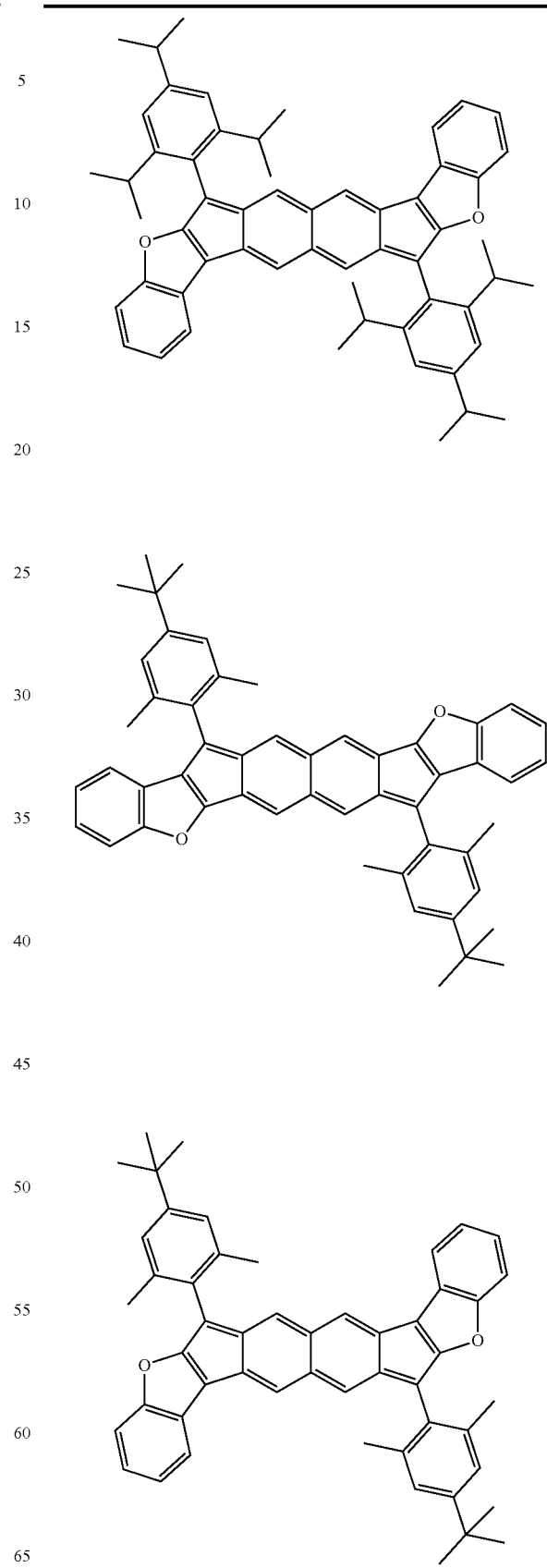

TABLE 1-continued
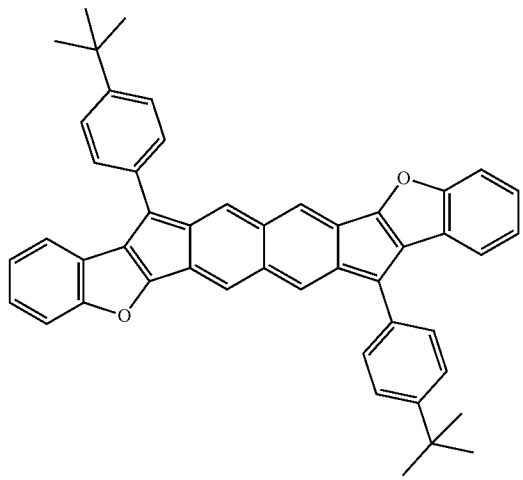
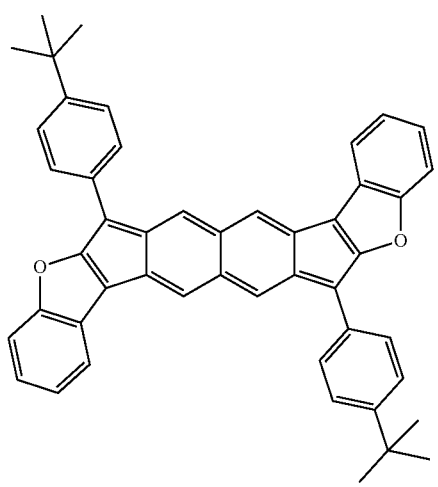
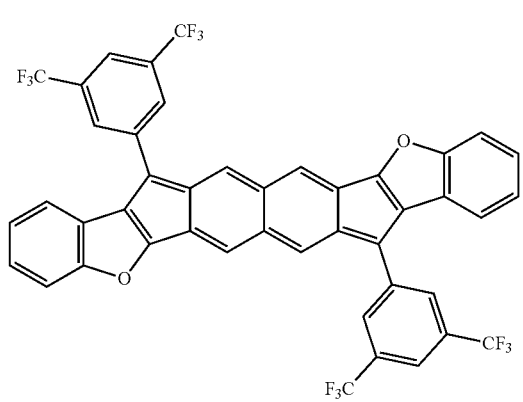 [SMILES: FC(F)(F)c1cc(C2=c3cc4cc5c(cc4cc3-c3sc4ccccc4c32)=C(c2cc(C(F)(F)F)cc(C(F)(F)F)c2)c2c-5sc3ccccc23)cc(C(F)(F)F)c1]
TABLE 1-continued
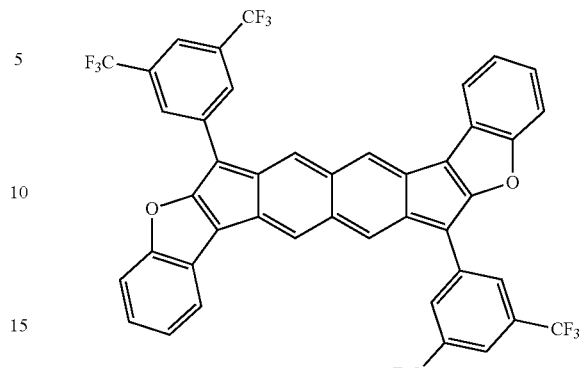
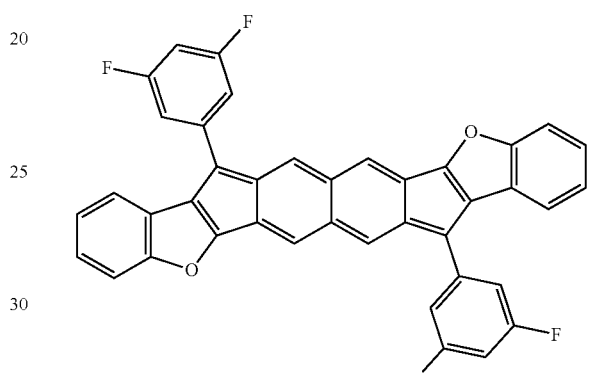
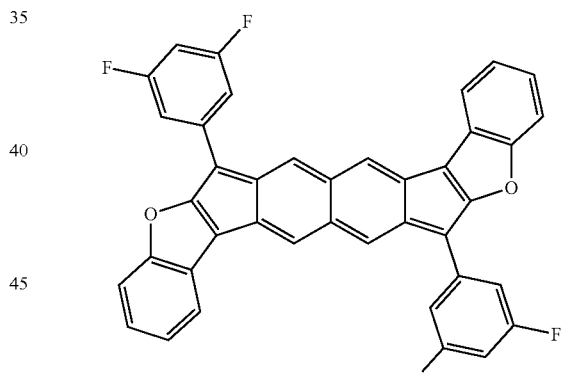
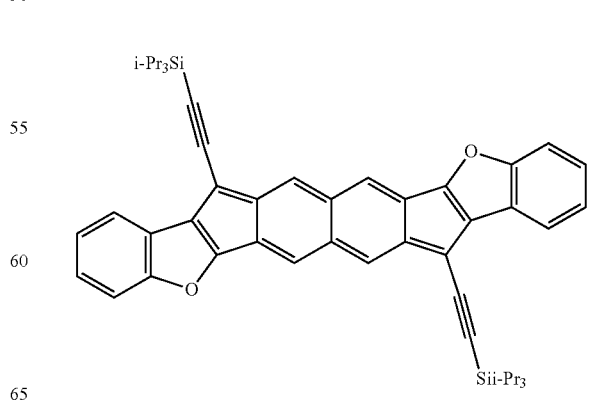

TABLE 1-continued
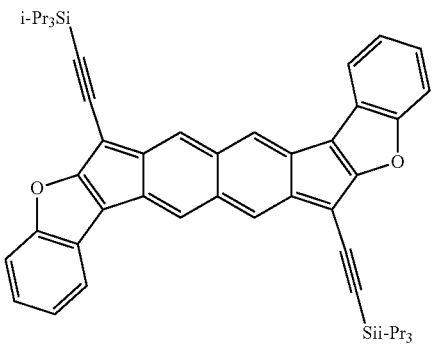
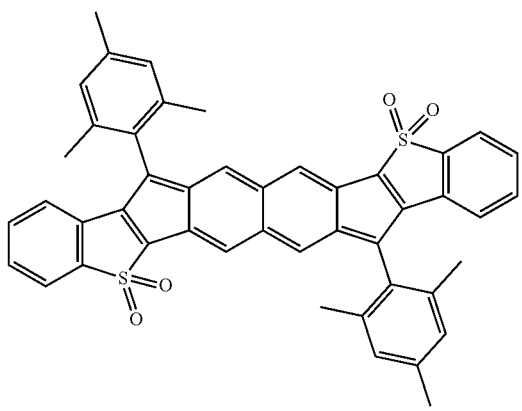 [SMILES: Cc1cc(C)c(C2=c3cc4cc5c(cc4cc3C3=C2c2ccccc2S3(=O)=O)=C(c2c(C)cc(C)cc2C)C2=C5S(=O)(=O)c3ccccc32)c(C)c1]
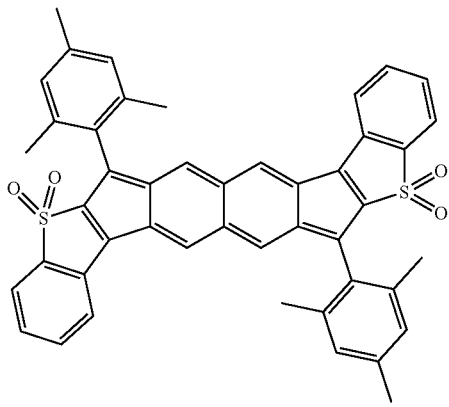 [SMILES: Cc1cc(C)c(C2=c3cc4cc5c(cc4cc3C3=C2S(=O)(=O)c2ccccc23)=C(c2c(C)cc(C)cc2C)C2=C5c3ccccc3S2(=O)=O)c(C)c1]
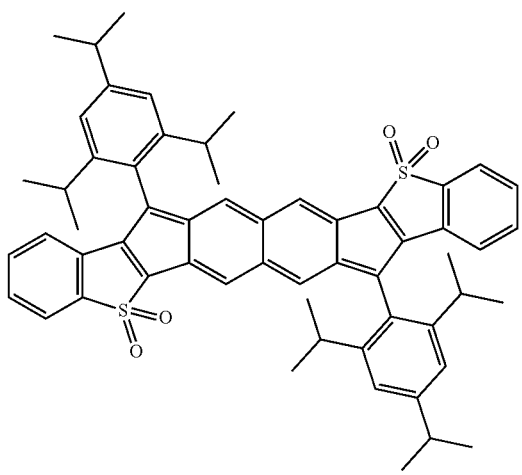 [SMILES: CC(C)c1cc(C(C)C)c(C2=c3cc4cc5c(cc4cc3C3=C2c2ccccc2S3(=O)=O)=C(c2c(C(C)C)cc(C(C)C)cc2C(C)C)C2=C5S(=O)(=O)c3ccccc32)c(C(C)C)c1]
TABLE 1-continued
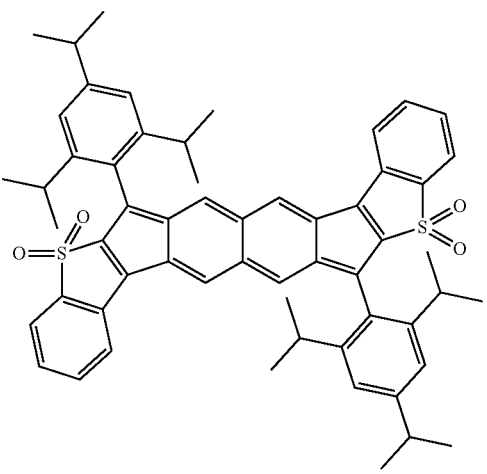 [SMILES: CC(C)c1cc(C(C)C)c(C2=c3cc4cc5c(cc4cc3C3=C2S(=O)(=O)c2ccccc23)=C(c2c(C(C)C)cc(C(C)C)cc2C(C)C)C2=C5c3ccccc3S2(=O)=O)c(C(C)C)c1]
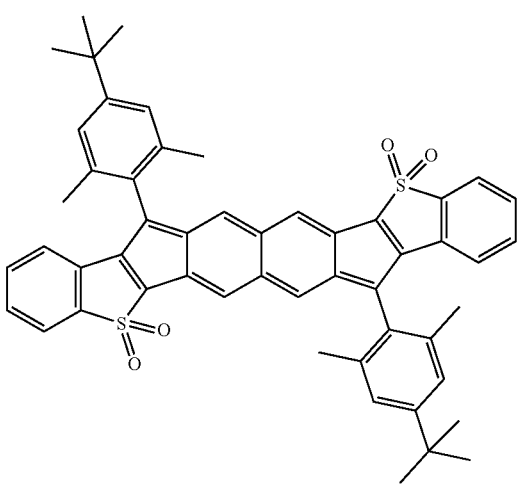 [SMILES: Cc1cc(C(C)(C)C)cc(C)c1C1=c2cc3cc4c(cc3cc2C2=C1c1ccccc1S2(=O)=O)=C(c1c(C)cc(C(C)(C)C)cc1C)C1=C4S(=O)(=O)c2ccccc21]
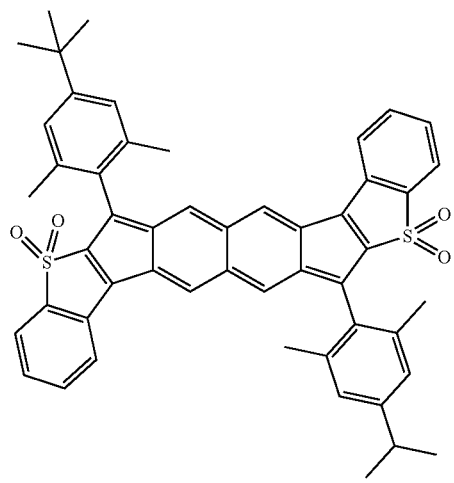 [SMILES: Cc1cc(C(C)C)cc(C)c1C1=c2cc3cc4c(cc3cc2C2=C1S(=O)(=O)c1ccccc12)=C(c1c(C)cc(C(C)(C)C)cc1C)C1=C4c2ccccc2S1(=O)=O]

TABLE 1-continued
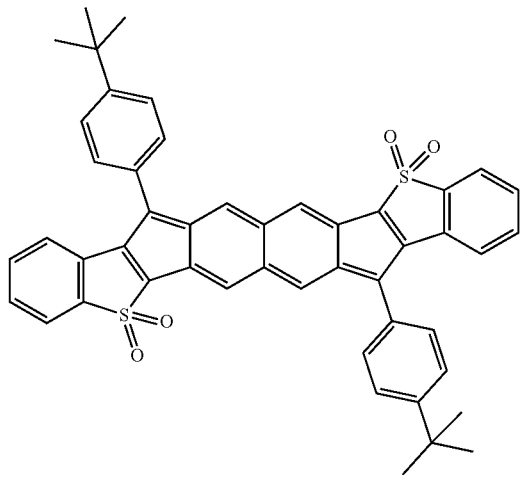 [SMILES: CC(C)(C)c1ccc(C2=c3cc4cc5c(cc4cc3C3=C2c2ccccc2S3(=O)=O)=C(c2ccc(C(C)(C)C)cc2)C2=C5S(=O)(=O)c3ccccc32)cc1]
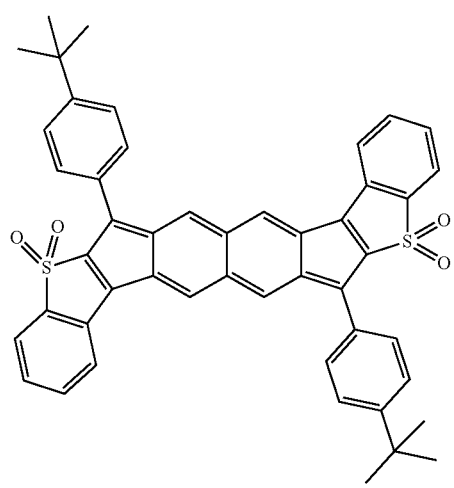 [SMILES: CC(C)(C)c1ccc(C2=c3cc4cc5c(cc4cc3C3=C2S(=O)(=O)c2ccccc23)=C(c2ccc(C(C)(C)C)cc2)C2=C5c3ccccc3S2(=O)=O)cc1]
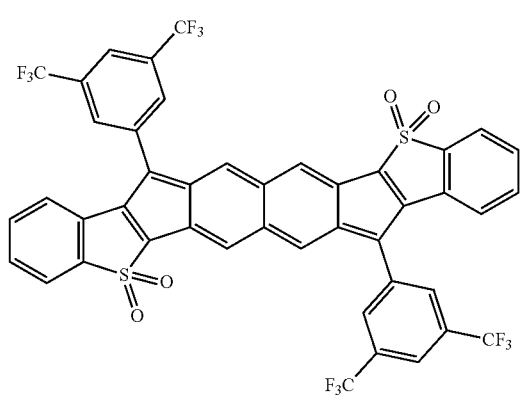 [SMILES: O=S1(=O)C2=C(C(c3cc(C(F)(F)F)cc(C(F)(F)F)c3)=c3cc4cc5c(cc4cc32)=C(c2cc(C(F)(F)F)cc(C(F)(F)F)c2)C2=C5S(=O)(=O)c3ccccc32)c2ccccc21]
TABLE 1-continued
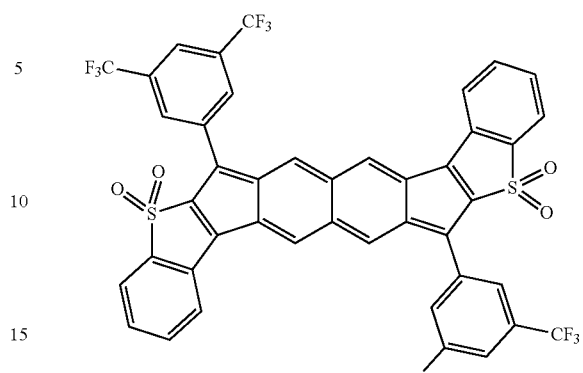
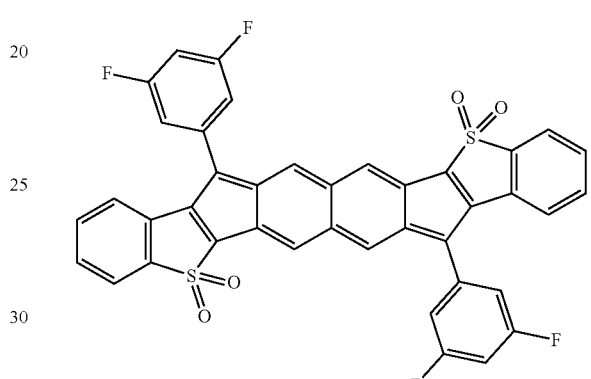
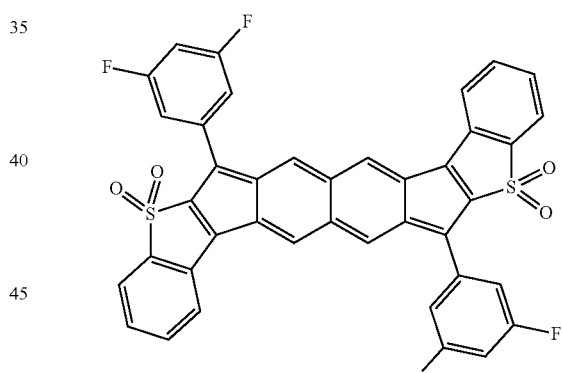
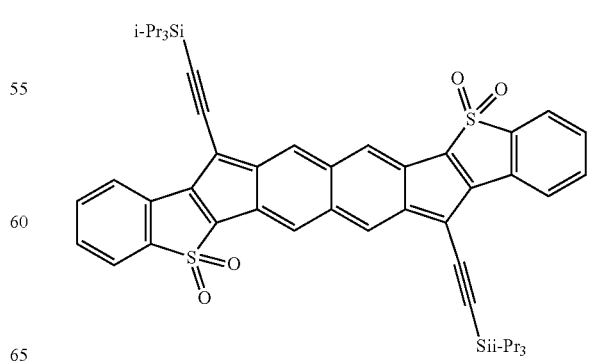

TABLE 1-continued
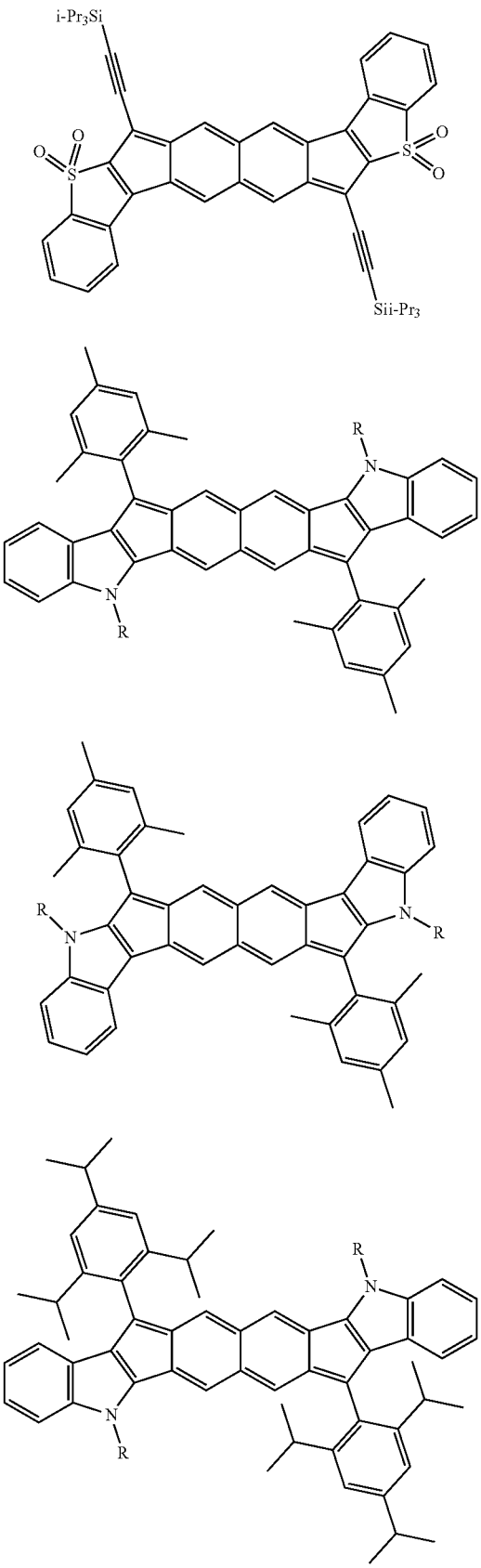
TABLE 1-continued
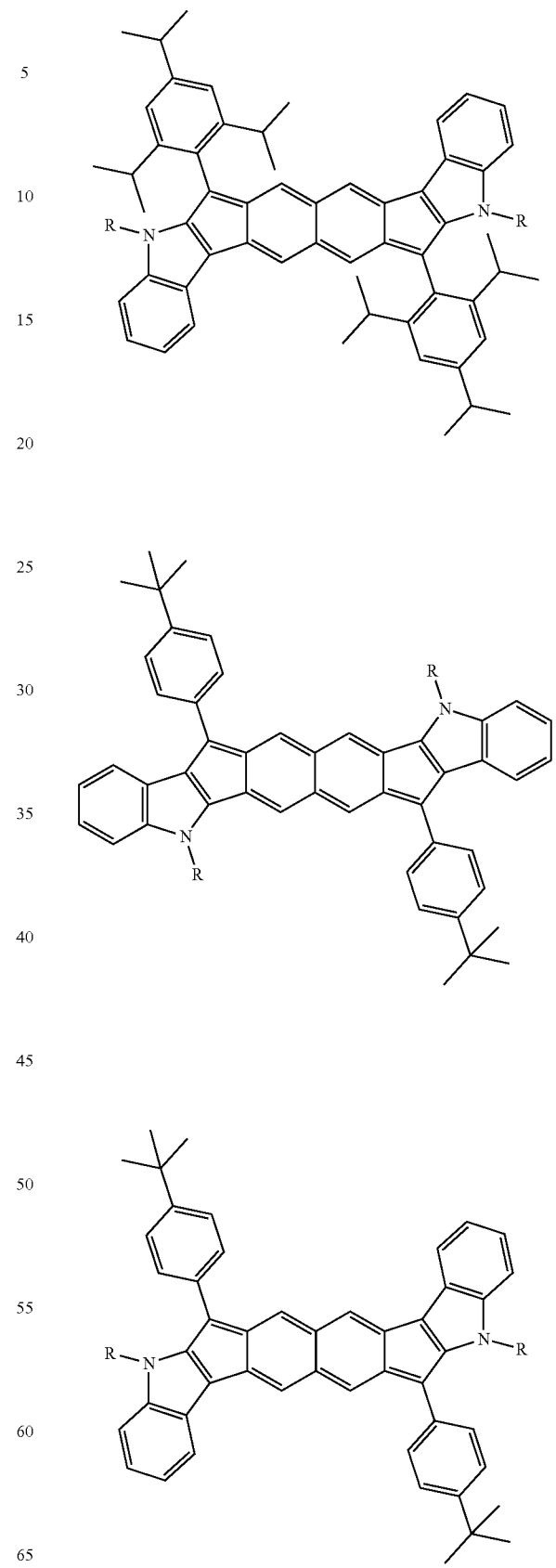

TABLE 1-continued
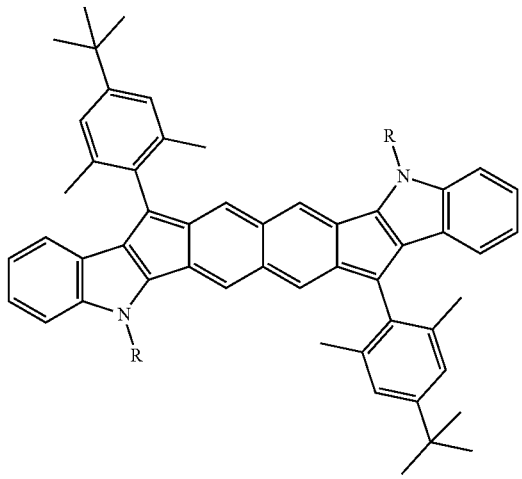
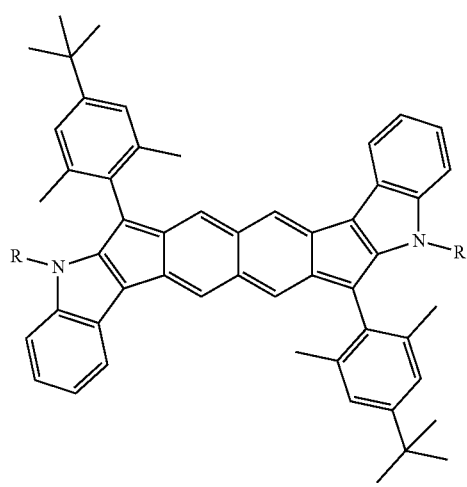
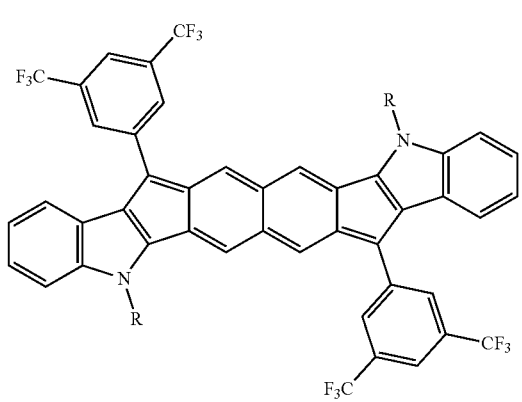
TABLE 1-continued
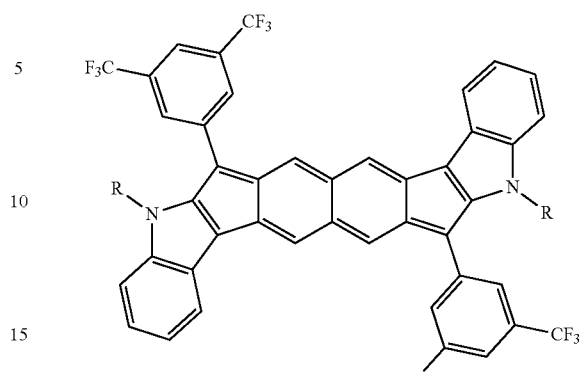
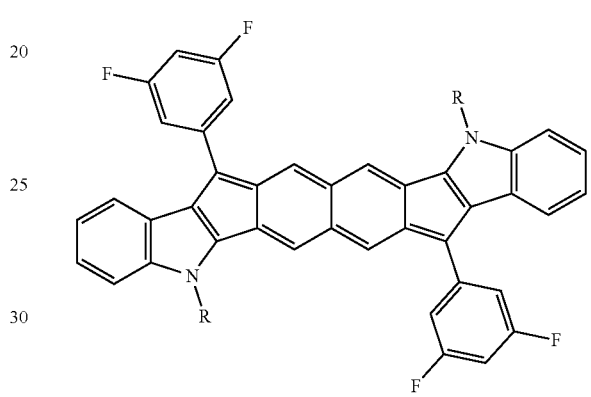
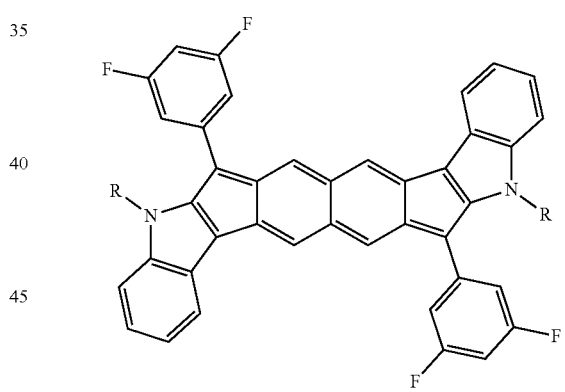
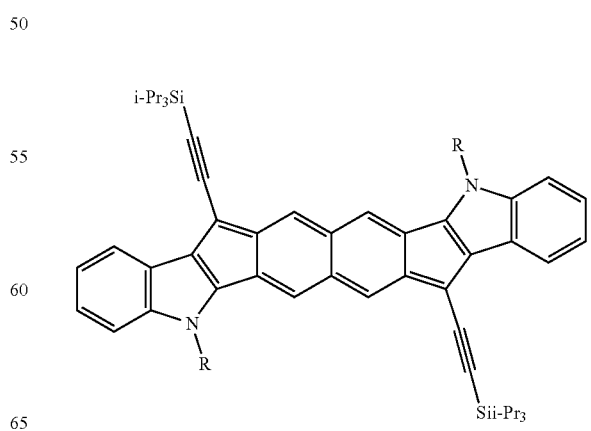

TABLE 1-continued
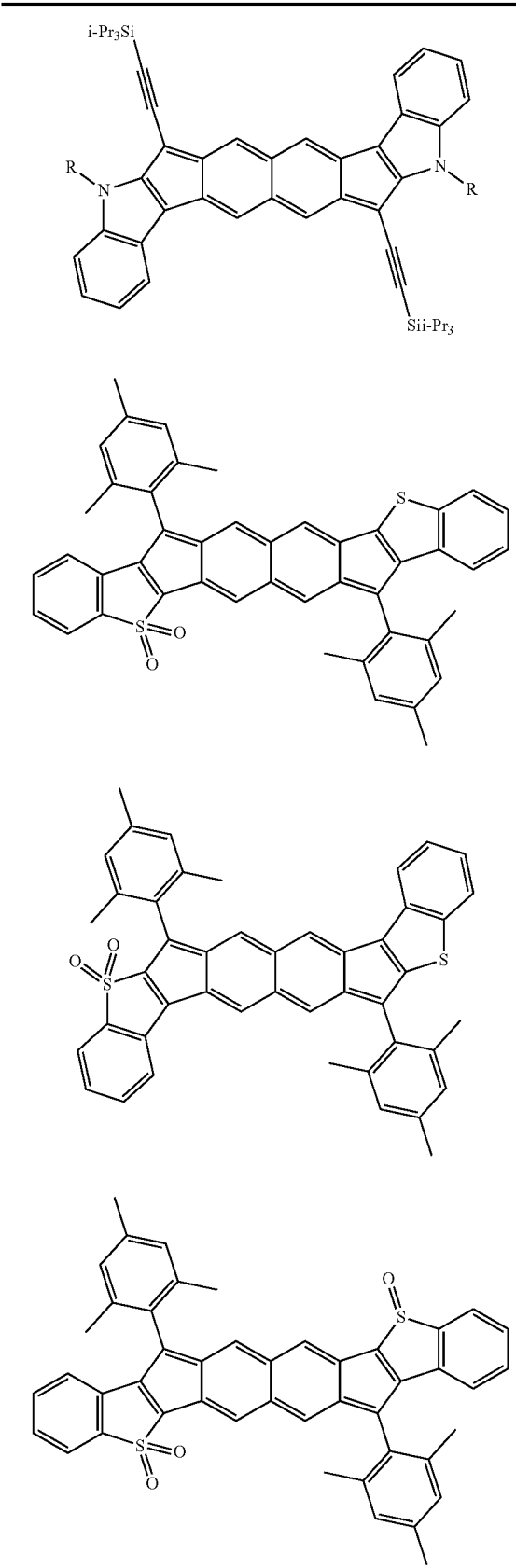
TABLE 1-continued
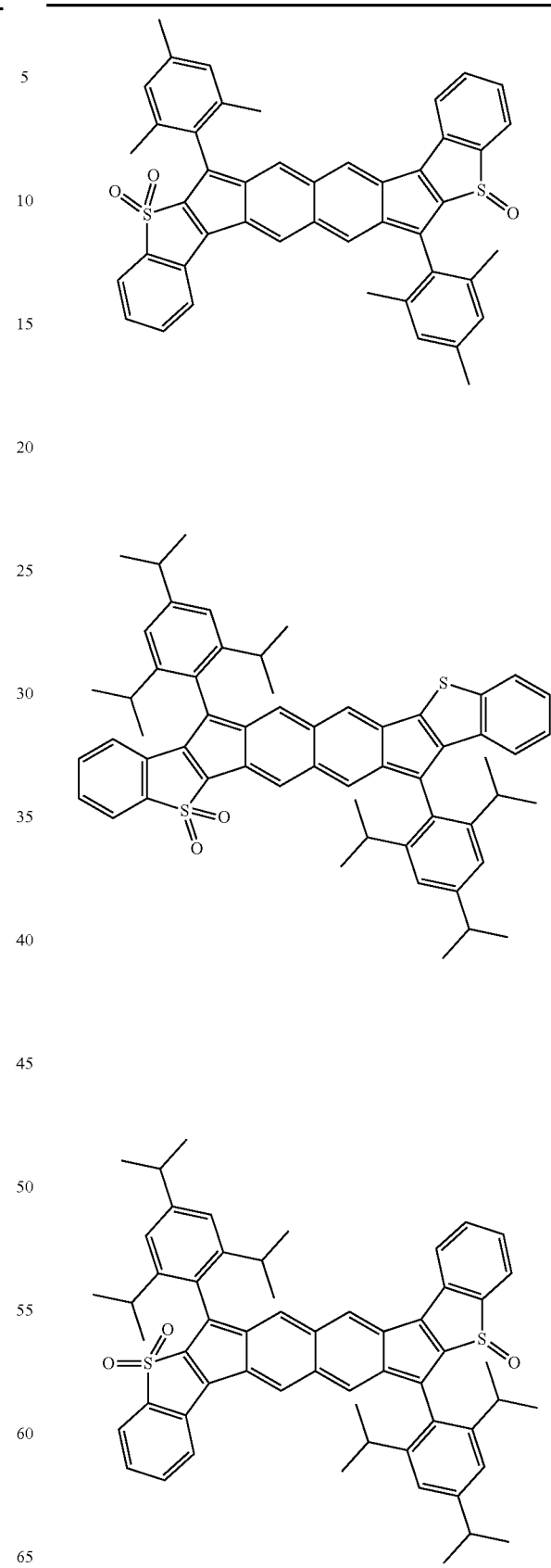

TABLE 1-continued
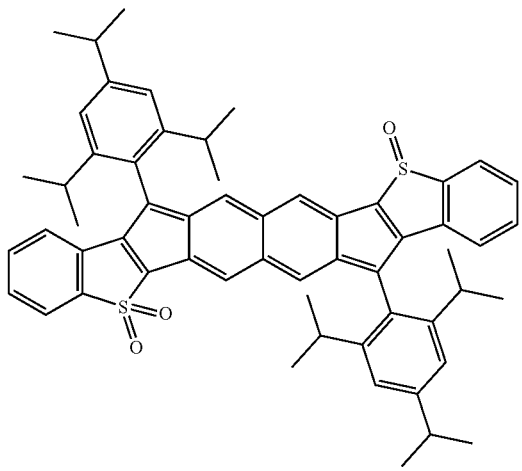 [SMILES: CC(C)c1cc(C(C)C)c(C2=c3cc4cc5c(cc4cc3C3=C2c2ccccc2S3=O)=C(c2c(C(C)C)cc(C(C)C)cc2C(C)C)C2=C5S(=O)(=O)c3ccccc32)c(C(C)C)c1]
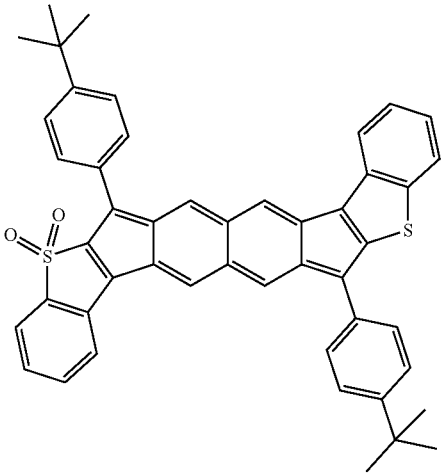
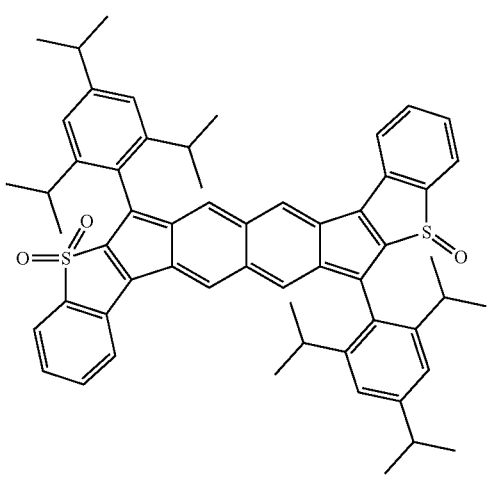 [SMILES: CC(C)c1cc(C(C)C)c(C2=c3cc4cc5c(cc4cc3C3=C2S(=O)c2ccccc23)=C(c2c(C(C)C)cc(C(C)C)cc2C(C)C)C2=C5c3ccccc3S2(=O)=O)c(C(C)C)c1]
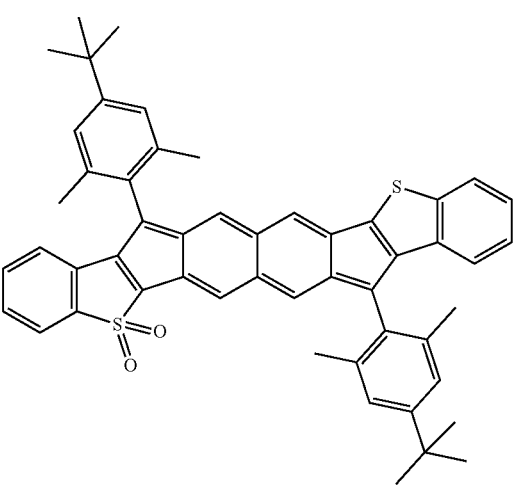
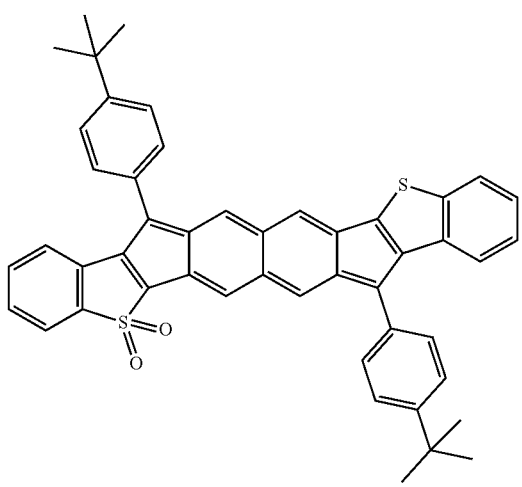
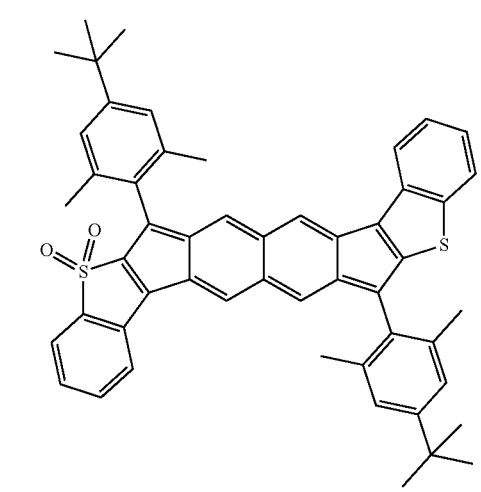 [SMILES: Cc1cc(C(C)(C)C)cc(C)c1C1=c2cc3cc4c(cc3cc2C2=C1S(=O)(=O)c1ccccc12)=C(c1c(C)cc(C(C)(C)C)cc1C)c1sc2ccccc2c1-4]

TABLE 1-continued
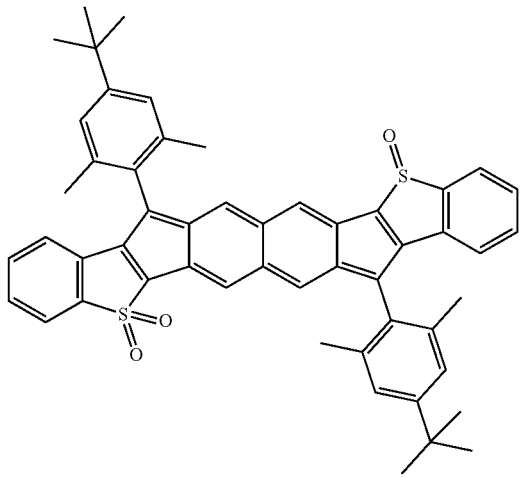 [SMILES: Cc1cc(C(C)(C)C)cc(C)c1C1=c2cc3cc4c(cc3cc2C2=C1c1ccccc1S2=O)=C(c1c(C)cc(C(C)(C)C)cc1C)C1=C4S(=O)(=O)c2ccccc21]
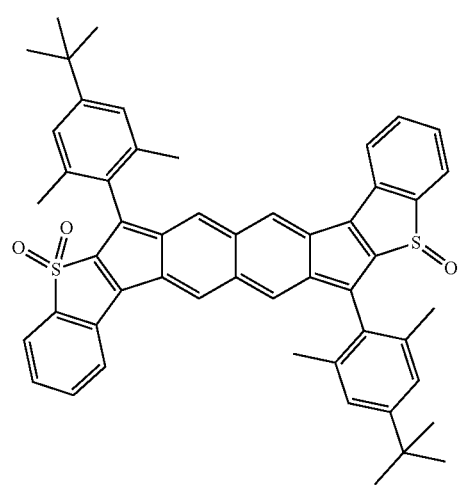 [SMILES: Cc1cc(C(C)(C)C)cc(C)c1C1=c2cc3cc4c(cc3cc2C2=C1S(=O)c1ccccc12)=C(c1c(C)cc(C(C)(C)C)cc1C)C1=C4c2ccccc2S1(=O)=O]
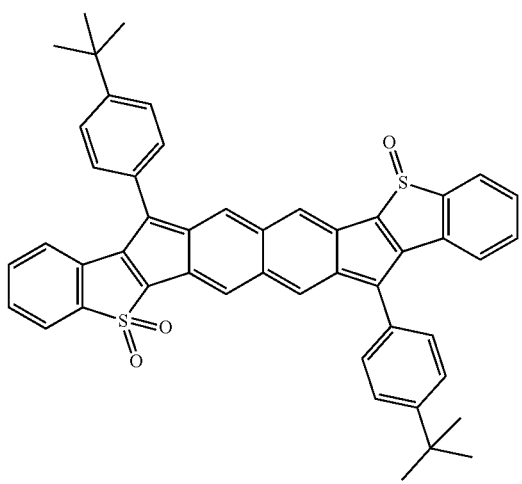 [SMILES: CC(C)(C)c1ccc(C2=c3cc4cc5c(cc4cc3C3=C2c2ccccc2S3=O)=C(c2ccc(C(C)(C)C)cc2)C2=C5S(=O)(=O)c3ccccc32)cc1]
TABLE 1-continued
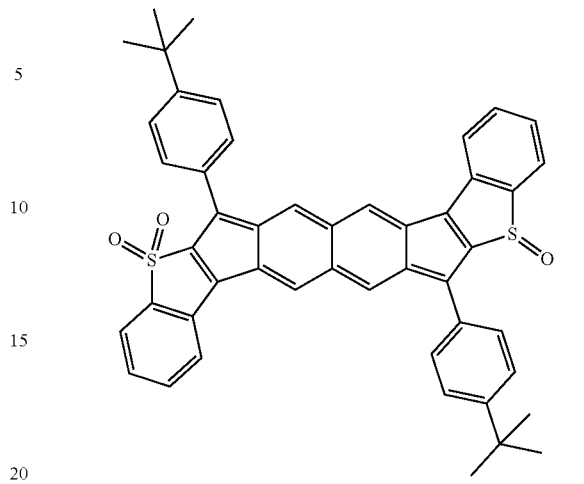
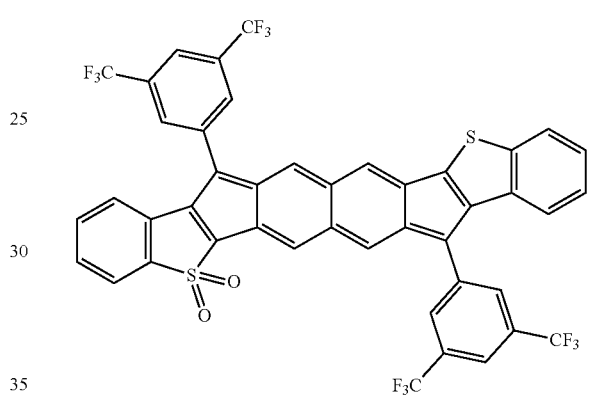
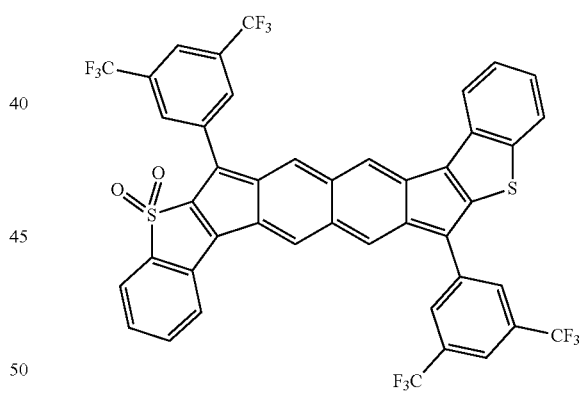
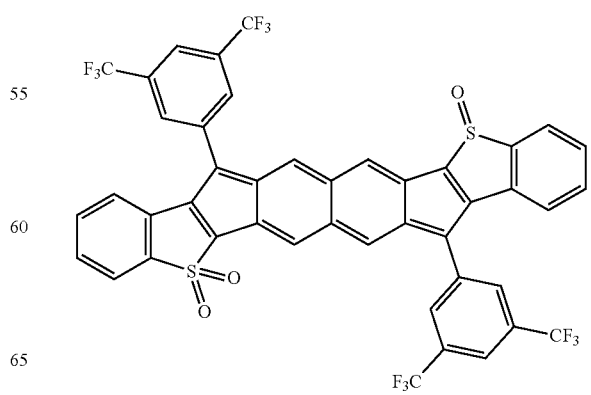

TABLE 1-continued
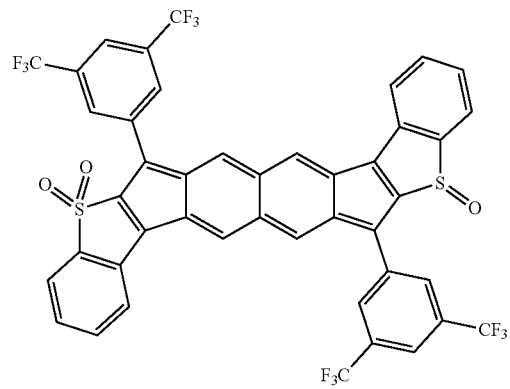 [SMILES: O=S1C2=C(c3ccccc31)c1cc3cc4c(cc3cc1=C2c1cc(C(F)(F)F)cc(C(F)(F)F)c1)C1=C(C=4c2cc(C(F)(F)F)cc(C(F)(F)F)c2)S(=O)(=O)c2ccccc21]
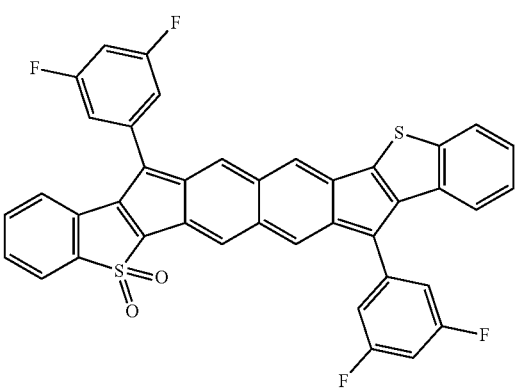 [SMILES: O=S1(=O)C2=C(C(c3cc(F)cc(F)c3)=c3cc4cc5c(cc4cc32)=C(c2cc(F)cc(F)c2)c2c-5sc3ccccc23)c2ccccc21]
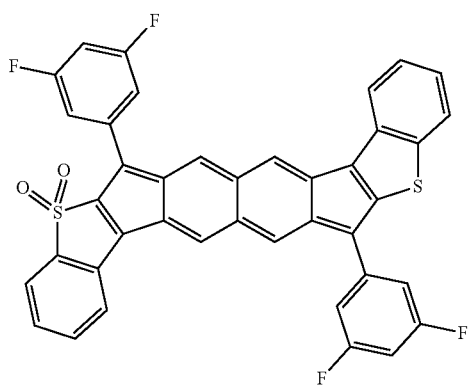 [SMILES: O=S1(=O)C2=C(c3ccccc31)c1cc3cc4c(cc3cc1=C2c1cc(F)cc(F)c1)-c1c(sc2ccccc12)C=4c1cc(F)cc(F)c1]
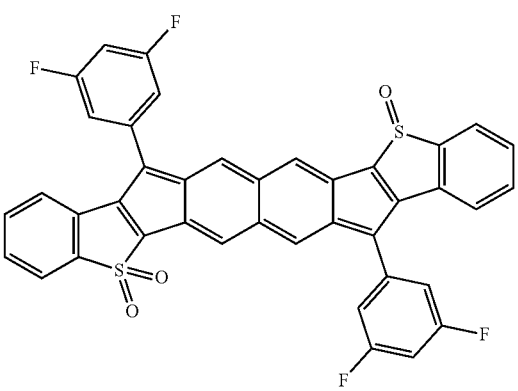 [SMILES: O=S1C2=C(C(c3cc(F)cc(F)c3)=c3cc4cc5c(cc4cc32)=C(c2cc(F)cc(F)c2)C2=C5S(=O)(=O)c3ccccc32)c2ccccc21]
TABLE 1-continued
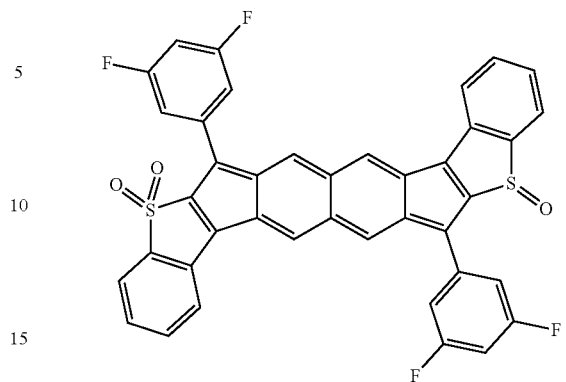
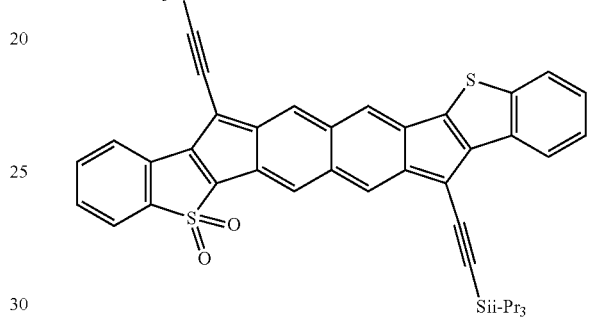
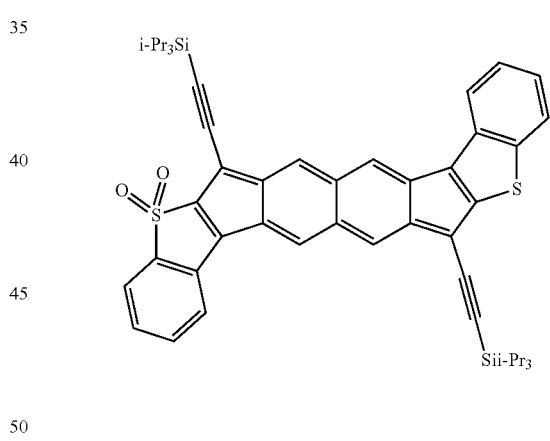
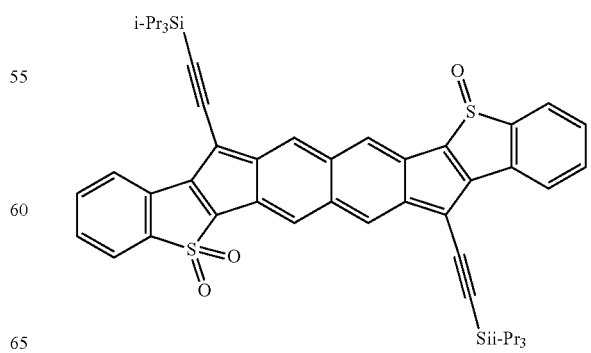

TABLE 1-continued
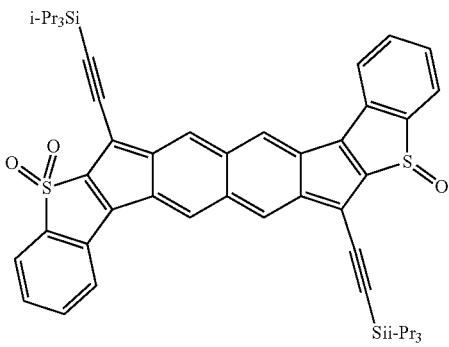
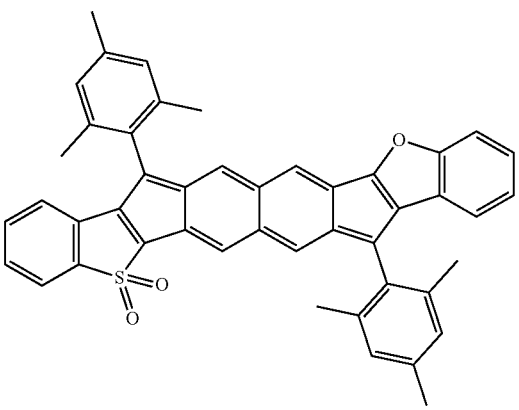
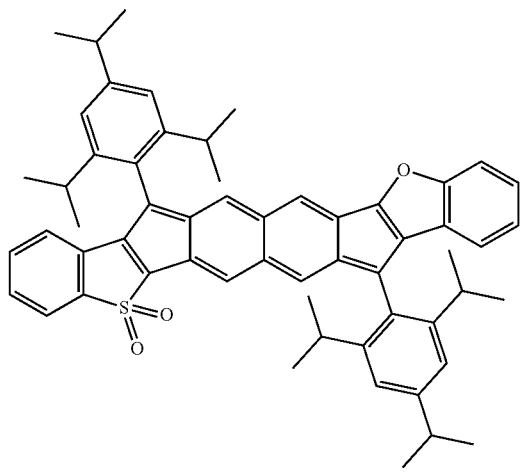 [SMILES: CC(C)c1cc(C(C)C)c(C2=c3cc4cc5c(cc4cc3C3=C2c2ccccc2S3(=O)=O)=C(c2c(C(C)C)cc(C(C)C)cc2C(C)C)c2c-5oc3ccccc23)c(C(C)C)c1]
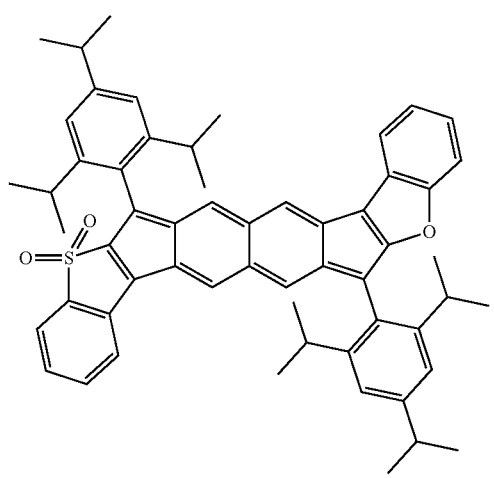 [SMILES: CC(C)c1cc(C(C)C)c(C2=c3cc4cc5c(cc4cc3C3=C2S(=O)(=O)c2ccccc23)=C(c2c(C(C)C)cc(C(C)C)cc2C(C)C)c2oc3ccccc3c2-5)c(C(C)C)c1]

TABLE 1-continued
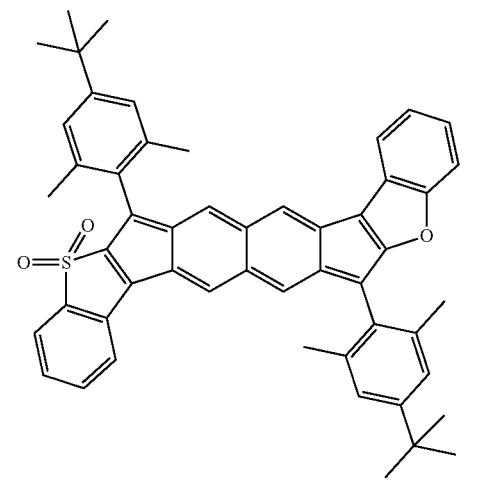 [SMILES: Cc1cc(C(C)(C)C)cc(C)c1C1=c2cc3cc4c(cc3cc2C2=C1S(=O)(=O)c1ccccc12)=C(c1c(C)cc(C(C)(C)C)cc1C)c1oc2ccccc2c1-4]
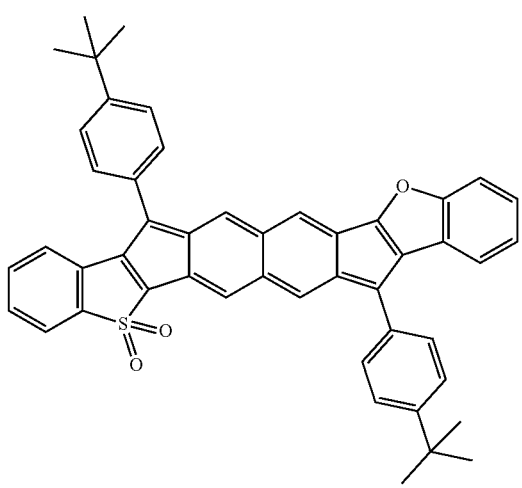 [SMILES: CC(C)(C)c1ccc(C2=c3cc4cc5c(cc4cc3C3=C2c2ccccc2S3(=O)=O)=C(c2ccc(C(C)(C)C)cc2)c2c-5oc3ccccc23)cc1]
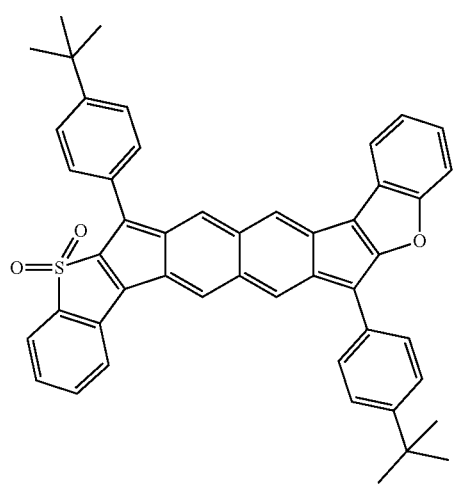 [SMILES: CC(C)(C)c1ccc(C2=c3cc4cc5c(cc4cc3C3=C2S(=O)(=O)c2ccccc23)=C(c2ccc(C(C)(C)C)cc2)c2oc3ccccc3c2-5)cc1]
TABLE 1-continued
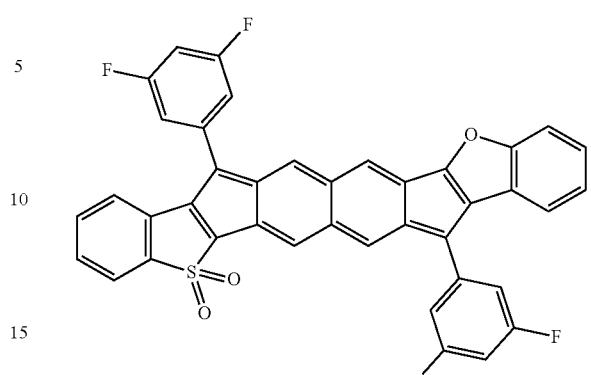
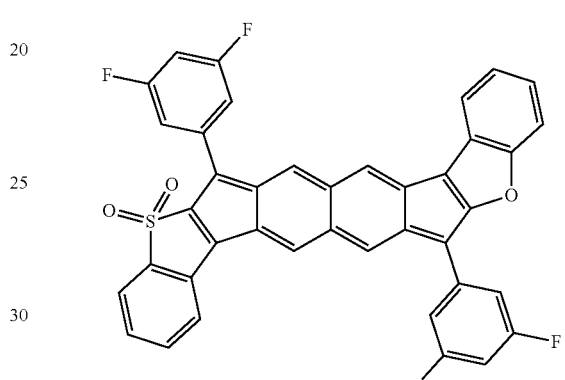
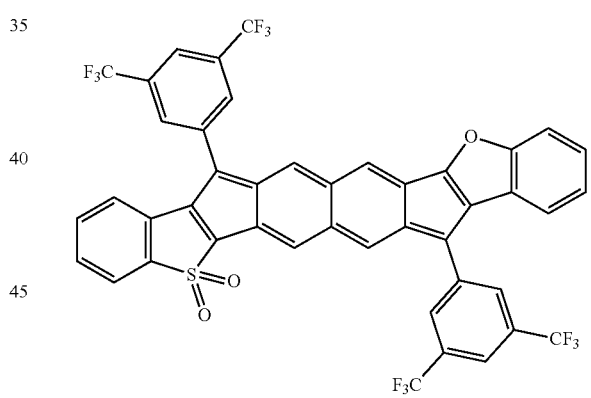
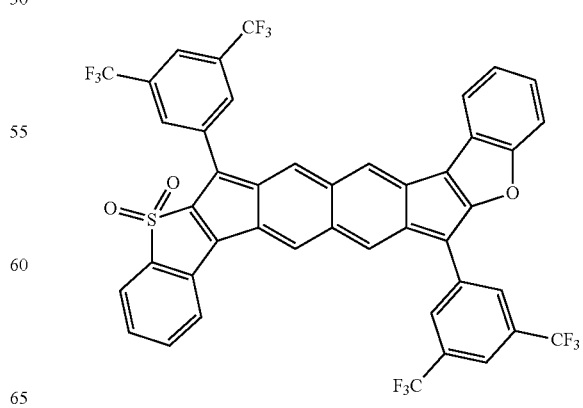

TABLE 1-continued
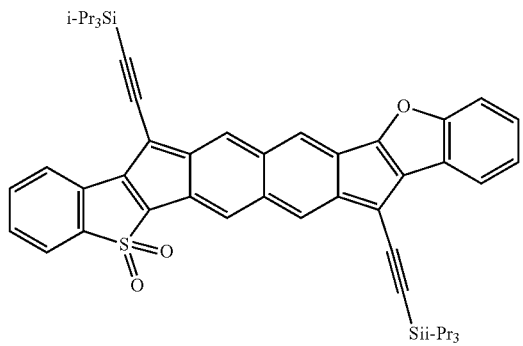
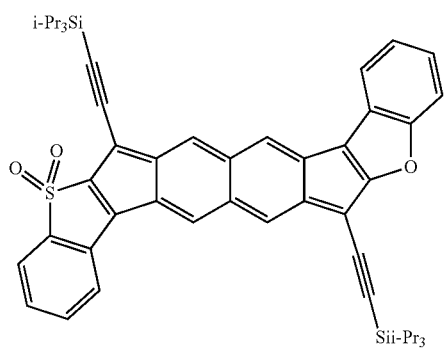
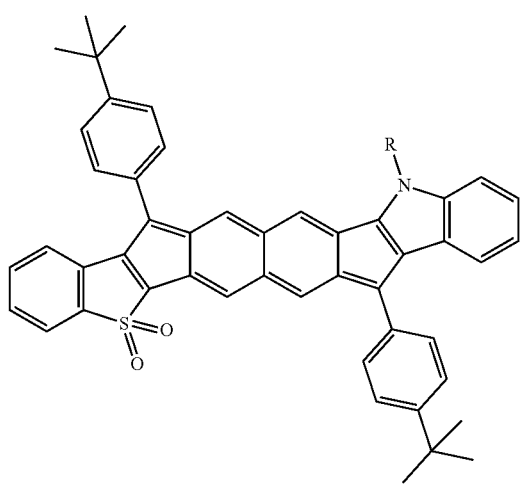
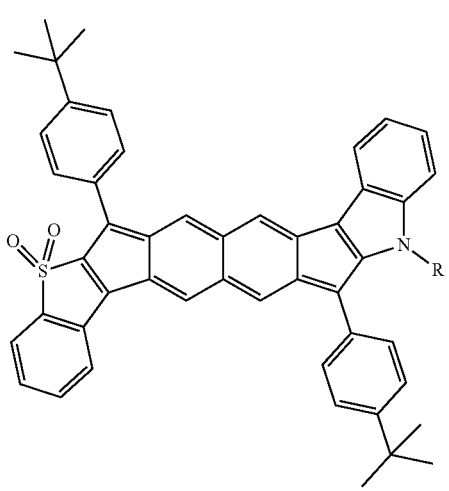
TABLE 1-continued
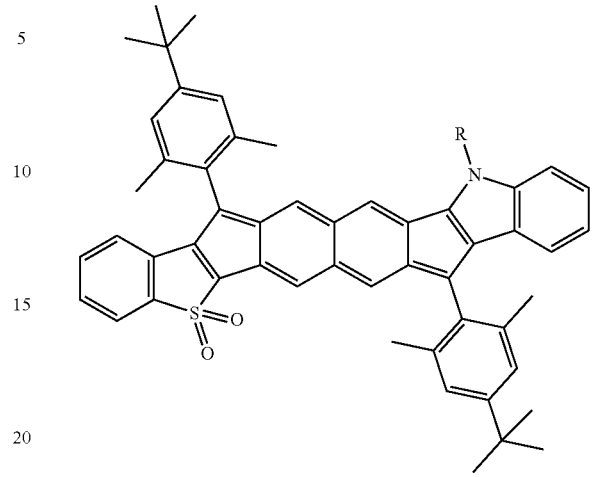
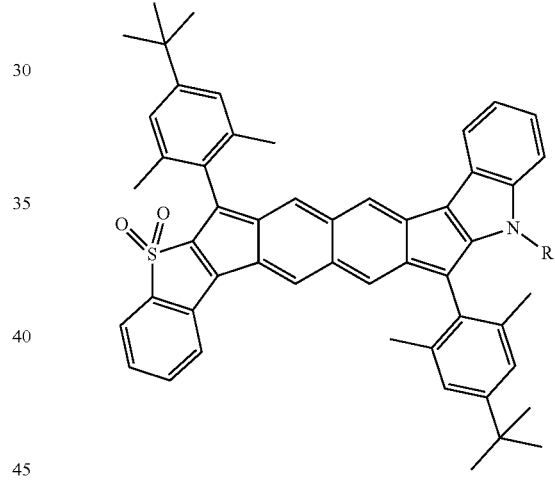
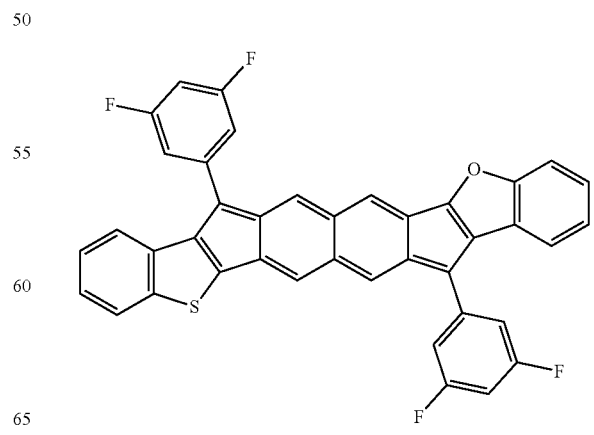

TABLE 1-continued
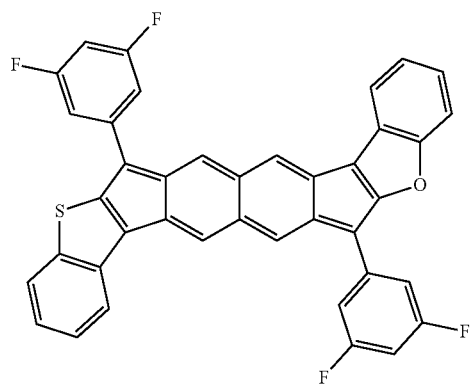
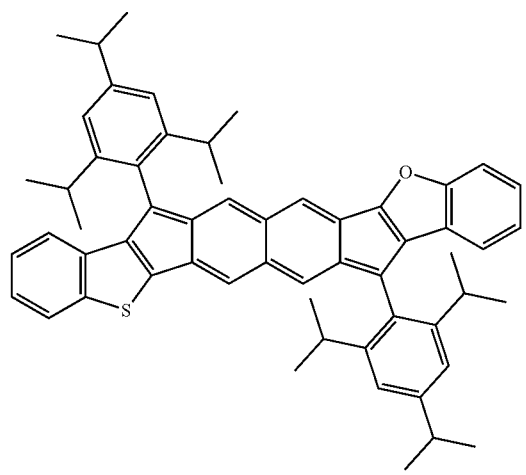
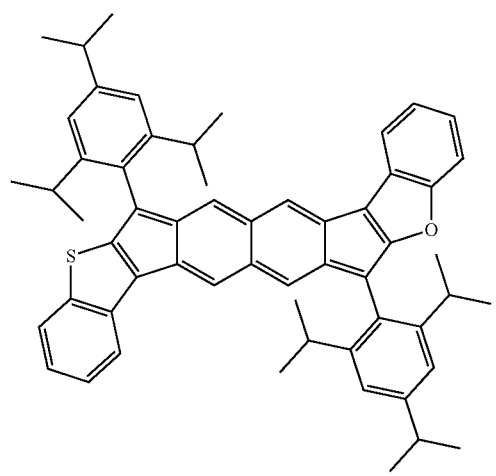 [SMILES: CC(C)c1cc(C(C)C)c(C2=c3cc4cc5c(cc4cc3-c3c2oc2ccccc32)=C(c2c(C(C)C)cc(C(C)C)cc2C(C)C)c2sc3ccccc3c2-5)c(C(C)C)c1]
TABLE 1-continued
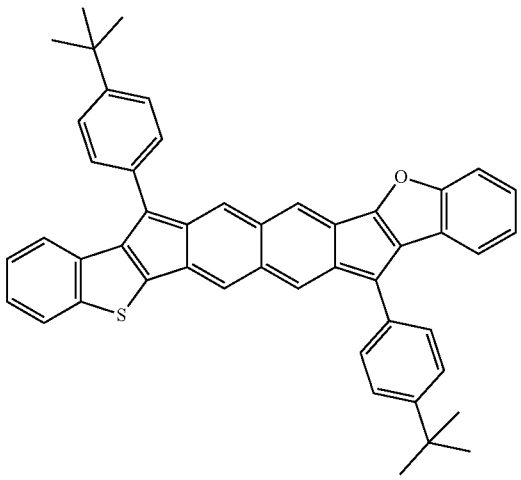 [SMILES: CC(C)(C)c1ccc(C2=c3cc4cc5c(cc4cc3-c3oc4ccccc4c32)=C(c2ccc(C(C)(C)C)cc2)c2c-5sc3ccccc23)cc1]
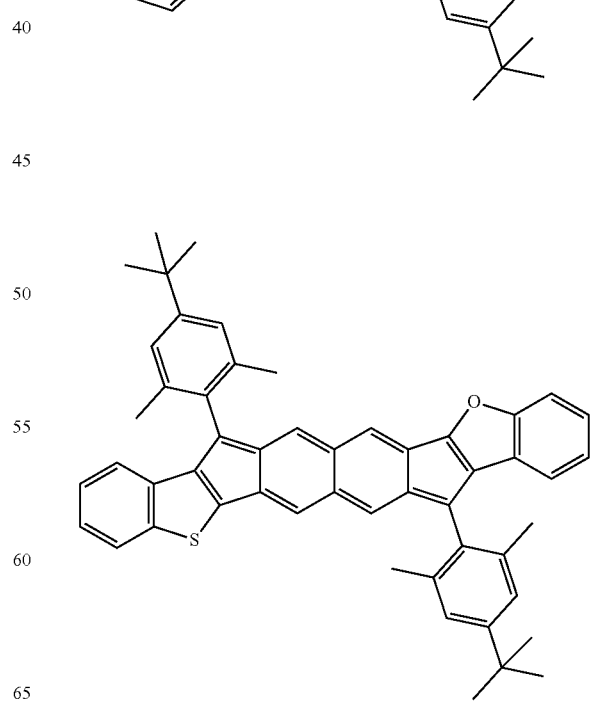

TABLE 1-continued
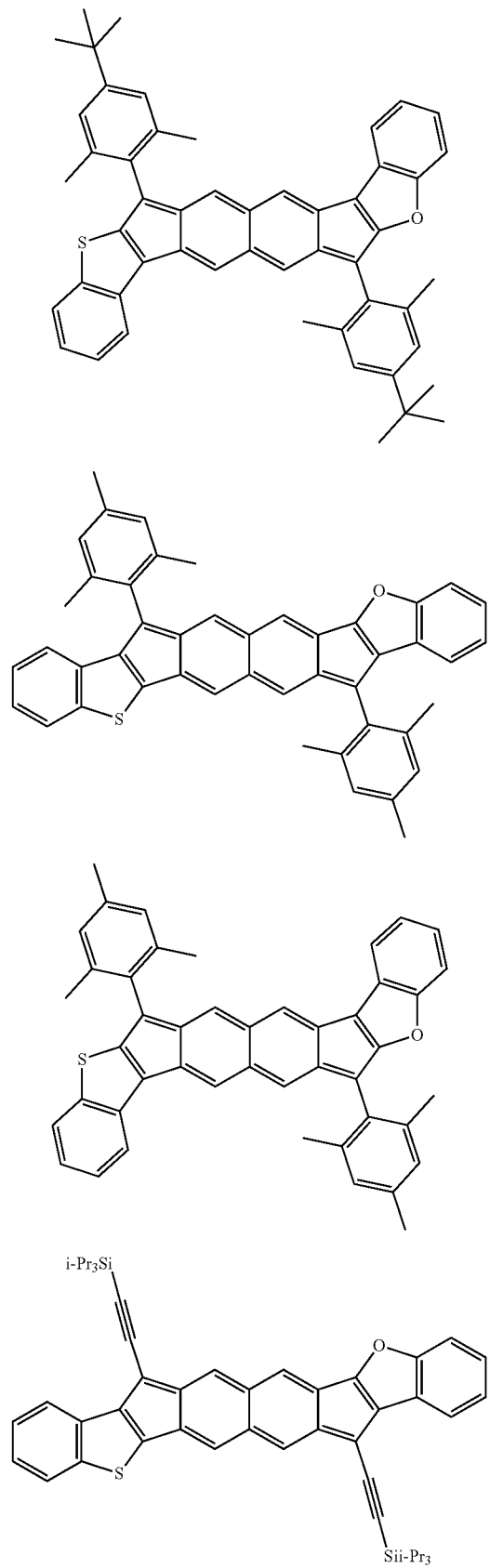
TABLE 1-continued
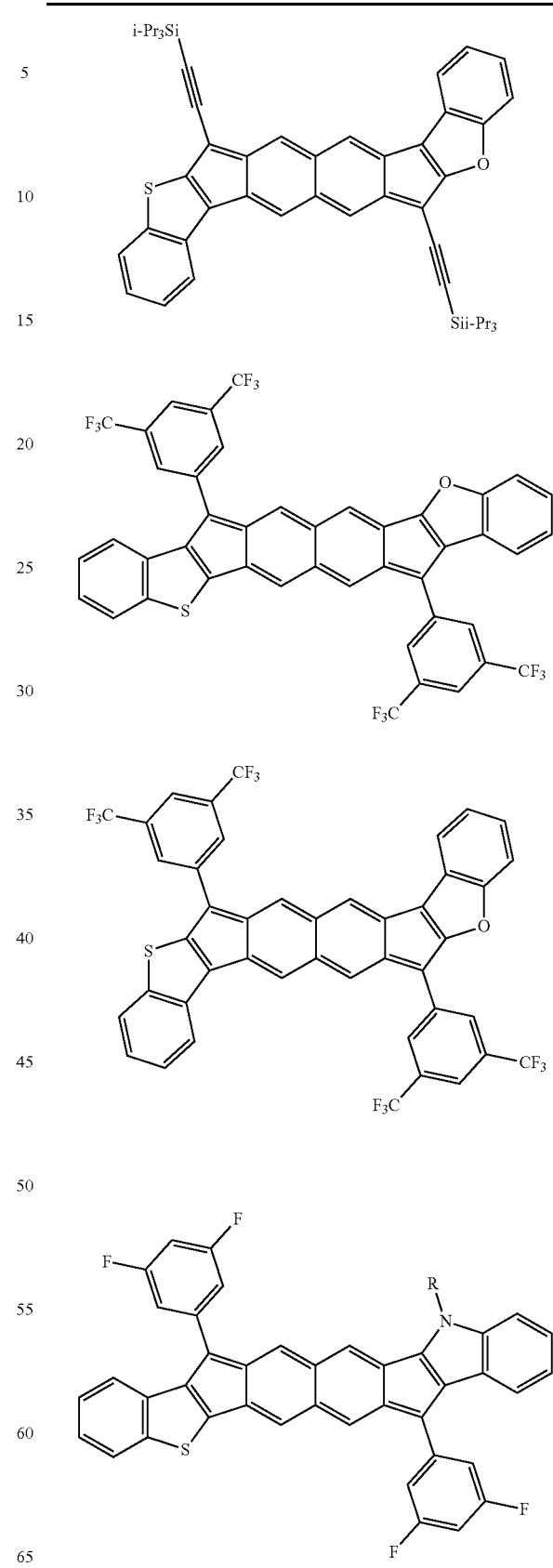

TABLE 1-continued

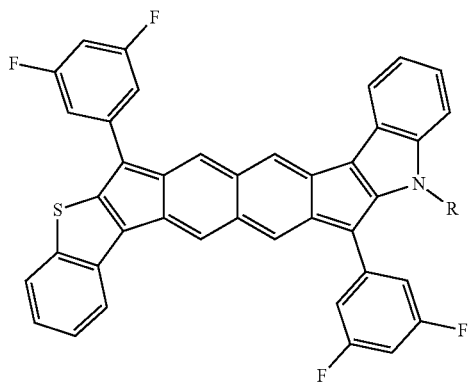

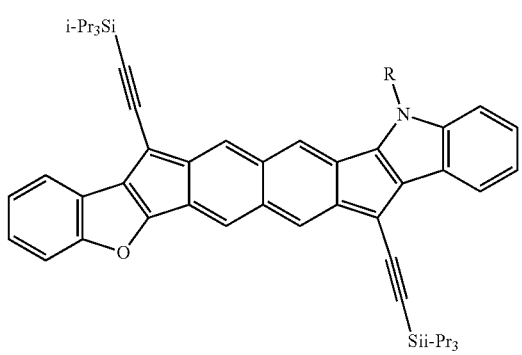

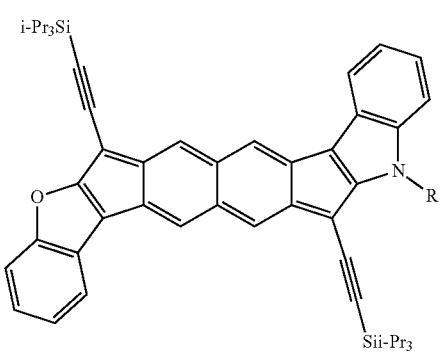

With reference to the compounds illustrated above, R hydrogen, aliphatic, heteroaliphatic, haloaliphatic, haloheteroaliphatic, aromatic, or an organic functional group.

IV. Method Embodiments

A. Uses

The polycyclic aromatic compound embodiments disclosed herein may be used in electronic or electrooptical applications, such as in electronic and/or electrooptical devices. The compound embodiments disclosed herein have structures that facilitate their use in such applications. Without being limited to a single theory, it currently is believed that the compound embodiments disclosed herein exhibit unique diradical characteristics that provide electronic properties lending to their use in electronic and/or electrooptical devices. In some embodiments, the compounds exhibit strong diradical character and unusually large singlet-triplet energy gaps, which can be tuned to thereby control the compound's optical and/or magnetic properties.

Compound embodiments disclosed herein can be used, for example, in electronic and electrooptical devices, such as organic light-emitting diodes (OLED), organic field-effect transistors (OFET), organic photovoltaic cells (OPV), and the like. Particular compound embodiments provide optical and/or magnetic properties that facilitate effecting the changes needed to operate such devices at ambient temperatures. In some embodiments, compound embodiments disclosed herein may be used as organic semiconductors in form of thin organic layers or films, for example, less than 30 microns thick. In yet some additional embodiments, a semiconducting layer comprising a compound embodiment disclosed herein can be at most 1 micron thick, although it may be thicker if required. For some electronic device applications, the thickness may be less than 1 micron thick. For use in an OFET, the layer thickness may be 500 nm or less. For use in an OLED, the layer thickness may be 100 nm or less.

Devices comprising a compound embodiment as disclosed herein (e.g., as a thin organic layer) can comprise the compound (or a mixture of such compounds) in any suitable area of the device. Solely by way of example, an active semiconductor channel between a drain and a source in an OFET device may comprise a layer that includes the compound (or mixture of compounds). As another example, a hole injection or transport layer and/or an electron blocking layer in an OLED device may comprise a layer that includes the compound (or compounds.

An OFET device can comprise a source electrode, a drain electrode, a gate electrode, a semiconducting layer, and one or more gate insulator layers, wherein the semiconductor layer comprises one or more of the disclosed compound embodiments. In some embodiments, an OFET device can further comprise a substrate.

A photovoltaic cell also is another exemplary device that can be used in combination with compound embodiments of the present disclosure. Such cells typically include an anode, a cathode, and a semiconductor layer or film that comprises one or more compound embodiments of the present disclosure.

B. Methods of Making Compounds

Also disclosed herein are embodiments of a method for making compound embodiments described herein. In some embodiments, the method can comprise steps summarized below in Schemes 1 and 2.

Scheme 1

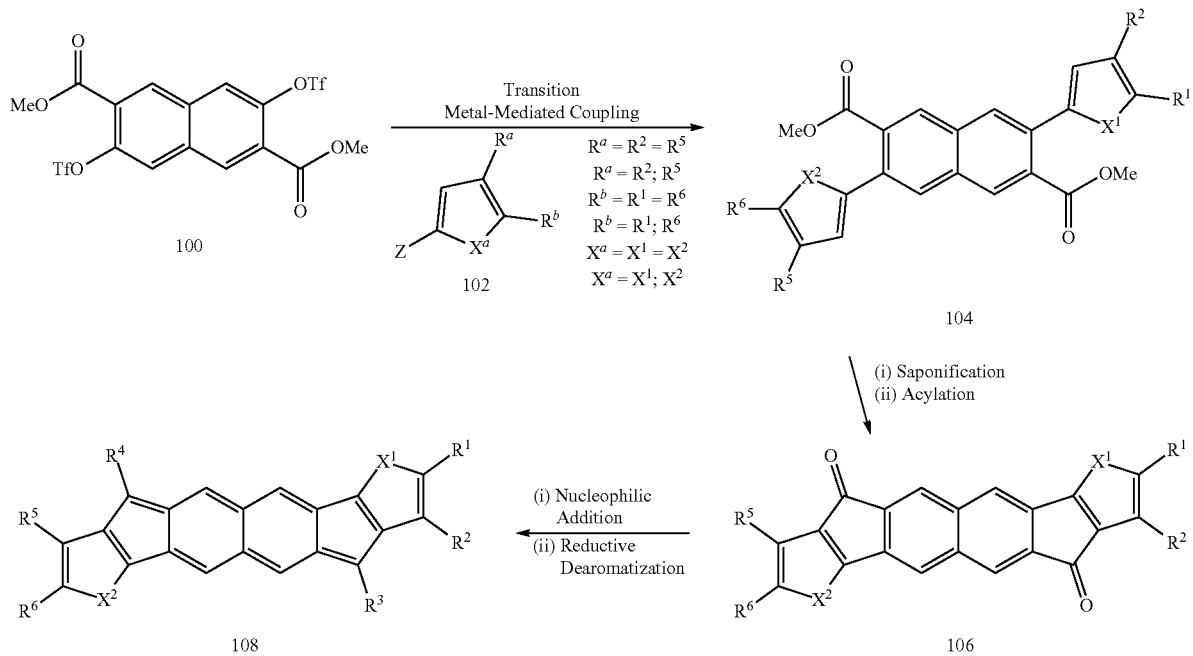

Scheme 2

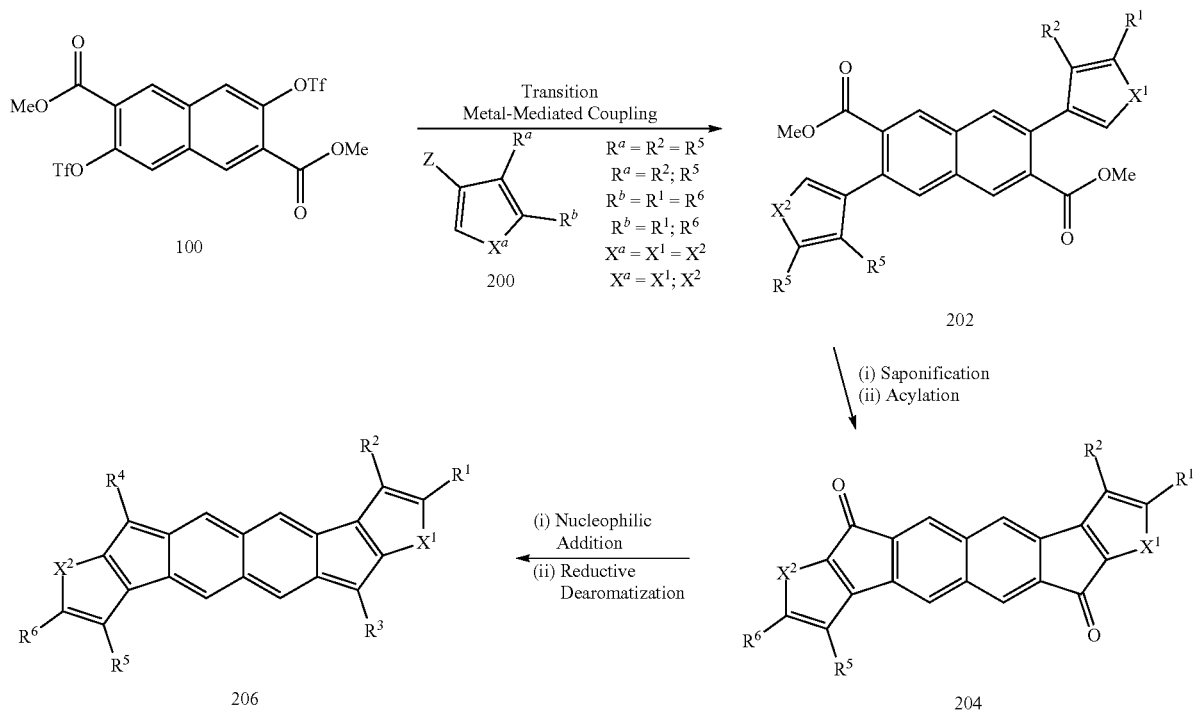

With reference to Schemes 1 and 2, starting material 100 can be subjected to a transition metal-mediated coupling reaction with coupling partner 102 (wherein Z is a boronic acid or boronic ester, such as pinacolborane [or "Bpin"]) to provide intermediate 104. Suitable conditions for the transition metal-mediated coupling reaction can include, but are not limited to, palladium-mediated reactions using a palladium catalyst (e.g., $Pd(PPh_3)_4$, $Pd(OAc)_2$, $Pd(dba)_2$ and the like), a base (e.g., $Na_2Co_3$, $K_3PO_4$, $K_2CO_3$, and the like), and a solvent (e.g., toluene, xylenes, an aqueous alcohol, and the like), in combination with coupling partner 102. After saponification and acylation of intermediate 104, dione 106 is obtained. The saponification step can comprise using a base, such as NaOH, and an alcohol, such as EtOH, with water. The acylation step can be a Friedel-Crafts acylation, which uses an acylating reagent, such as $(COCl)_2$, with an appropriate solvent, such as an organic solvent system (e.g., DMF, $CH_2Cl_2$, and a combination thereof) and a Lewis acid, such as $AlCl_3$. Dione 106 can then undergo a nucleophilic addition reaction, followed by a reductive dearomatization step, to provide polycyclic aromatic compound 108. Any desired $R^3$ and $R^4$ group can be introduced in the nucleophilic addition reaction step, which comprises adding a lithiated nucleophile into the dione functionality. After the $R^3$ and/or $R^4$ groups have been added, reductive dearomatization using $SnCl_2$ and TFA, can be performed to provide polycyclic aromatic compound 108.

Representative methods for making representative compound embodiments disclosed herein are described below in Schemes 3-6.

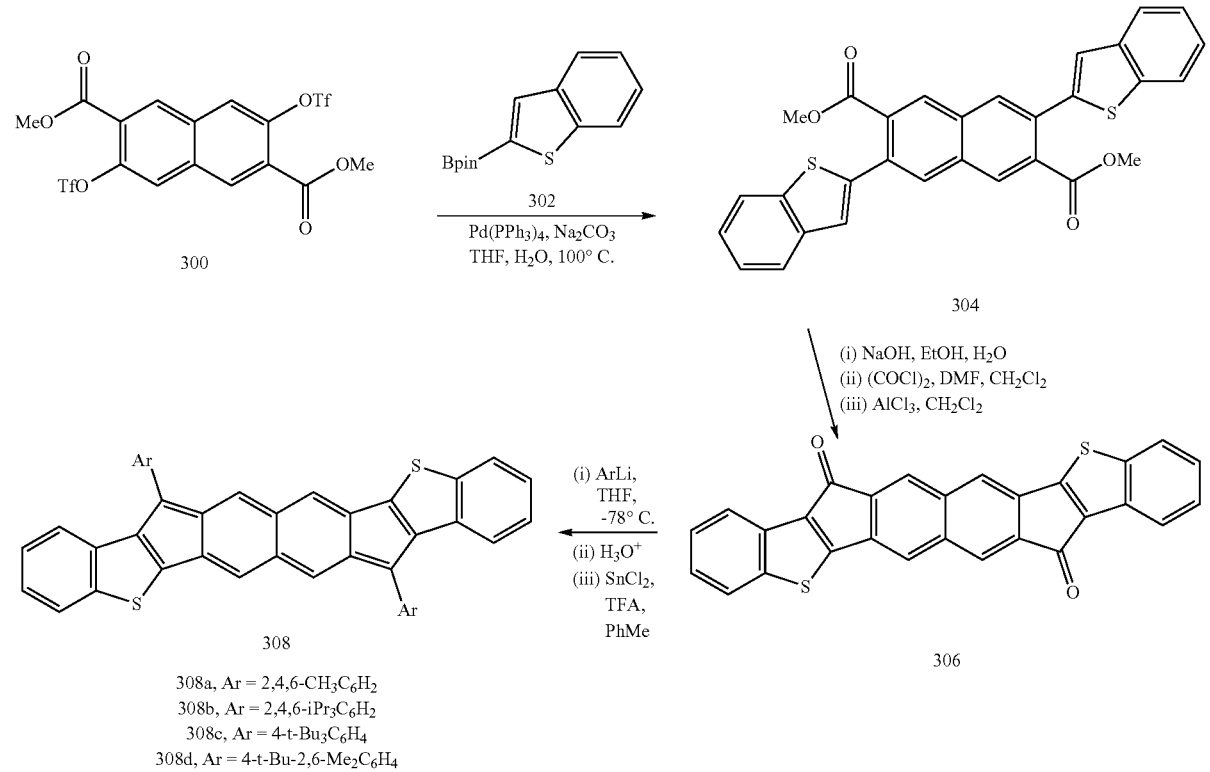

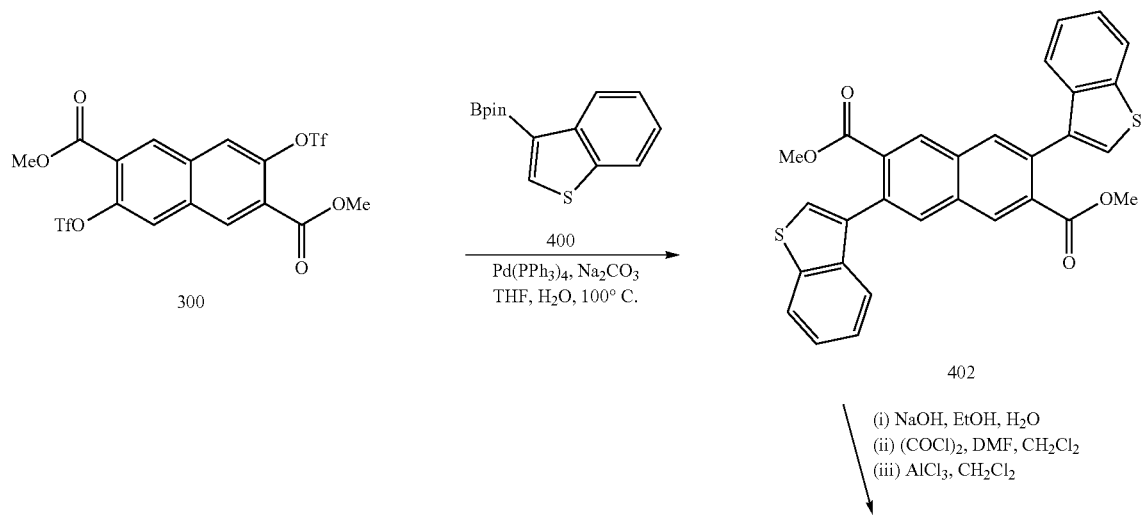

-continued
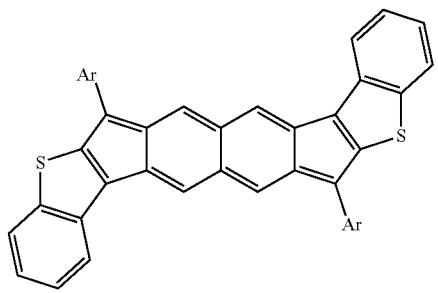
406
406a, Ar = 2,4,6-CH₃C₆H₂
406b, Ar = 2,4,6-iPr₃C₆H₂
406c, Ar = 4-t-Bu₃C₆H₄
(i) ArLi,
THF,
-78° C.
(ii) H₃O⁺
(iii) SnCl₂,
TFA,
PhMe
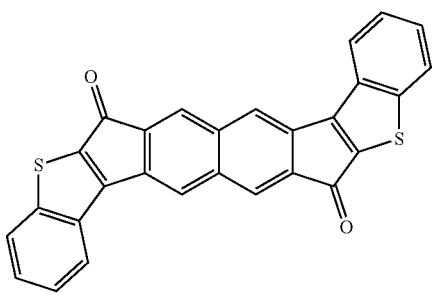
404
Scheme 5
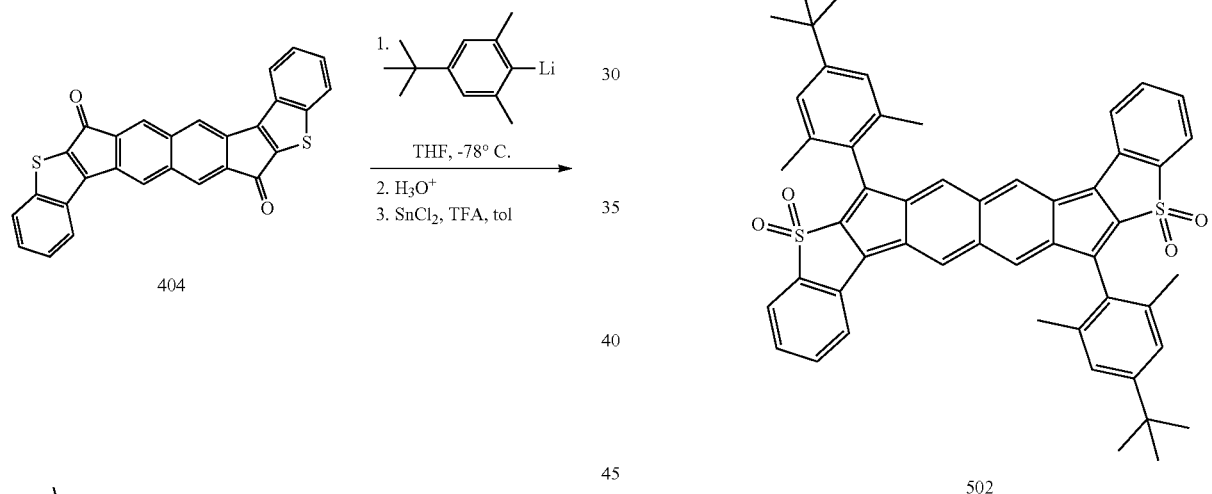
404
1. [mesityl-tBu]-Li
THF, -78° C.
2. H₃O⁺
3. SnCl₂, TFA, tol
502
(48%)
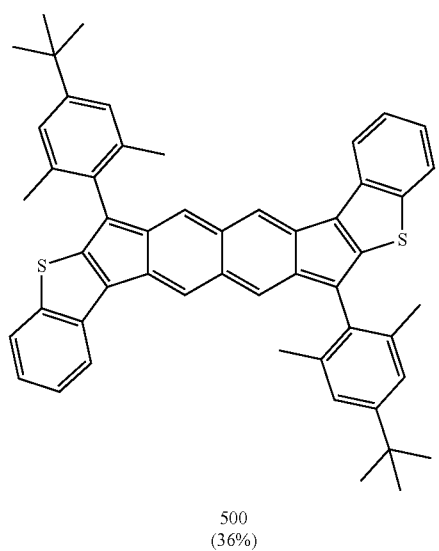
500
(36%)
m-CPBA
DCM. 21 h
Scheme 6
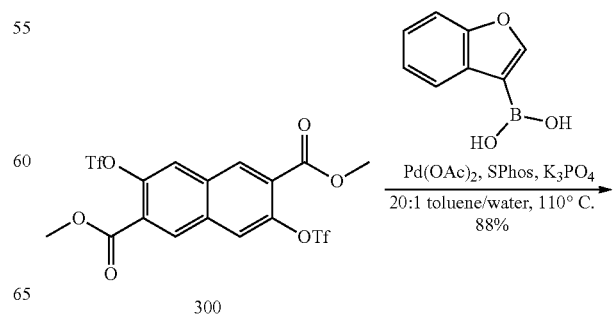
300

55
-continued

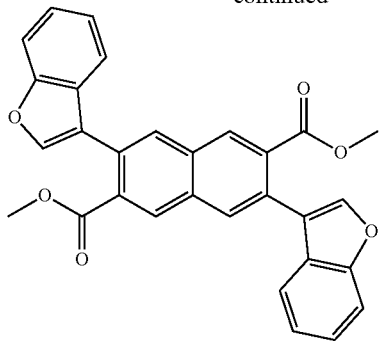

600

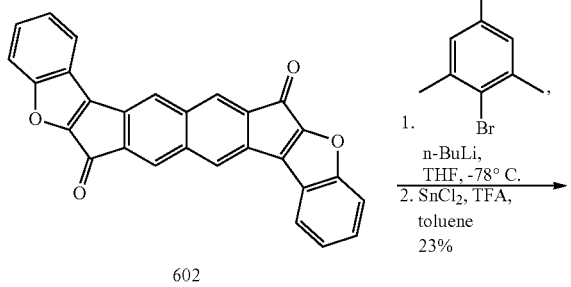

602

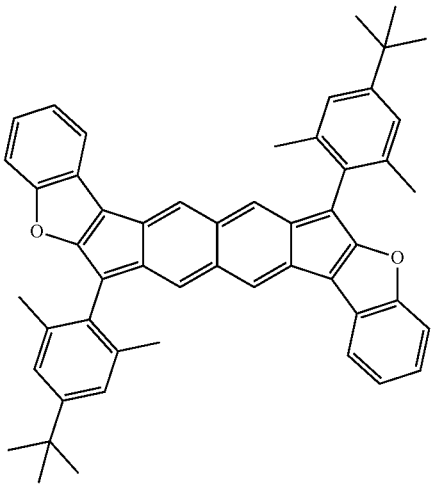

604

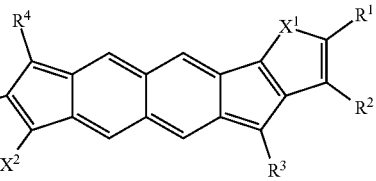

i) (COCl)₂, DMF, DCM, r.t.
ii) AlCl₃, DCM
50%

1. n-BuLi, THF, -78° C.
2. SnCl₂, TFA, toluene
23%

V. Overview of Several Embodiments

Disclosed herein are embodiments of a compound having a structure satisfying Formula I or II,

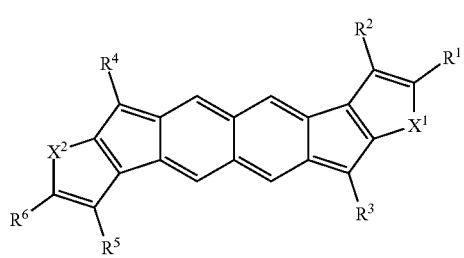

Formula I

56
-continued

Formula II wherein each of $X^1$ and $X^2$ independently are selected from S (and oxidized forms thereof, such as $SO_2$, SO, or the like), O, or NR, wherein each R independently is selected from hydrogen, aliphatic, heteroaliphatic, haloaliphatic, haloheteroaliphatic, aromatic, or an organic functional group;

each of $R^3$ and $R^4$ independently is selected from hydrogen, aliphatic, aromatic, heteroaliphatic, or an organic functional group;

each of $R^1$, $R^2$, $R^5$, and $R^6$ independently is selected from hydrogen, aliphatic, aromatic, heteroaliphatic, or an organic functional group; or $R^1$ and $R^2$ together, and/or $R^5$ and $R^6$ together, provide an aromatic ring.

In any or all of the above embodiments, each of $X^1$ and $X^2$ independently are S or $SO_2$.

In any or all of the above embodiments, each of $X^1$ and $X^2$ are S.

In any or all of the above embodiments, each of $R^3$ and $R^4$ independently are aromatic or an organic functional group.

In any or all of the above embodiments, each of $R^3$ and $R^4$ independently are aromatic, wherein the aromatic group comprises one or more substituents other than hydrogen.

In any or all of the above embodiments, the one or more substituents other than hydrogen are aliphatic, aromatic, heteroaliphatic, or an organic functional group.

In any or all of the above embodiments, each organic functional group independently is selected from a combination of an aliphatic, heteroaliphatic, aromatic, haloaliphatic, and/or haloheteroaliphatic group; or aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

In any or all of the above embodiments, each of $R^3$ and $R^4$ independently are selected from alkyl; alkynyl; alkenyl; heteroalkyl; heteroalkynyl; heteroalkenyl; phenyl; naphthyl; pyridinyl; or an organic functional group selected from benzyl, amino, halogen, nitro, alkoxy, aroxy, cyano, thiol, thioether, or hydroxyl.

In any or all of the above embodiments, $R^3$ and $R^4$ are 2,4,6-Me$_3$C$_6$H$_2$ or 2,4,6-iPr$_3$C$_6$H$_2$.

In any or all of the above embodiments, each of $R^1$, $R^2$, $R^5$, and $R^6$ independently is selected from H, amino, alkyl, alkynyl, alkenyl, heteroalkyl, heteroalkynyl, heteroalkenyl, an organic functional group; or $R^1$ and $R^2$ together provide an aryl or heteroaryl ring and/or $R^5$ and $R^6$ together provide an aryl or heteroaryl ring.

In any or all of the above embodiments, $R^1$ and $R^2$ together provide a phenyl group, a naphthyl group, an anthracenyl group, a tetracenyl group, a pentacenyl group, a phenanthrenyl group, a chrysenyl group, a pyrenyl group, or other aromatic ring system.

In any or all of the above embodiments, $R^5$ and $R^6$ together provide a phenyl group, a naphthyl group, an anthracenyl group, a tetracenyl group, a pentacenyl group, a phenanthrenyl group, a chrysenyl group, a pyrenyl group, or other aromatic ring system.

In any or all of the above embodiments, when any one or more of $R^1$, $R^2$, $R^3$, $R^4$, $R^5$, or $R^6$ are aromatic groups, the aromatic group comprises one or more substituents other than hydrogen.

In any or all of the above embodiments, one or more substituents other than hydrogen are selected from aliphatic groups, heteroaliphatic groups, aromatic groups, or an organic functional group.

In any or all of the above embodiments, the compound has a structure satisfying one or more of Formulas III or IV

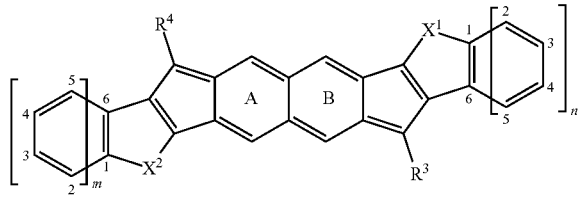

Formula III

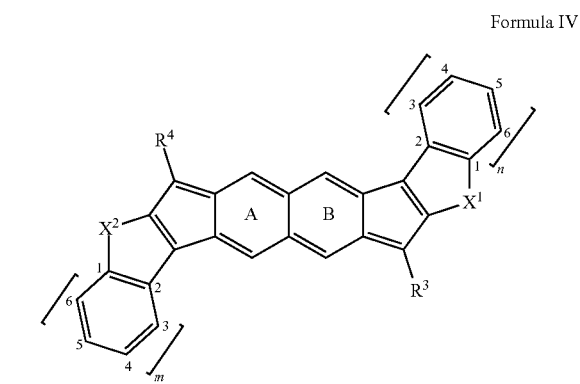

Formula IV wherein n and m independently are an integer ranging from 1 to 5.

In any or all of the above embodiments, the compound can have a structure satisfying one or more of Formula IIIA or Formula IVA

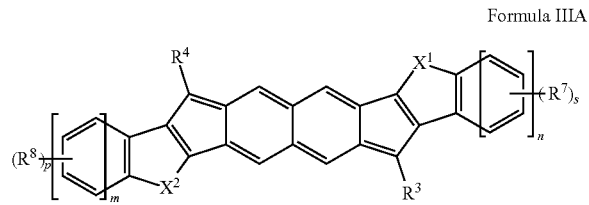

Formula IIIA

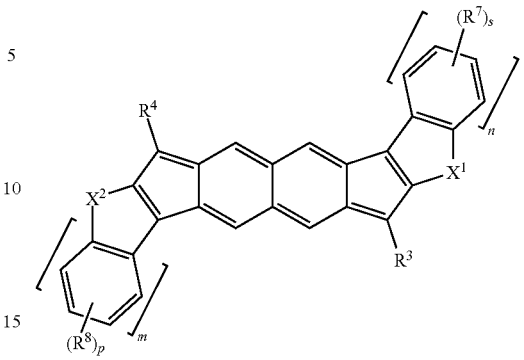

Formula IVA wherein $R^7$ and $R^8$ independently are selected from an aliphatic group, a heteroaliphatic group, an aromatic group, a haloaliphatic group, or an organic functional group;

p and s independently are an integer ranging from 1 to 12.

n and m independently are an integer ranging from 1 to 5.

In any or all of the above embodiments, each organic functional group independently is selected from a combination of an aliphatic, heteroaliphatic, aromatic, haloaliphatic, and/or haloheteroaliphatic group; or aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

In any or all of the above embodiments, the compound can have a structure according to any species disclosed herein.

Also disclosed herein are embodiments of an apparatus, comprising an electronic or electrooptical device selected from an organic light-emitting diode (OLED), an organic field-effect transistor (OFET), or an organic photovoltaic cell (OPV) and further comprising any one of the compounds according to any or all of the above embodiments.

Also disclosed herein are embodiments of a thin film, comprising a compound selected from any one of the compounds according to any or all of the above embodiments.

VI. Examples

General Procedures—

All air-sensitive manipulations were carried out under an inert atmosphere using standard Schlenk technique. For moisture sensitive reactions, THF and toluene were refluxed with Na benzophenone ketyl for 24 hours prior to distillation and use. For column chromatography, silica gel (240-300 mesh) was used. All other reagents were purchased and used as received without further purification. NMR spectra were recorded on a Bruker Avance III HD 500 equipped with a Prodigy multinuclear cryoprobe ($^1$H: 500 MHz, $^2$D: 77 MHz) or Bruker Avance III HD 600 equipped with a Prodigy multinuclear cryoprobe ($^1$H: 600 MHz, $^{13}$C: 151 MHz) NMR spectrometer at room temperature (unless otherwise noted). $^1$H and $^{13}$C NMR chemical shifts (δ) are expressed in ppm relative to the residual non-deuterated solvent reference (CDCl$_3$: $^1$H 7.26 ppm, $^{13}$C 77.16 ppm; CD$_2$Cl$_2$: $^1$H 5.32 ppm, $^{13}$C 53.84 ppm; DMSO-d$_6$: $^1$H 2.50 ppm, $^{13}$C 39.52 ppm). UV-Vis spectra were recorded on an Agilent Technologies Cary 60 UV-Vis spectrometer in HPLC grade $CH_2Cl_2$. Starting materials (e.g., compound 300 and 3-(4, 4,5,5-tetramethyl-1,3,2-dioxaborolan-2-yl)benzo[b]thiophene) were prepared according to literature procedures.

General X-Ray Data Collection—

Diffraction intensities for compound 308a were collected at 173 K on a Bruker Apex2 CCD diffractometer using CuKα radiation, λ=1.54178 Å. Space group was determined based on intensity statistics. Absorption correction was applied by SADABS.[5] Structure was solved by direct methods and Fourier techniques and refined on $F^2$ using full matrix least-squares procedures. All non-H atoms were refined with anisotropic thermal parameters. Hydrogen atoms were refined in calculated positions in a rigid group model. All calculations were performed by the Bruker SHELXL-2014 package.

Raman Spectroscopy—

Raman spectra were recorded in solid state in resonance conditions with the excitation wavelength at 785 nm in solid state. The measurements were carried in the 1×1 camera of a Bruker Senterra Raman microscope by averaging spectra during 50 min with a resolution of 3-5 $cm^{-1}$. A CCD camera operating at −50° C. was used for detection.

Example 1

Synthesis of Diester 304—

A three-neck round-bottomed flask fitted with a condenser was charged with bistriflate 300 (3.50 g, 9.2 mmol, 1 equivalent), benzothiophene 2-pinacolate ester (5.75 g, 22.1 mmol, 2.4 equivalents), $Na_2CO_3$ (12.08 g, 36.8 mmol, 4.4 equivalents), THF (80 ml) and $H_2O$ (40 ml). After bubbling $N_2$ through this mixture for 1 hour, $Pd(PPh_3)_4$ (0.0413 g, 0.184 mmol, 0.02 equivalents) was added and the reaction vessel was purged for an additional 10 minutes. After refluxing overnight and cooling to room temperature, the reaction was quenched with $H_2O$ and poured over filter paper. The precipitate was washed with $H_2O$ and MeOH to yield diester 304 as a yellow solid (4.12 g, 88%); 1H NMR (500 MHz, $CDCl_3$, 25° C.) δ (ppm) 8.35 (s, 2H), 8.12 (s, 2H), 7.88 (d, J=7.5 Hz, 2H), 7.83 (d, J=7.5 Hz, 2H), 7.42-7.35 (m, 4H), 7.36 (s, 2H) 3.81 (s, 6H); 13C NMR (151 MHz, CDCl3, 25° C.) δ (ppm) 168.52, 141.96, 140.54, 140.23, 132.67, 132.33, 132.17, 131.30, 130.51, 124.72, 124.67, 123.96, 123.42, 122.31, 52.84; high-resolution mass spectroscopy (HRMS) (ES+) (m/z), calculated for $C_{30}H_{20}O_4S_2$ $(M)^+$ 508.0803, found 508.0809.

Example 2

Synthesis of Dione 306—

A single-neck round-bottomed flask fitted with a condenser was charged with diester 304 (0.476 g, 0.936 mmol, 1 equivalent), NaOH (0.60 g, 15.0 mmol, 16 equivalents), EtOH (15 ml) and $H_2O$ (4.5 ml). After refluxing overnight, the reaction was cooled and the EtOH evaporated. Concentrated HCl was slowly added to the aqueous solution and a precipitate formed, which was isolated and washed sequentially with cold $H_2O$ and cold MeOH to yield the diacid intermediate as a yellow solid (0.373 g, 83%); 1H NMR (600 MHz, DMSO-d6, 25° C.) δ (ppm) 13.37 (s, 2H), 8.48 (s, 2H), 8.36 (s, 2H), 8.03 (d, J=7.7 Hz, 2H), 7.92 (d, J=7.2 Hz, 2H), 7.54 (s, 2H), 7.44-7.38 (m, 4H); 13C NMR (151 MHz, DMSO-d6, 25° C.) δ (ppm) 169.03, 141.58, 139.92, 139.61, 133.16, 131.99, 130.93, 130.52, 129.30, 124.73, 124.65, 123.88, 123.25, 122.29. HRMS (ES+) (m/z), calculated for $C_{28}H_{17}O_4S_2$ $(M+H)^+$ 481.0568, found 481.0569.

Three drops of DMF were added to a suspension of the diacid (0.476 g, 0.991 mmol, 1 equivalent) in $CH_2Cl_2$ (20 ml), followed by oxalyl chloride (0.34 ml, 3.96 mmol, 3.0 equivalents). After 1 hour, the volatiles were removed under reduced pressure. The crude acid chloride was dissolved in $CH_2Cl_2$ (20 ml), and solid $AlCl_3$ (0.661 g, 4.95 mmol, 5 equivalents) was added to the flask. The reaction was stirred overnight and then poured into an HCl-ice mixture, precipitating the dione. The solid was filtered and washed successively with $H_2O$, $CH_2Cl_2$ and MeOH to afford dione 306 as a purple solid that was too poorly soluble to obtain NMR spectra (0.41 g, 93%); HRMS (ES+) (m/z), calculated for $C_{28}H_{12}O_2S_2$ $(M)^+$ 444.0279, found 444.0297.

Example 3

Synthesis of 308a—

In an oven-dried round-bottomed flask, a suspension of dione 306 (0.219 g, 0.493 mmol, 1 equivalent) in dry THF (25 ml) was cooled to −78° C. under a $N_2$ atmosphere. In a separate oven-dried round-bottomed flask, 2-bromomesitylene (0.6 ml, 3.94 mmol, 8 equivalents) was dissolved in dry THF (25 ml), cooled to −78° C. under a $N_2$ atmosphere, and n-BuLi (2.5 M in hexanes, 1.47 ml, 3.69 mmol, 7.5 equivalents) was added dropwise. After stirring the mixture at −78° C. for 1 hour, the aryl lithiate was transferred via cannula to the flask containing the dione. This reaction mixture was slowly warmed to room temperature overnight with stirring. The reaction was then quenched with a saturated aqueous $NH_4Cl$ solution and extracted with $Et_2O$ (3 times). The combined organic layer was washed with brine, dried ($MgSO_4$) and concentrated in vacuo. The resulting crude oil was passed through a silica plug eluting with hexanes, followed by a $CH_2Cl_2$ wash, to provide the desired diol, which was carried on to the reductive dearomatization step without further purification.

In a single-neck round-bottomed flask the crude diol (0.05 g, 0.073 mmol, 1 equivalent) and anhydrous $SnCl_2$ (33 mg, 0.175 mmol, 4 equivalents) were dissolved in dry degassed toluene (15 ml). Trifluoroacetic acid (catalytic) was added and this mixture was then vigorously stirred. The reaction was monitored via thin-layer chromatography (9:1 hexanes/$CH_2Cl_2$). After 3 hours, the mixture was poured over a silica plug and washed with hexanes. Switching to 1:1 hexanes/$CH_2Cl_2$ eluted the product. The solvent was evaporated and the solid was washed with cold MeCN to remove trace impurities. The remaining solid was redissolved in $CHCl_3$ and MeCN was layered over the solution to furnish compound 308a as deep purple crystals (0.199 g, 62% from 306); 1H NMR (500 MHz, CDCl3, 25° C.) δ (ppm) 7.62 (d, J=8.0 Hz, 2H), 7.17 (s, 2H), 7.16 (t, J=8.1 Hz, 2H), 7.08 (t, J=7.6 Hz, 2H), 7.03 (s, 4H), 6.91 (d, J=7.7 Hz, 2H), 6.84 (s, 2H), 2.41 (s, 6H), 2.20 (s, 12H); 13C NMR (151 MHz, $CDCl_3$, 25° C.) δ (ppm) 148.22, 147.56, 145.45, 141.61, 141.07, 140.60, 139.95, 135.80, 134.75, 133.71, 133.29, 133.09, 131.43, 130.27, 128.60, 128.29, 126.89, 125.00, 32.81, 23.59; HRMS (ES+) (m/z), calculated for $C_{46}H_{35}S_2$ $(M+H)^+$ 651.2180, found 651.2184.

Example 4

Synthesis of 308b—

Following the procedure for compound 308a, dione 306 (0.130 g, 0.292 mmol, 1 equivalent) and 1-bromo-2,4,6-triisopropylbenzene (0.59 ml, 2.34 mmol, 8 equivalents)

were reacted to yield crude diol. Diol (0.062 g, 0.073 mmol, 1 equivalent) and $SnCl_2$ (55 mg, 0.291 mmol, 4 equiv) were reacted. After 4 hours, the mixture was poured over a silica plug and washed with hexanes. Switching to 1:1 hexanes/$CH_2Cl_2$ eluted the product. The solvent was evaporated and the solid was washed with cold MeCN to remove trace impurities. The remaining solid was redissolved in $CHCl_3$ and MeCN was layered over the solution to furnish 308b as deep blue crystals (0.024 g, 12% from 306); $^1H$ NMR (500 MHz, $CDCl_3$, 25° C.) δ (ppm) 7.60 (d, J=8.1 Hz, 2H), 7.21 (s, 2H), 7.15-7.12 (m, 6H), 7.04 (t, J=7.1 Hz, 2H), 6.89 (s, 2H), 6.82 (d, J=7.9 Hz, 2H), 3.06-2.99 (m, 6H), 1.37 (d, J=6.9 Hz, 12H), 1.13 (d, J=6.8 Hz, 12H), 1.01 (d, J=6.8 Hz, 12H); $^{13}C$ NMR (151 MHz, $CDCl_3$, 25° C.) δ (ppm) 148.96, 147.70, 146.12, 144.62, 141.74, 139.73, 138.45, 132.74, 131.26, 130.53, 129.91, 128.09, 127.42, 125.09, 124.94, 123.70, 122.05, 120.75, 34.28, 31.30, 24.81, 24.14, 24.09; HRMS ($ES^+$) (m/z) calculated for $C_{58}H_{59}S_2$ $(M+H)^+$ 819.4058, found 819.4086.

Example 5

Synthesis of 308c—

Following the procedure for 308a, dione 306 (0.130 g, 0.292 mmol, 1 equivalent) and 1-bromo-4-tert-butylbenzene (0.40 ml, 2.336 mmol, 8 equivalents) were reacted to yield the crude diol. Diol (0.025 g, 0.035 mmol, 1 equivalent) and $SnCl_2$ (30 mg, 0.140 mmol, 4 equiv) were reacted at 70° C. After 4 hours, the mixture was poured over a silica plug and washed with hexanes. Switching to 4:1 hexanes/$CH_2Cl_2$ eluted the product. In some embodiments, the dihydro product was obtained and further purified using flash column chromatography using 7:3 hexanes/$CH_2Cl_2$ as eluent to furnish 308c$H_2$ as a tan solid (121 mg, 61% from 14); $^1H$ NMR (500 MHz, $CD_2Cl_2$, 25° C.) δ (ppm) 7.89 (d, J=7.8 Hz, 2H), 7.83 (s, 2H), 7.72 (s, 2H), 7.43 (d, J=7.4 Hz, 2H), 7.32 (d, J=8.3 Hz, 4H), 7.29-7.21 (m, 4H), 7.13 (d, J=8.4 Hz, 4H), 5.22 (s, 2H), 1.28 (s, 18H); $^{13}C$ NMR (151 MHz, $CD_2Cl_2$, 25° C.) δ (ppm) 150.45, 150.29, 146.79, 144.85, 143.27, 137.31, 136.84, 135.09, 132.76, 127.99, 126.17, 125.07, 124.73, 124.27, 124.12, 122.29, 118.01, 51.20, 34.77, 31.48; HRMS ($ES^+$) (m/z) calculated for $C_{48}H_{40}S_2$ $(M+H)^+$ 680.2572, found 680.2539.

Example 6

Synthesis of 308d—

Following the procedure described above for 308a, dione 306 (0.140 g, 0.32 mmol, 1 equivalent) and 2-bromo-5-t-butyl-1,3-dimethylbenzene (0.608 g, 2.52 mmol, 8 equivalents), and n-BuLi (1.6 M in hexanes, 1.50 mL, 2.36 mmol, 7.5 equivalents) were reacted to give the crude diol. Dearomatization of the crude diol (0.201 g, 0.261 mmol, 1 equivalent) with anhydrous $SnCl_2$ (0.198 g, 1.05 mmol, 4 equivalents) gave a deep green solution which was reacted for 4 h and then filtered through a pad of celite. The filtrate was concentrated, triturated with MeCN, and filtered to yield 308d (0.074 g, 42% from anti-dione) as a deep green solid. $^1H$ NMR (500 MHz, $CD_2Cl_2$, 25° C.) δ (ppm) 7.61 (d, J=7.7 Hz, 2H), 7.24-7.13 (m, overlapping singlets and a triplet, 8H), 7.08 (s, 2H), 6.92 (d, J=7.8 Hz, 2H), 6.86 (s, 2H), 2.23 (s, 12H), 1.41 (s, 18H); $^{13}C$ NMR (126 MHz, $CD_2Cl_2$, 25° C.) δ (ppm) 150.94, 145.30, 144.75, 142.54, 138.76, 138.25, 136.66, 133.00, 131.87, 130.93, 130.59, 130.18, 127.59, 125.54, 125.21, 124.64, 123.88, 122.07, 34.65, 31.62, 20.96; HRMS (ASAP) (m/z) calculated for $C_{52}H_{47}S_2$ (M+H)+ 735.3119, found 735.3076.

Example 7

Synthesis of Dideutero 308c$D_2$.

Following the procedure for 308a, dione 14 (0.130 g, 0.292 mmol, 1 equivalent) and 1-bromo-4-tert-butylbenzene (0.40 ml, 2.336 mmol, 8 equivalents) were reacted to yield the crude diol. Diol (0.025 g, 0.035 mmol, 1 equivalent), $SnCl_2$ (30 mg, 0.140 mmol, 4 equiv) and 0.1 ml of $D_2O$ were reacted at 70° C. After 4 hours, the mixture was poured over a silica plug and washed with hexanes. Switching to 4:1 hexanes/$CH_2Cl_2$ eluted the product. The dideutero product was further purified using flash column chromatography using 7:3 hexanes/$CH_2Cl_2$ as eluent to furnish 308c$D_2$ as an off yellow solid (113 mg, 57% from 14); $^1H$ NMR (600 MHz, $CD_2Cl_2$, 25° C.) δ (ppm) 7.89 (d, J=7.9 Hz, 2H), 7.82 (s, 2H), 7.70 (s, 2H), 7.42 (d, J=7.8 Hz, 2H), 7.31 (d, J=8.1 Hz, 4H), 7.28 (t, J=7.1 Hz, 2H), 7.24 (t, J=7.2 Hz, 2H), 7.12 (d, J=8.0 Hz, 4H), 1.29 (s, 18H); $^2D$ NMR (77 MHz, $CDCl_3$, 25° C.) δ (ppm) 5.16 (s); $^{13}C$ NMR (151 MHz, $CD_2Cl_2$, 25° C.) δ (ppm) 150.42, 150.21, 146.74, 144.84, 143.30, 137.32, 136.83, 135.09, 132.74, 127.99, 126.15, 125.05, 124.71, 124.25, 124.09, 122.27, 117.98, 51.17, 34.76, 31.53; HRMS ($EI^+$) (m/z) calculated for $C_{48}H_{38}D_2S_2$ 682.2697, found 682.2704.

Example 8

Synthesis of Diester 402—

A two-neck round-bottom flask fitted with a condenser was charged with bistriflate 300 (0.500 g, 0.925 mmol, 1 equivalent), benzothiophene 3-pinacolate ester (0.601 g, 2.31 mmol, 2.5 equivalentz), $K_3PO_4$ (0.589 g, 2.78 mmol, 3 equivalents), Pd(OAc)$_2$ (8.3 mg, 0.037 mmol, 0.04 equivalents), and SPhos (30.4 mg, 0.074 mmol, 0.08 equivalents). These solids were then placed under $N_2$ atmosphere and dissolved in 40:1 toluene/$H_2O$ (41 mL) that had been sparged with $N_2$ for 1.5 hr. After refluxing overnight and cooling to room temperature, the reaction was quenched with $H_2O$ and poured over filter paper. The precipitate was washed with $H_2O$ and MeOH to yield diester 402 as a yellow solid (409 mg, 87%); $^1H$ NMR (500 MHz, $CDCl_3$, 25° C.) δ 8.54 (s, 2H), 8.09 (s, 2H), 7.94 (d, J=8.0 Hz, 2H), 7.51 (d, J=7.8 Hz, 2H), 7.46 (s, 2H), 7.39 (t, J=7.3 Hz, 2H), 7.35 (t, J=7.4 Hz, 2H), 3.53 (s, 6H); $^{13}C$ NMR (151 MHz, $CDCl_3$, 25° C.) δ (ppm) 168.02, 139.82, 139.21, 136.80, 133.61, 133.24, 132.05, 131.58, 131.07, 124.58, 123.93, 123.02, 122.32, 52.50; high-resolution mass spectroscopy (HRMS) ($ES^+$) (m/z), calculated for $C_{30}H_{20}O_4NaS_2$ $(M+Na)^+$ 531.0701, found 531.0654.

Example 9

Synthesis of Dione 404—

A single neck round bottomed flask fitted with a condenser was charged with diester 402 (0.400 g, 0.786 mmol, 1 equivalent), KOH (0.706 g, 12.6 mmol, 16 equivalents), EtOH (60 ml), and $H_2O$ (15 ml). After refluxing the flask overnight, the reaction was cooled and the EtOH evaporated. Concentrated HCl was slowly added to the aqueous solution and a precipitate formed, which was isolated and washed with $H_2O$ to yield the diacid intermediate as a yellow solid that was carried on without further purification.

To a suspension of the diacid (0.345 g, 0.718 mmol, 1 equivalent) in $CH_2Cl_2$ (40 ml) was added 3 drops of DMF followed by oxalyl chloride (0.24 ml, 2.87 mmol, 4.0 equivalents). After 12 hours, the volatiles were removed under reduced pressure. The crude acid chloride was dissolved in CH$_2$Cl$_2$ (40 ml) and solid AlCl$_3$ (0.479 g, 3.59 mmol, 5 equivalents) was added to the flask. The reaction was stirred overnight and then poured into an HCl-ice mixture, precipitating the dione. The solid was filtered and washed successively with H$_2$O, CH$_2$Cl$_2$ and acetone to afford dione 404 as a purple solid that was too poorly soluble to obtain NMR spectra (0.302 g, 88%); HRMS (ES$^+$) (m/z), calculated for C$_{28}$H$_{13}$O$_2$S$_2$ (M+H)$^+$ 445.0351, found 445.0352.

Example 10

Synthesis of 406a—

In an oven-dried round bottom flask, a suspension of dione 404 (0.200 g, 0.450 mmol, 1 equivalent) in dry THF (20 ml) was cooled to −78° C. under a N$_2$ atmosphere. In a separate oven-dried round bottom flask, 2-bromomesitylene (0.690 mL, 4.6 mmol, 10 equivalents) was dissolved in dry THF (20 ml), cooled to −78° C. under a N$_2$ atmosphere, and n-BuLi (2.5 M in hexanes, 1.76 ml, 4.41 mmol, 9.8 equivalents) was added dropwise. After stirring the mixture at −78° C. for 1 hour, the aryl lithiate was transferred via cannula to the flask containing the dione. This reaction mixture was stirred for 4 hours at −78° C., then slowly warmed to room temperature overnight with stirring. The reaction was then quenched with a saturated aqueous NH$_4$Cl solution and extracted with CH$_2$Cl$_2$ (3×). The combined organic layer was washed with brine, dried (MgSO$_4$) and concentrated in vacuo. The resulting crude oil was passed through a silica plug eluting with hexanes, followed by a CH$_2$Cl$_2$ wash, to provide the desired diol that was carried onto the reductive dearomatization step without further purification.

Figure 2A:
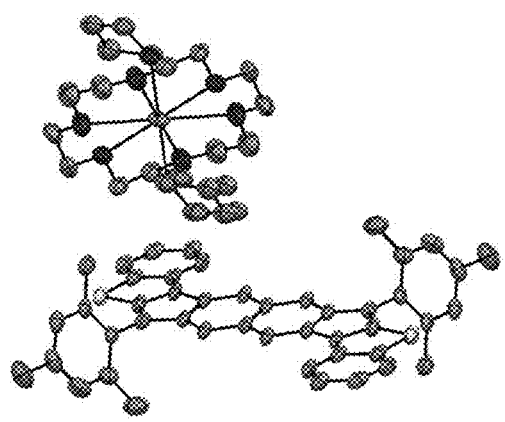
FIGS. 2A and 2B illustrate crystal structures of the mono-anion complex of compound 406a (FIG. 2A) and the di-anion complex of compound 406a (FIG. 2B).
Figure 2B:
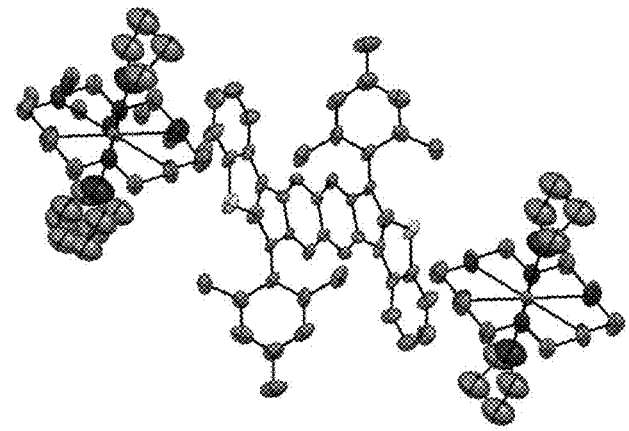

In a single-neck round-bottom flask the crude diol (0.300 g, 0.44 mmol, 1 equivalent) and anhydrous SnCl$_2$ (332 mg, 1.8 mmol, 4 equivalents) were dissolved in dry degassed toluene (60 ml). Trifluoroacetic acid (5 drops) was added and this mixture was then vigorously stirred. The reaction was monitored via TLC (9:1 hexanes/CH$_2$Cl$_2$). After 3 hours, the mixture was poured over a silica plug and washed with hexanes. Switching to 1:1 hexanes/CH$_2$Cl$_2$ eluted the product. The solvent was evaporated and the solid was washed with cold MeCN to remove trace impurities. The remaining solid was redissolved in CHCl$_3$ and MeCN was layered over the solution to furnish 406a as deep green crystals (0.270 mg, 92% from 404); $^1$H NMR (500 MHz, CDCl$_3$, 25° C.) δ (ppm) 7.71 (d, J=7.9 Hz, 2H), 7.55 (d, J=8.0 Hz, 2H), 7.27-7.23 (m, 2H), 7.17-7.13 (m, 4H), 6.99 (s, 4H), 6.64 (s, 2H), 2.37 (s, 6H), 2.28 (s, 12H); HRMS (ES$^+$) (m/z), calculated for C$_{46}$H$_{35}$S$_2$ (M+H)$^+$651.2175, found 651.2174. The UV-Vis spectrum of compound 406a is provided by FIG. 1 and crystal structures of the mono and di-anions of compound 406a are provided by FIGS. 2A and 2B, respectively.

Compounds 406b and 406c can be obtained using a similar procedure with the appropriate aryl lithium species as illustrated in Scheme 4. And, in some embodiments, the dihydro product 406cH$_2$ was obtained.

Example 11

Synthesis of 500—

A flame-dried single-neck round bottom flask was charged with 4-tert-butyl-2,6-dimethyl-bromobenzene, (0.82 g, 3.37 mmol, 6 equivalents) which was prepared according to literature, along with 10 mL of dry THF was added to the flask which was then cooled to −78° C. Once at temperature, n-BuLi (1.9 mL, 3.09 mmol, 5.5 equivalents) was added dropwise and the organo-lithiate was then allowed to stir at −78° C. for 1 hour. Meanwhile in a separate flame-dried round bottom flask a suspension of dione 404 (0.25 g, 0.56 mmol, 1 equivalent in 20 mL dry THF) was also cooled to −78° C. After 1 hour, the organo-lithiate was transferred via cannula to the flask containing the dione 404. The reaction was allowed to gradually warm to room temperature overnight. The reaction was quenched with saturated NH$_4$Cl solution and the organics were extracted (3×) with DCM. The combined organic layer was then washed with H$_2$O and brine, dried with MgSO$_4$ and concentrated in vacuo. A plug was run to quickly purify the resulting diols and then carried onto the reductive dearomatization without further purification or characterization.

In a single-neck round-bottom flask the crude diol (1 equivalent) and anhydrous SnCl$_2$ (0.39 g, 4 equivalents) were dissolved in 45 mL dry toluene. Trifluoroacetic acid (3 drops, catalytic) was added to the mixture which was then stirred for 4 hours. The reaction was monitored via TLC (9:1 hexanes/DCM). Once the reaction was completed, the reaction mixture was concentrated ~10 mL and then poured over a silica plug where a 50% hexanes/DCM eluent was used to collect the crude reduced compounds. Upon completion of the initial plug a column was run using 10% DCM/Hexanes, followed by preparatory TLC using 25% DCM/Hexanes as the eluent to isolate 500 (149 mg, 36% from the dione) as a green solid. NMR spectra and mass spec. match previously reported compound. $^1$H NMR (600 MHz, CD$_2$Cl$_2$, 25° C.) δ 7.74 (d, J=6.8 Hz, 2H), 7.58 (d, J=8.0 Hz, 2H), 7.30-7.26 (m, 2H), 7.23-7.16 (m, 8H), 6.67 (s, 2H), 2.31 (s, 12H), 1.38 (s, 18H); $^{13}$C NMR (126 MHz, CD$_2$Cl$_2$, 25° C.) δ (ppm) 151.20, 147.70, 146.77, 140.84, 140.04, 138.98, 136.47, 133.37, 132.35, 131.93, 129.76, 129.22, 128.29, 125.57, 125.35, 124.70, 123.99, 122.21, 34.36, 31.09, 20.56; HRMS (ASAP) (m/z) calculated for C$_{52}$H$_{47}$S$_2$ (M+H)+ 735.3119, found 735.3119.

Synthesis of 502.

Figure 3:
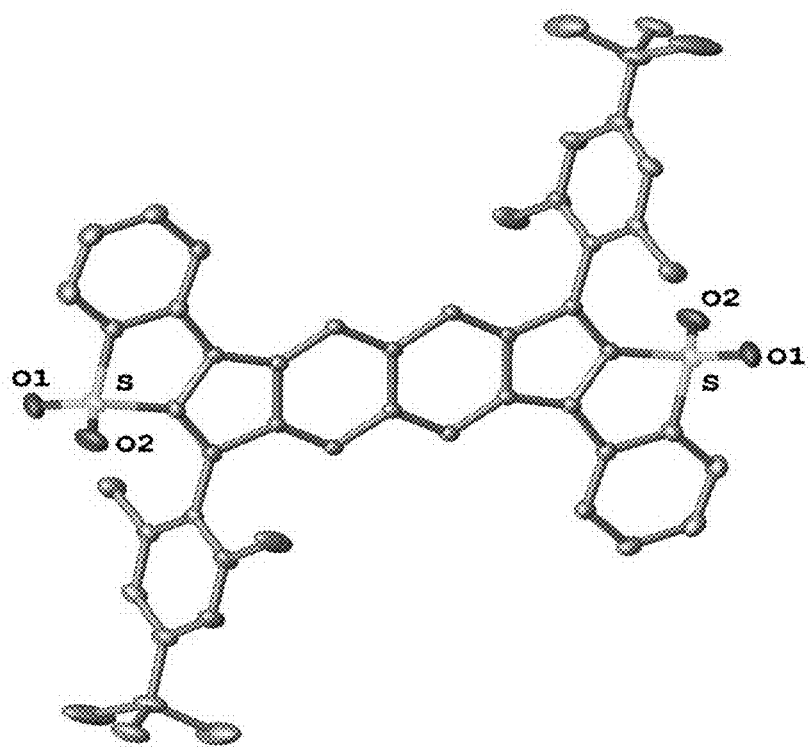
FIG. 3 illustrates the crystal structure of compound 502.

A flame-dried single-neck round bottom flask equipped with a Claisen head was charged with fully conjugated reduced 500 (0.11 g, 0.15 mmol 1 equivalent) and 20 ml of dry DCM. To this m-CPBA (0.21 g, 1.21 mmol, equivalent) was added in 3 portions over a 30 minute period and the reaction was wrapped in foil. The reaction was left to stir at room temperature for 21 hours. The reaction was then quenched with a 10% KOH solution and the organics were extracted using (3×) DCM. The combined organic layers were washed with brine, and dried (MgSO$_4$) and then concentrated to dryness. The desired sulfone was purified by flash column chromatography using 60% DCM/Hexanes as the eluent. Compound 502 was isolated as a greyish-purple solid (58 mg, 48%). $^1$H NMR (500 MHz, Chloroform-d) δ 7.83 (s, 2H), 7.76-7.73 (m (overlapping doublets), 4H), 7.58 (td, J=7.7, 1.1 Hz, 2H), 7.48 (t, J=7.4 Hz, 2H), 7.24 (s, 2H), 7.16 (s, 4H), 2.29 (s, 12H), 1.38 (s, 18H). $^{13}$C NMR (151 MHz, CDCl$_3$) δ 152.13, 145.83, 142.26, 142.11, 141.40, 140.14, 136.85, 136.52, 135.41, 133.82, 131.05, 130.17, 130.04, 127.40, 127.05, 124.96, 124.00, 123.03, 34.90, 31.73, 21.03. high-resolution mass spectroscopy HRMS (TOF ES$^+$) (m/z), calculated for C$_{52}$H$_{46}$O$_4$S$_2$ (M)$^+$ 798.2838 found 798.2831. FIG. 3 shows the x-ray diffraction image obtained for compound 502.

Example 12

Synthesis of 600—

A two-neck round-bottom flask fitted with a condenser was charged with bistriflate 300 (0.350 g, 0.647 mmol, 1 equivalent), 3-benzofuranboronic acid (0.230 g, 1.42 mmol, 2.2 equivalents), K$_3$PO$_4$ (0.343 g, 1.62 mmol, 2.5 equivalents), Pd(OAc)$_2$ (6 mg, 0.026 mmol, 0.04 equivalents), and SPhos (21 mg, 0.052 mmol, 0.08 equivalents). These solids were then placed under $N_2$ atmosphere and dissolved in 40:1 toluene/$H_2O$ (41 mL) that had been sparged with $N_2$ for 1 hour. After refluxing overnight and cooling to room temperature, the reaction was quenched with $H_2O$, extracted with dichlormethane (3×30 mL), washed with brine (1×), dried over $MgSO_4$ and filtered. The filtrate was concentrated to yield 600 as a pale yellow solid (270 mg, 88%); $^1H$ NMR (500 MHz, $CDCl_3$, 25° C.) δ 8.50 (s, 2H), 8.09 (s, 2H), 7.82 (s, 2H), 7.59 (d, J=8.3 Hz, 2H), 7.46 (d, J=7.7 Hz, 2H), 7.36 (t, J=7.7 Hz, 2H), 7.28 (t overlapping with solvent peak, J=7.8 Hz, 2H), 3.65 (s, 6H); $^{13}C$ NMR (151 MHz, $CDCl_3$, 25° C.) (ppm) 168.29, 155.19, 142.15, 133.14, 131.87, 131.21, 131.03, 129.12, 127.95, 124.75, 123.20, 121.50, 119.85, 111.96, 52.59.

Synthesis of 602—

A single neck round bottomed flask fitted with a condenser was charged with diester 600 (0.270 g, 0.567 mmol, 1 equivalent), KOH (0.317 g, 5.67 mmol, 10 equivalents), EtOH (40 ml), and $H_2O$ (10 ml). After refluxing the flask overnight, the reaction was cooled and the EtOH evaporated. Concentrated HCl was slowly added to the aqueous solution and a precipitate formed, which was isolated and washed with $H_2O$ to yield the diacid intermediate as a yellow solid that was carried on without further purification.

To a suspension of the diacid (0.210 g, 0.470 mmol, 1 equivalent) in $CH_2Cl_2$ (60 ml) was added 3 drops of DMF followed by oxalyl chloride (0.16 ml, 1.87 mmol, 4.0 equivalents). After 12 hours, the volatiles were removed under reduced pressure. The crude acid chloride was dissolved in $CH_2Cl_2$ (40 ml) and solid $AlCl_3$ (0.312 g, 2.34 mmol, 5 equivalents) was added to the flask. The reaction was stirred overnight and then poured into an HCl-ice mixture, precipitating the dione. The solid was filtered and washed successively with $H_2O$, $CH_2Cl_2$ and acetone to afford dione 602 as a brown solid that was too poorly soluble to obtain NMR spectra (0.115 g, 50%, two steps);

Synthesis of 604—

In an oven-dried round bottom flask, a suspension of dione 602 (0.306 g, 0.742 mmol, 1 equivalent) in dry THF (30 ml) was cooled to −78° C. under a $N_2$ atmosphere. In a separate oven-dried round bottom flask, 2-bromo-5-tert-butyl-m-xylene (1.420 g, 5.90 mmol, 8 equivalents) was dissolved in dry THF (30 ml), cooled to −78° C. under a $N_2$ atmosphere, and n-BuLi (2.5 M in hexanes, 2.23 ml, 5.56 mmol, 7.5 equivalents) was added dropwise. After stirring the mixture at −78° C. for 1 hour, the aryl lithiate was transferred via cannula to the flask containing the dione. This reaction mixture was stirred for 4 hours at −78° C., then slowly warmed to room temperature overnight with stirring. The reaction was then quenched with a saturated aq. $NH_4Cl$ solution and extracted with $CH_2Cl_2$ (3×). The combined organic layer was washed with brine, dried ($MgSO_4$) and concentrated in vacuo. The resulting crude residue was passed through a silica plug eluting with hexanes, followed by a $CH_2Cl_2$ wash, to provide the desired diol that was carried onto the reductive dearomatization step without further purification.

Figure 4:
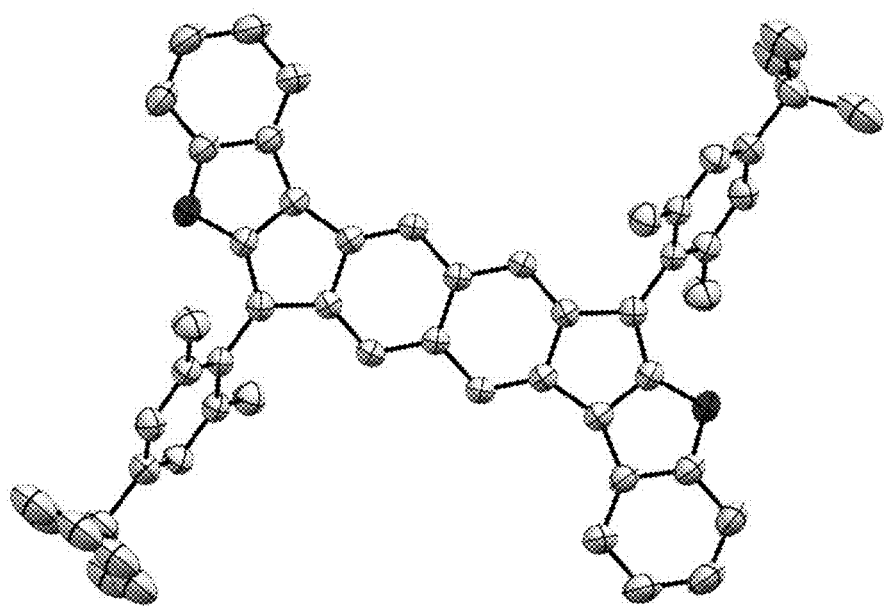
FIG. 4 illustrates the crystal structure of compound 604.
Figure 5A:
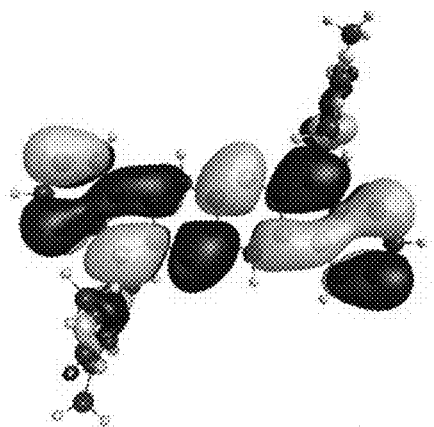
FIGS. 5A and 5B illustrate and compare the spatial distributions of the HOMO wavefunctions for 7,14-dimesitylfluoreno[3,2-b]fluorene (FIG. 5A) and compound 308a (FIG. 5B) calculated at the tuned-LC-RBLYP/6-311G(d) level of theory (isosurface value of 0.01 a.u.).
Figure 5B:
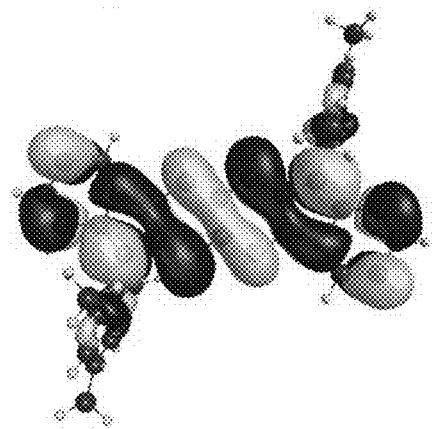
Figure 6A:
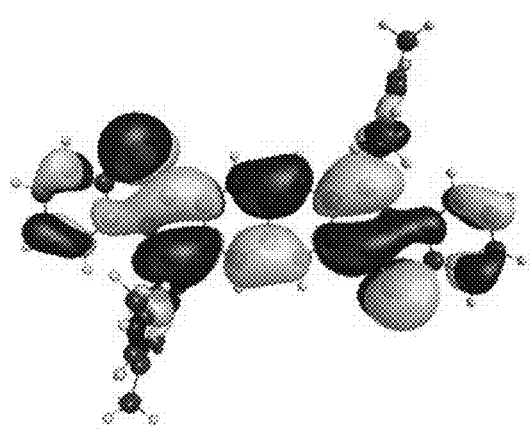
FIGS. 6A and 6B illustrate and compare the spatial distributions of the LUMO wavefunctions for 7,14-dimesitylfluoreno[3,2-b]fluorene (FIG. 6A) and compound 308a (FIG. 6B) calculated at the tuned-LC-RBLYP/6-311G(d) level of theory (isosurface value of 0.01 a.u.).
Figure 6B:
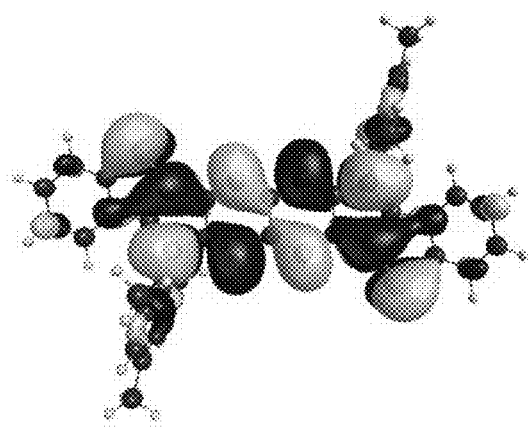

In a single-neck round-bottom flask the crude diol (0.261 g, 0.340 mmol, 1 equivalent) and anhydrous $SnCl_2$ (0.262 g, 1.42 mmol, 4 equivalents) were dissolved in dry degassed toluene (60 ml). Trifluoroacetic acid (5 drops) was added and this mixture was then vigorously stirred. The reaction was monitored via TLC (9:1 hexanes/$CH_2Cl_2$). After 3 hours, the solvent was evaporated and the solid was washed with cold MeCN to remove trace impurities. The remaining solid was redissolved in $CHCl_3$ and MeCN was layered over the solution to furnish compound 604 as a deep green solid (0.114 mg, 48% from 602). A portion of this green solid was dissolved in 5:1 $CHCl_3/CH_3CN$ and allowed to evaporate slowly yielding crystals suitable for X-ray diffraction (see FIG. 4).

Example 13

In this example, the theoretically estimated y and $\Delta E_{S-T}$ values of 6,12-dimesitylindeno[1,2-b]fluorene, 7,14-dimesitylfluoreno[3,2-b]fluorene, and 8,16-dimesityldiindeno[1,2-b:1',2'-i]anthracene were compared with those of compound 308a and comparison compounds 310 and 312, having structures illustrated below.

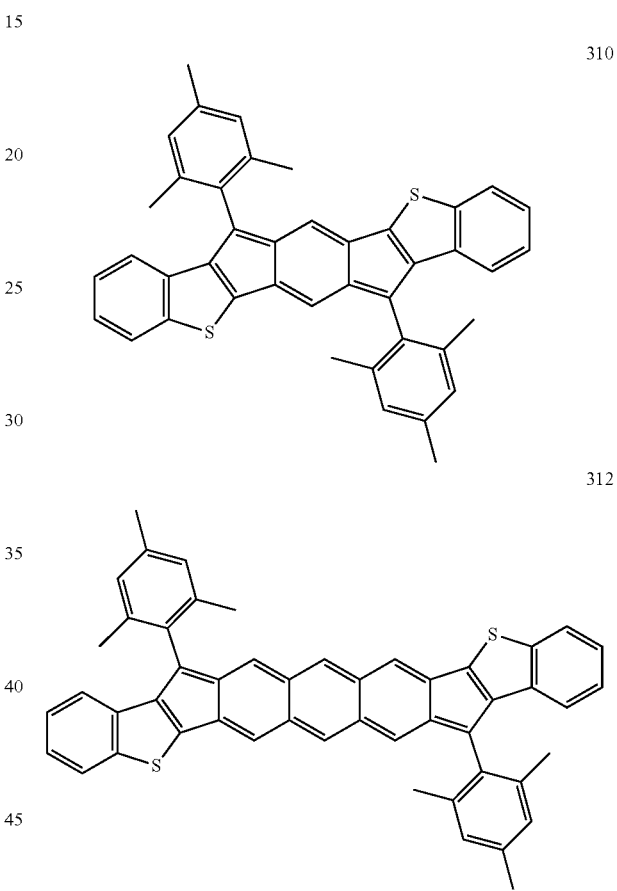

Geometry optimizations for the singlet compounds were performed at the RB3LYP/6-311G(d) level of approximation, the use of which has been reported to reproduce well the experimental geometries of diradical PAHs involving five-membered rings. Selected C—C bond lengths of the RB3LYP geometries for the present compounds are in good agreement with the experimentally available results (Tables 2-4, wherein only the carbon skeleton of the compounds are illustrated without double bonds for simplicity only). Interestingly, the lengths of bond 1 of compounds 308a, 310, and 312 (1.41-1.42 Å, Tables 2-4) are elongated compared to those of 6,12-dimesitylindeno[1,2-b]fluorene, 7,14-dimesitylfluoreno[3,2-b]fluorene, and 8,16-dimesityldiindeno[1,2-b:1',2'-i]anthracene (1.38-1.39 Å), indicating that the contribution of the diradical form becomes larger in thiophene-containing compounds 308a, 310, and 312 than in the purely hydrocarbon counterpart 6,12-dimesitylindeno[1,2-b]fluorene, 7,14-dimesitylfluoreno[3,2-b]fluorene, and 8,16-dimesityldiindeno[1,2-b:1',2'-i]anthracene.

TABLE 2

Comparison of bond lengths (Å) of selected bonds between 6,12-dimesitylindeno[1,2-b]fluorene and 310.

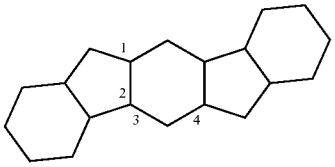 [SMILES: C1CCC2C(C1)CC1CC3C(CC4CCCCC43)CC12]

| 6,12-dimesitylindeno[1,2-b]fluorene | | 310 | |
|---|---|---|---|
| Bond | RB3LYP | Expt. | |
| 1 | 1.381 | 1.380(2) | |
| 2 | 1.466 | 1.467(2) | |
| 3 | 1.360 | 1.356(2) | |
| 4 | 1.434 | 1.433(3) | |

| Bond | RB3LYP | Expt. |
|---|---|---|
| 1 | 1.410 | 1.409(3) |
| 2 | 1.460 | 1.457(3) |
| 3 | 1.378 | 1.377(3) |
| 4 | 1.412 | 1.412(3) |

TABLE 3

Comparison of bond lengths (Å) of selected bonds between 7,14-dimesitylfluoreno[3,2-b]fluorene and 308a.

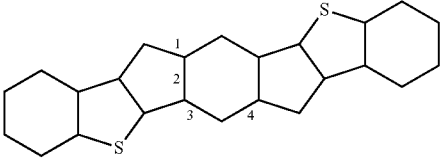 [SMILES: C1CCC2C(C1)SC1C3CC4CC5C6CCCCC6SC5C4CC3CC21]

| 7,14-dimesitylfluoreno[3,2-b]fluorene | | | | 308a | | |
|---|---|---|---|---|---|---|
| Bond | RB3LYP | UB3LYP | Expt. | RB3LYP | UB3LYP | Expt. |
| 1 | 1.389 | 1.397 | — | 1.419 | 1.430 | 1.424(4) |
| 2 | 1.462 | 1.458 | — | 1.465 | 1.461 | 1.463(3) |
| 3 | 1.357 | 1.360 | — | 1.375 | 1.375 | 1.364(4) |
| 4 | 1.441 | 1.438 | — | 1.420 | 1.420 | 1.420(4) |
| 5 | 1.381 | 1.387 | — | 1.403 | 1.410 | 1.398(4) |
| 6 | 1.417 | 1.411 | — | 1.392 | 1.387 | 1.387(4) |
| 7 | 1.465 | 1.460 | — | 1.456 | 1.451 | 1.457(5) |

TABLE 4

Comparison of bond lengths (Å) of selected bonds between 8,16-dimesityldiindeno[1,2-b:1',2'-i]anthracene and 312.

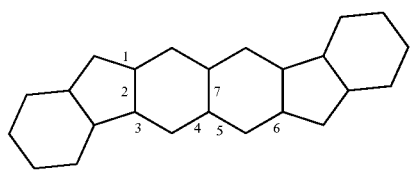 [SMILES: C1CCC2C(C1)CC1CC3CC4C(CC3CC12)CC1CCCCC14]

| 8,16-dimesityldiindeno[1,2-b:1',2'-i]anthracene | | | | 312 | | |
|---|---|---|---|---|---|---|
| Bond | RB3LYP | UB3LYP | Expt. | RB3LYP | UB3LYP | Expt. |
| 1 | 1.393 | 1.412 | 1.406(3) | 1.419 | 1.435 | — |
| 2 | 1.465 | 1.460 | 1.460(3) | 1.474 | 1.469 | — |
| 3 | 1.357 | 1.360 | 1.359(3) | 1.373 | 1.371 | — |
| 4 | 1.441 | 1.437 | 1.447(3) | 1.422 | 1.426 | — |
| 5 | 1.376 | 1.387 | 1.403(3) | 1.393 | 1.396 | — |
| 6 | 1.425 | 1.413 | 1.446(3) | 1.406 | 1.402 | — |
| 7 | 1.388 | 1.406 | 1.399(3) | 1.408 | 1.420 | — |

TABLE 4-continued

Comparison of bond lengths (Å) of selected bonds between 8,16-dimesyldiindeno[1,2-b:1',2'-i]anthracene and 312.

8,16-dimesityldiindeno[1,2-b:1',2'-i]anthracene

| Bond | RB3LYP | UB3LYP | Expt. |
|---|---|---|---|
| 8 | 1.411 | 1.397 | 1.416(3) |
| 9 | 1.461 | 1.453 | 1.461(3) |

312

| Bond | RB3LYP | UB3LYP | Expt. |
|---|---|---|---|
| 8 | 1.388 | 1.379 | — |
| 9 | 1.457 | 1.451 | — |

The y values calculated at the PUHF/6-311G(d) level are summarized in Table 5. For both series (6,12-dimesitylindeno[1,2-b]fluorene, 7,14-dimesitylfluoreno[3,2-b]fluorene, and 8,16-dimesityldiindeno[1,2-b:1',2'-i]anthracen; and compounds 308a, 310, and 312), the y values increase with elongation of the central core. Concomitantly to the bond 1 lengthening behavior, compounds 308a, 310, and 312 have larger y values than 6,12-dimesitylindeno[1,2-b]fluorene, 7,14-dimesitylfluoreno[3,2-b]fluorene, and 8,16-dimesityl-diindeno[1,2-b:1',2'-i]anthracene. Geometry optimizations also were performed for the triplet compounds at the UB3LYP/6-311G(d) level, and the adiabatic $\Delta E_{S-T}$ gaps were estimated at the spin-flip non-collinear time-dependent density functional theory (SF-NC-TDDFT) with PBE50 functional using the 6-311G(d) basis set (Table 5). $\Delta E_{S-T}$ decreases with increasing y with all the examined compounds possessing singlet ground states. Additional comparison results are provided in Tables 6 and 7.

TABLE 5

Theoretically estimated y and $\Delta E_{S-T}$ values of compounds

| Compound | y for singlet state (—) | Adiabatic $\Delta E_{S-T}$ (kcal mol$^{-1}$)$^a$ |
|---|---|---|
| 6,12-dimesitylindeno[1,2-b]fluorene | 0.30 | −19.4 |
| 7,14-dimesitylfluoreno[3,2-b]fluorene | 0.49 | −10.3 |
| 8,16-dimesityldiindeno[1,2-b: 1',2'-i]anthracene | 0.62 | −5.4 |
| 310 | 0.41 | −15.38 |
| 308a | 0.61 | −8.8 |
| 312 | 0.74 | −4.4 |

TABLE 6

Comparison of S-T energy gaps (kcal mol$^{-1}$) calculated by different methods.

| Compound | Tuned-LC-RBLYP CASCI(2,2) Vertical | SF-NC-TDDFT PBE50 Vertical | SF-NC-TDDFT PBE50 Adiabatic | SF-NC-TDDFT PBE50 Adiabatic + ZPVE |
|---|---|---|---|---|
| 6,12-dimesitylindeno[1,2-b]fluorene | −42.30 | −29.22 | −20.89 | −19.35 |
| 7,14-dimesitylfluoreno[3,2-b]fluorene | −27.91 | −17.46 | −11.44 | −10.25 |
| 8,16-dimesityldiindeno[1,2-b: 1',2'-i]anthracene | −20.05 | −11.42 | −7.96 | −7.13 |
| 310 | −32.89 | −20.49 | −16.65 | −15.79 |
| 308a | −19.82 | −11.65 | −9.37 | −8.77 |
| 312 | −13.25 | −6.97 | −5.11 | −4.37 |

TABLE 7

Comparison of y calculated by different methods.

| Compound | PUHF | Tuned-LC-RBLYP CASCI (2,2) | SF-NC-TDDFT PBE50$^†$ |
|---|---|---|---|
| 6,12-dimesitylindeno[1,2-b]fluorene | 0.299 | 0.088 (μ = 0.1621) | 0.119 |
| 7,14-dimesitylfluoreno[3,2-b]fluorene | 0.492 | 0.151 (μ = 0.1546) | 0.208 |
| 8,16-dimesityldiindeno[1,2-b: 1',2'-i]anthracene | 0.615 | 0.206 (μ = 0.1469) | 0.294 |
| 310 | 0.406 | 0.112 (μ = 0.1497) | 0.161 |
| 308a | 0.613 | 0.203 (μ = 0.1444) | 0.272 |
| 312 | 0.725 | 0.273 (μ = 0.1376) | 0.382 |

$^†$Since natural orbital analysis of SF-NC-TDDFT result is not available in the present version of program package, y of SF-NC-TDDFT PBE50 calculation is approximately estimated by twice the square of excitation amplitude for double excitation configuration. Such an approximation is considered to work when the ground and double excitation configurations are predominant in the ground state. In the present case, the sum of the weight of these two configurations is found to be more than 94% for the compounds.

Example 14

In this example, 7,14-dimesitylfluoreno[3,2-b]fluorene and compound 308a were evaluated. In the two-electron diradical model, the Δ ES-T gap as a function of y is expressed as $$\Delta E_{S-T} = \frac{U}{2}\left[1 - \frac{1}{\sqrt{y(2-y)}}\right] + 2K_{ab} = \frac{U}{2} f_{ST}(y) + 2K_{ab} \quad \text{Equation 1}$$

with $$y = 1 - \frac{1}{\sqrt{1 + \left(\frac{U}{4t_{ab}}\right)^2}} \quad \text{Equation 2}$$

where U is the difference between on- and inter-site Coulomb repulsions, Kab is the direct exchange integral, tab is the transfer integral and $f_{ST}(y)$ is the square brackets part in Equation 1, all defined between the electrons in the localized natural orbitals a and b. Here, $K_{ab}$ is positive, while $f_{ST}(y)$ increases from a large negative value to 0 with increasing y from ~0 to 1. This implies that a non-magnetic molecule takes a singlet ground state ($\Delta E_{S-T}<0$), and $|\Delta E_{S-T}|$ becomes small with increasing y if the U value is a constant, while if a molecule has a larger U while keeping y constant, $|\Delta E_{S-T}|$ could become large even at the same y. U and $t_{ab}$ are related, respectively, to the spatial overlap and energy gap between the bonding HOMO and anti-bonding LUMO. Singlet-triplet gap ($\Delta E_{S-T}$) and physical parameters for certain compound embodiments and comparative compounds are provided in Table 8 below. These data were calculated by the CASCI(2,2) method using the MOs obtained by tuned-LC-RBLYP/6-311G(d) calculation along with the tuned range-separating parameters p.

TABLE 8

| | 6,12-dimesityl-indeno[1,2-b]fluorene | 7,14-dimesityl-fluoreno[3,2-b]fluorene | 8,16-dimesityl-diindeno[1,2-b:1',2'-i]anthracene |
|---|---|---|---|
| μ (bohr$^{-1}$) | 0.1621 | 0.1546 | 0.1469 |
| $\Delta E_{S-T}$ (kcal mol$^{-1}$) | −42.3 | −27.9 | −20.1 |
| y (−)$^{a)}$ | 0.088 | 0.151 | 0.206 |
| $|t_{ab}|$ (eV) | 1.490 | 1.163 | 0.957 |
| $f_{ST}(y)$ (−) | −1.442 | −0.894 | −0.647 |
| $\frac{U}{2} = K^M_{gu}$ (eV) | 1.338 | 1.446 | 1.463 |
| (U/2)$f_{ST}(y)$ (eV) | −1.929 | −1.293 | −0.946 |
| $J^M_{gg}$ (eV) | 5.032 | 4.566 | 4.172 |
| $J^M_{uu}$ (eV) | 5.224 | 4.667 | 4.231 |
| $J^M_{gu}$ (eV) | 5.033 | 4.535 | 4.125 |
| $2K_{ab}$ (eV) | 0.095 | 0.082 | 0.077 |
| | 310 | 308a | 312 |
| μ (bohr$^{-1}$) | 0.1497 | 0.1444 | 0.1376 |
| $\Delta E_{S-T}$ (kcal mol$^{-1}$) | −32.9 | −19.8 | −13.3 |
| y (−)$^{a)}$ | 0.112 | 0.203 | 0.273 |
| $|t_{ab}|$ (eV) | 1.364 | 1.031 | 0.834 |
| $f_{ST}(y)$ (−) | −1.171 | −0.655 | −0.457 |
| $\frac{U}{2} = K^M_{gu}$ (eV) | 1.416 | 1.563 | 1.573 |
| (U/2)$f_{ST}(y)$ (eV) | −1.658 | −1.025 | −0.720 |
| $J^M_{gg}$ (eV) | 4.743 | 4.417 | 4.055 |
| $J^M_{uu}$ (eV) | 5.437 | 4.755 | 4.233 |
| $J^M_{gu}$ (eV) | 4.858 | 4.420 | 3.999 |
| $2K_{ab}$ (eV) | 0.232 | 0.165 | 0.145 |

Figure 7:
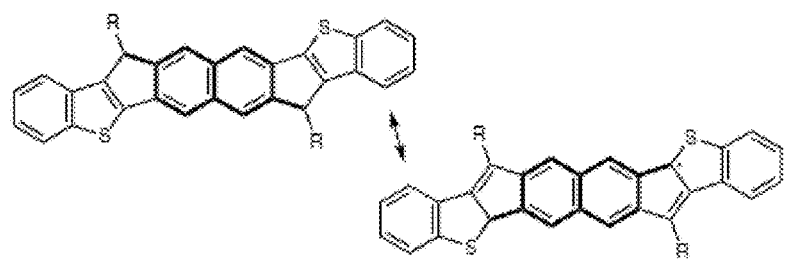

Theoretically in Table 5, 7,14-dimesitylfluoreno[3,2-b]fluorene and compound 308a are diradicals with y (7,14-dimesitylfluoreno[3,2-b]fluorene)<y (308a), which is a result of the fact that $|t_{ab}|$ (7,14-dimesitylfluoreno[3,2-b]fluorene)>$|t_{ab}|$ (308a) and U (7,14-dimesitylfluoreno[3,2-b]fluorene)<U (308a) according to Table 8 and Equation (2). Without being limited to a single theory of operation, it currently is believed that these differences may be explained by the fact that (1) the HOMO-LUMO gap is smaller in compound 308a than in 7,14-dimesitylfluoreno[3,2-b]fluorene owing to the larger π-conjugation offered by the benzothiophene motif compared to benzene; and (2) the electron-rich sulfur atom offers a stronger repulsion environment (that is, U) near the radical center than the benzene units alone. This shows the dual electronic role of thiophenes, either as electron polarizable rings (that is, low aromaticity, π-conjugation enabler) and as electron-rich donor sites, and both effects are favorable for the increase in diradical character. Interestingly, the thiophene rings in the diradical configurations also act as π-delocalization limits (little to no electronic extension onto the peripheral benzenes in compound 308a in contrast to 7,14-dimesitylfluoreno[3,2-b]fluorene in FIGS. 5A, 5B, 6A, and 6B), which concentrates and greatly stabilizes the electron and spin density between them. This is also related to the fact that the low aromaticity and larger π-conjugation of thiophene (which reduces the energy required to break a double bond) allow additional diradical resonance forms in compound 308a when compared with 7,14-dimesitylfluoreno[3,2-b]fluorene (FIG. 7). Given that $K_{ab}$ is negligibly small (Table 8) in both compounds, $\Delta E_{S-T}$ is determined by the first addend that depends exclusively on U and y and that gives rise to $|\Delta E_{S-T}(7)|>|\Delta E_{S-T}(308a)|$ with Equation 1.

By comparing 7,14-dimesitylfluoreno[3,2-b]fluorene and compound 308a, both U and y have significant weight in the final $\Delta E_{S-T}$ outcome. From compound 308a to 312, U is increased while $|t_{ab}|$ is decreased due to the larger anthracene π-core in 312, resulting in an increase of y and, consequently, $|\Delta E_{S-T}(312)|<|\Delta E_{S-T}(308a)|$. In other words, the theoretical scenario is that compound 308a has medium/large diradical character (y=0.61) that gives a moderate/large $|\Delta E_{S-T}|$ gap, representing a molecular platform where diradical properties might be extensively expressed and yet preserved from the interference of low-energy-lying magnetically active triplets (and thus triplet reactivity). To provide experimental evidence of the unexpected role that thiophene plays for the divergence between y and $\Delta E_{S-T}$, the preparation of derivatives compounds 308a-308c and characterization of their diradical properties are described next.

Example 15

As described herein, the synthesis of compound 308a-308c was achieved using a bistriflate intermediate 300. Suzuki cross-coupling of 300 with benzothiophene 2-pinacolate ester gave the desired naphthalene 304 in 88% yield. Saponification of diester 304 followed by intramolecular Friedel-Craft acylation furnished poorly soluble dione 306 in 77% yield. Addition of mesityllithium to 306 generated an intermediate diol, which was then reduced using SnCl$_2$ in rigorously anaerobic and anhydrous reaction conditions to afford the fully conjugated mesityl-substituted compound 308a as a vibrant deep purple solid in 62% yield. Repetition of this sequence with triisopropylphenyllithium gave the corresponding compound 308b, albeit in reduced yield because of the difficulty of adding the bulky nucleophile to the electrophilic dione.

Figure 8:
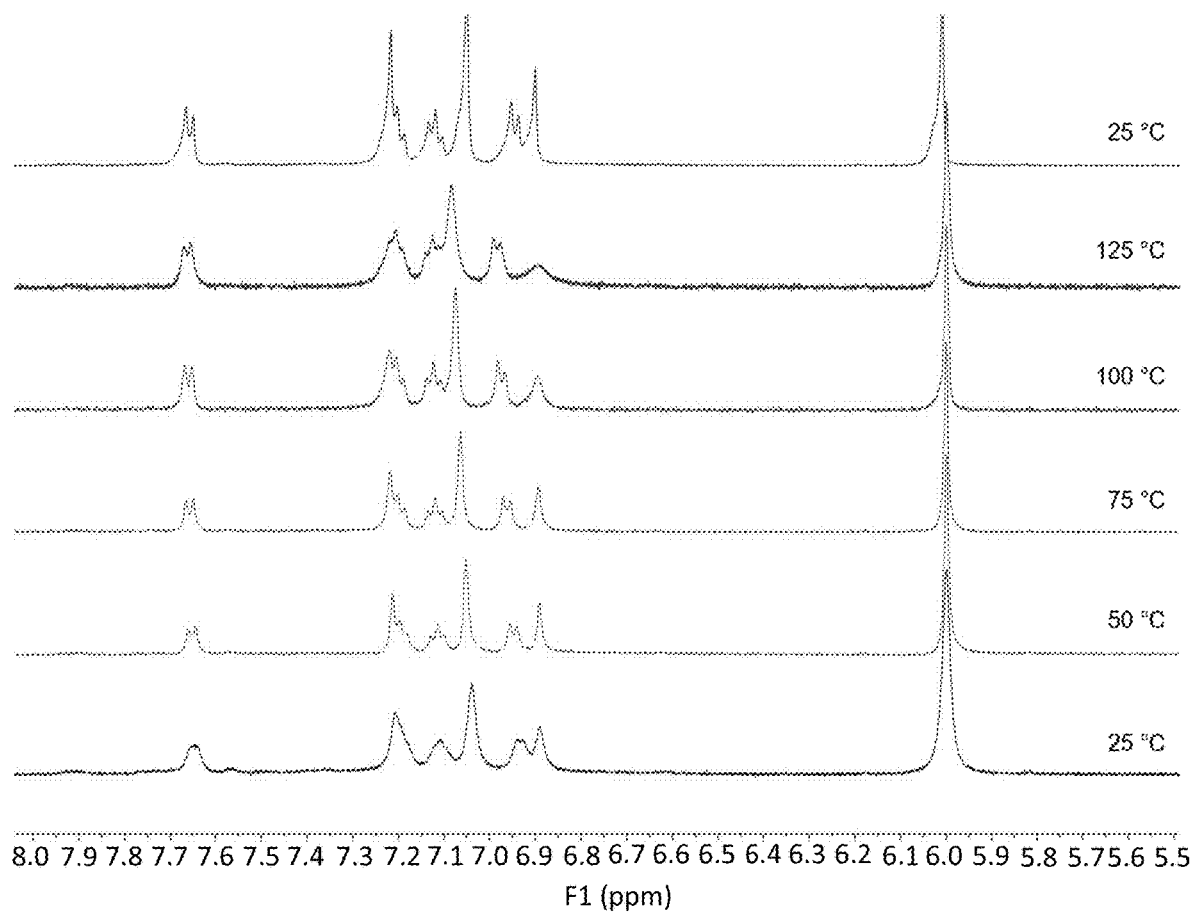
FIG. 8 is a combined spectrum showing variable temperature $^1$H NMR spectra of the aromatic region of compound 308a in 1,1,2,2-tetrachloroethane-$d_2$.

Interestingly, the $^1$H NMR spectra of compounds 308a, and 308b at room temperature displayed well-resolved signals. This result is somewhat surprising compared to the proton spectrum of diindenoanthracene, which clearly showed broadened signals at room temperature. Heating a sample of compound 308a in 1,1,2,2-tetrachloroethane-d2 to 125° C. did not result in appreciable peak broadening (FIG. 8), whereas diindenoanthracene at the same temperature showed only broad, featureless humps in its proton spectrum. In particular, approximately 10 mg of compound 308a was dissolved in 1,1,2,2-tetrachloroethane-d2 and transferred to a J-Young tube. The solution was degassed by four freeze-pump-thaw cycles. Spectra were acquired in a Varian Inova 500 MHz spectrometer that was heated to 50, 75, 100, 125, then 25° C. (FIG. 8).

The disparity between the NMR data sets, where both molecules possess nearly identical diradical character values (~0.6), could be indicative for compound 308a being a diradical species with a large, thermally prohibitive $\Delta E_{S-T}$ gap in this range of temperatures. This possibility is corroborated by the calculated $\Delta E_{S-T}$ values of −4.9 and −8.8 kcal mol$^{-1}$ for diindenoanthracene and compound 308a, respectively, as well as by ESR and SQUID experiments, which were silent for possible triplet species up to 400 K for compound 308a, whereas analogous experiments clearly showed a triplet state for diindenoanthracene.

Figure 9:
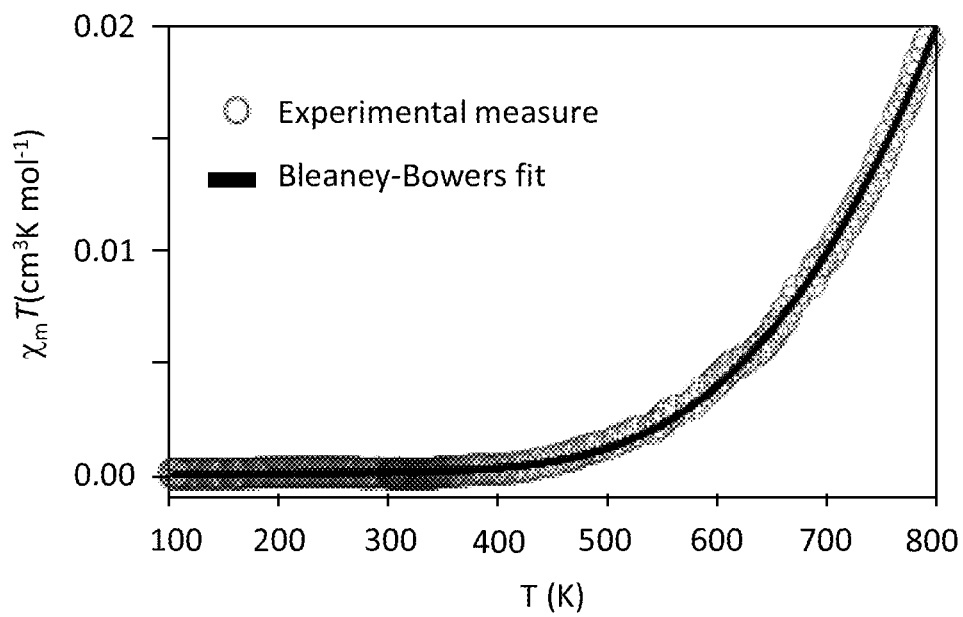
FIG. 9 is a graph showing thermal variation of the $\chi_m$ T product of compound 308a in the solid state in the temperature range 100-800 K from SQUID measurements, wherein the solid line is the best fit to the model.
Figure 10:
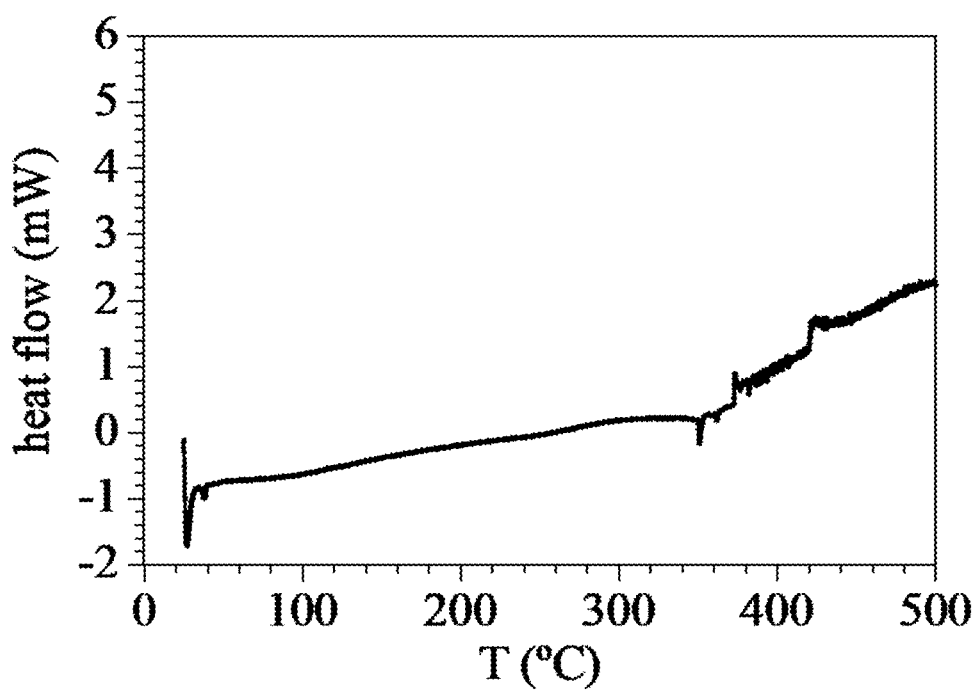
FIG. 10 is a graph showing DSC measurement of compound 308a in an oxygen-free dry $N_2$ flow in the temperature range 25-500° C. (298-773 K).

Magnetic measurements with SQUID and ESR on the vast majority of diradical molecules in the literature typically do not go higher than 400-500 K, an insufficient range to experimentally evaluate $\Delta E_{S-T}$ values in the disclosed compound embodiments. Consequently, SQUID measurements were performed for compound 308a with a sample space oven capable of reaching temperatures up to 800 K inserted into the instrument. FIG. 9 reveals a continuous increase in magnetic molar susceptibility after ~450 K. Fitting the data to the Bleaney-Bowers equation affords a low to high spin energy gap, $\Delta E_{S-T}$, of −8.0 kcal mol$^{-1}$. This experimental value is in very good agreement with the adiabatic $\Delta E_{S-T}$ value from calculations, −8.8 kcal mol$^{-1}$, for compound 308a. Given the different spin multiplicity of the state transition, the free energy variation at 298.15 K was calculated at the same level of theory, resulting in a value of −7.9 kcal mol$^{-1}$, also in excellent accordance with the experiment. Differential scanning calorimetry (DSC) data (FIG. 10) confirmed the stability of compound 308a at these high temperatures.

SQUID Magnetic Measurements—

Magnetic susceptibility measurements were performed with a Quantum Design MPMS-XL-7 SQUID susceptometer equipped with a sample space oven reaching a maximum temperature of 800 K. Two sets of measurements were performed: In the 100-400 K temperature range the magnetic susceptibility was measured with an applied magnetic field of 1 T using the standard sample space of the SQUID susceptometer with the sample sealed in a plastic bag. In the 300-800 K temperature range the magnetic susceptibility was measured also with an applied field of 1 T using a sample space oven with the sample inserted in a 1.5 mm diameter aluminium foil cylinder that was mounted as described in reference 3.[3] The susceptibility data were corrected for the same sample holder previously measured using the same conditions and for the diamagnetic contributions of the compound as deduced by using Pascal's constant tables.

The magnetic measurements show a $\chi_m T$ value close to 0 below ca. 400 K and a smooth increase at higher temperatures to reach a value slightly above 0.02 cm$^3$K mol$^{-1}$ at 800 K (FIG. 9). This is a very small value, as expected for a coupled S=½ dimer. In fact, the fit to a S=½ dimer model (the $\chi_m T$ vs. T curve was fitted using the classical Bleaney-Bowers model for an antiferromagnetic S=½ dimer) reproduces satisfactorily the magnetic properties with g=2.00(2), J=−4032(21) K and a paramagnetic S=½ impurity of ca. 0.2% with a regression factor, R=9.99964 (the Hamiltonian is written as H=−JS$_1$S$_2$). This J value corresponds to a $\Delta E_{ST}$ of ca. −8.01 kcal mol$^{-1}$. The paramagnetic impurity may come from a small fraction of monoradical. Note that, given the low magnetic signal, the J value obtained presents an uncertainty of at least 10% rather than the ca. 0.5% suggested by the standard deviation of the parameter provided by the fitting procedure. This behavior is consistent with the $^1$H NMR data, which slightly start to broaden commencing at 425 K (see FIG. 8).

Differential Scanning calorimetry (DSC) measurement (Mettler Toledo DSC 821e) was performed on the same sample of compound 308a that was used for the magnetic measurements from 25-500° C. (up to 773 K, the maximum temperature reached by the equipment). The measurement was performed under an oxygen-free dry N$_2$ flow with a scan rate of 5° C. min$^{-1}$. The DSC of compound 308a (FIG. 10) shows that this compound does not present any noticeable thermal decomposition below 500° C. (773 K), in agreement with the SQUID magnetic measurements that do not show any decomposition below 800 K under the measurement conditions (static He atmosphere).

Figure 11:
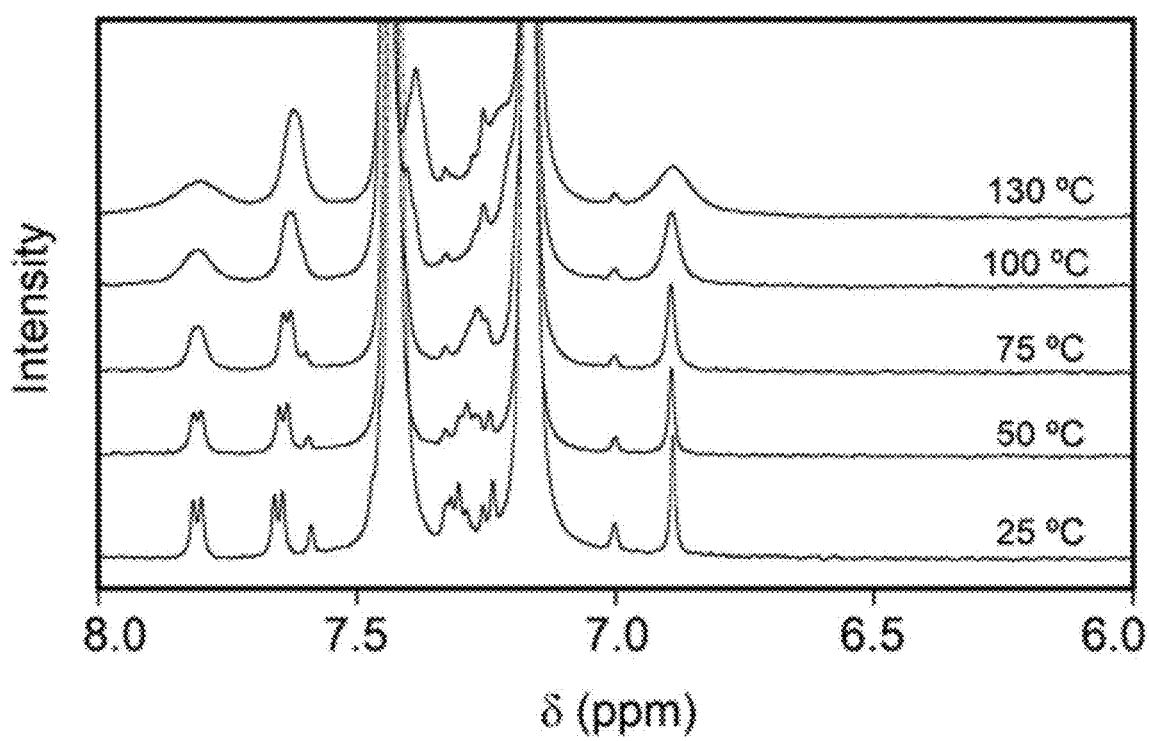
Figure 12:
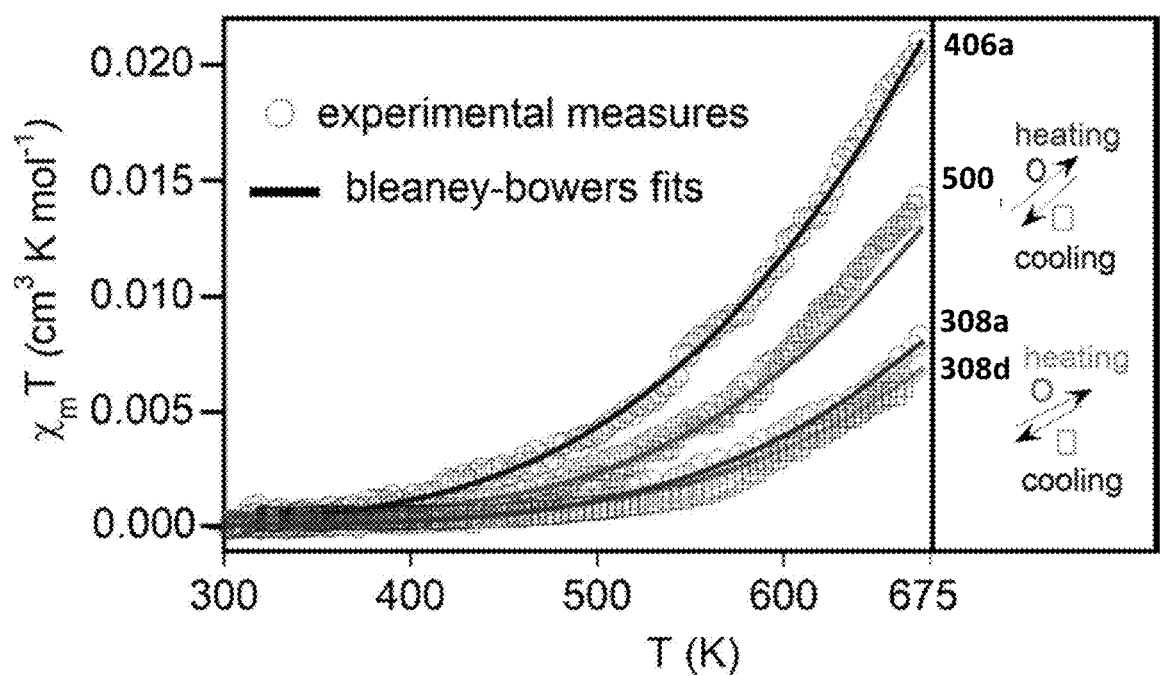
FIG. 12 is a graph showing SQUID magnetometry data of compounds 308a, 308d, 406a, and 500, wherein the heating and cooling cures are denoted by squares and circles, respectively.
Figure 13:
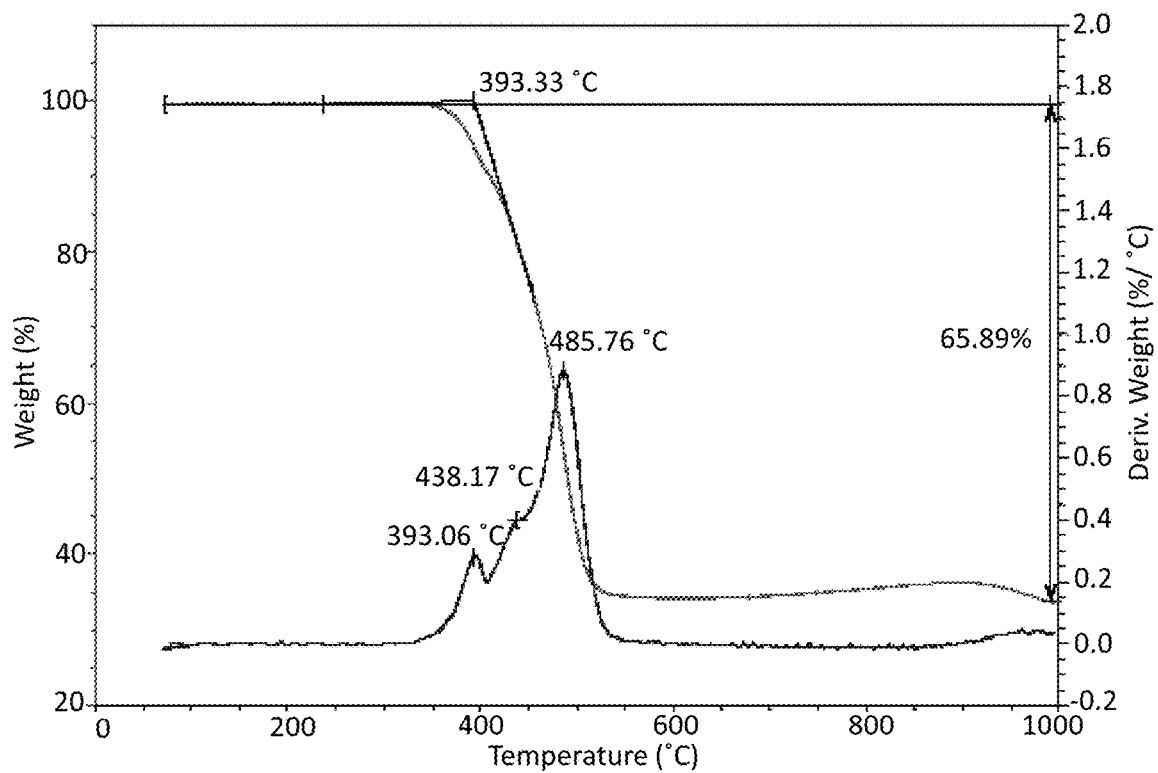
Figure 14:
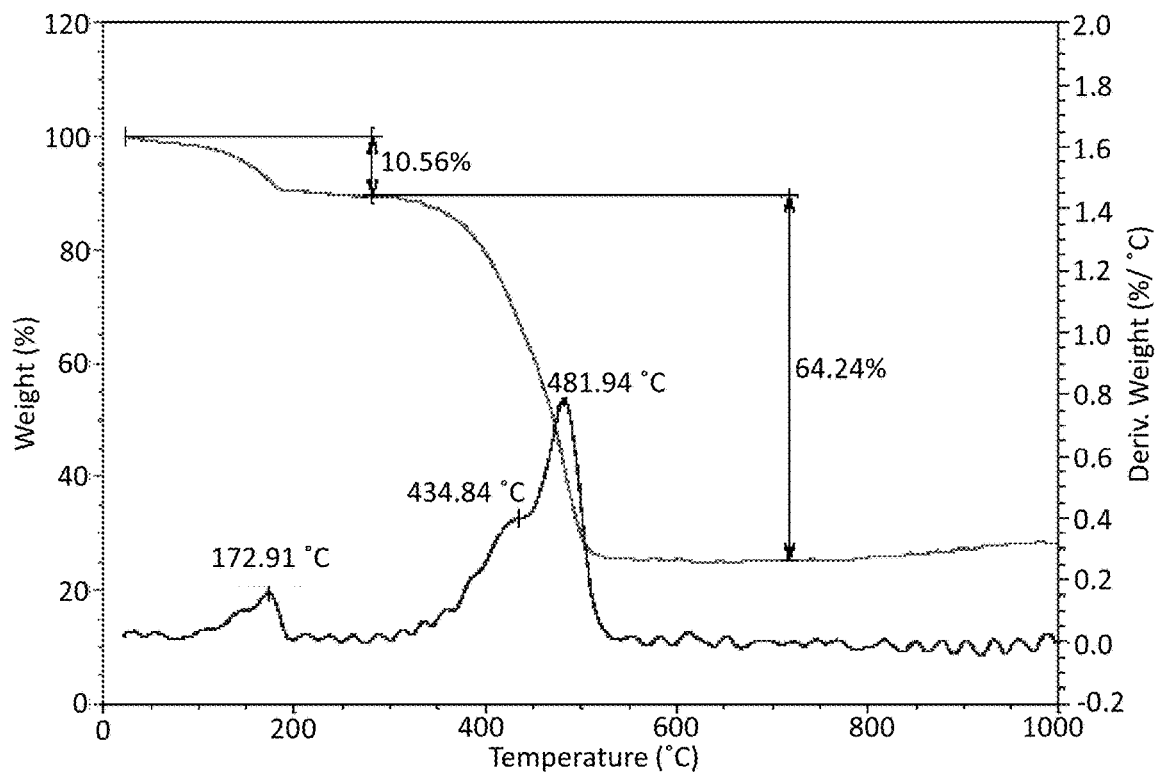
FIG. 14 is a thermogravimetric analysis plot for compound 308d.
Figure 15:
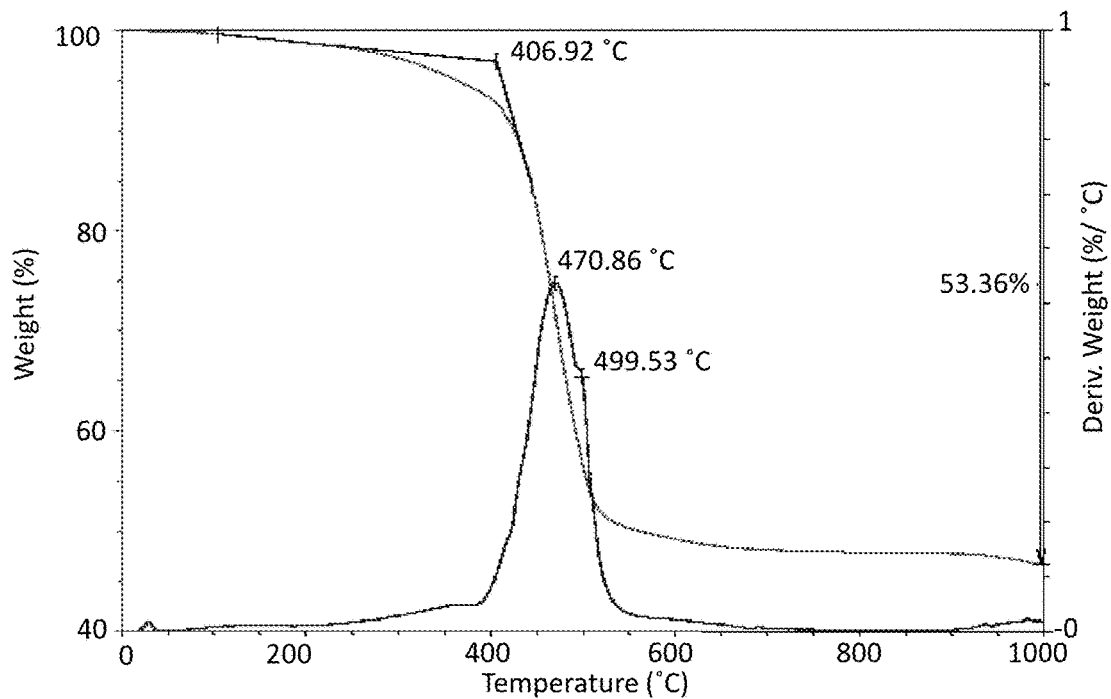
Figure 16:
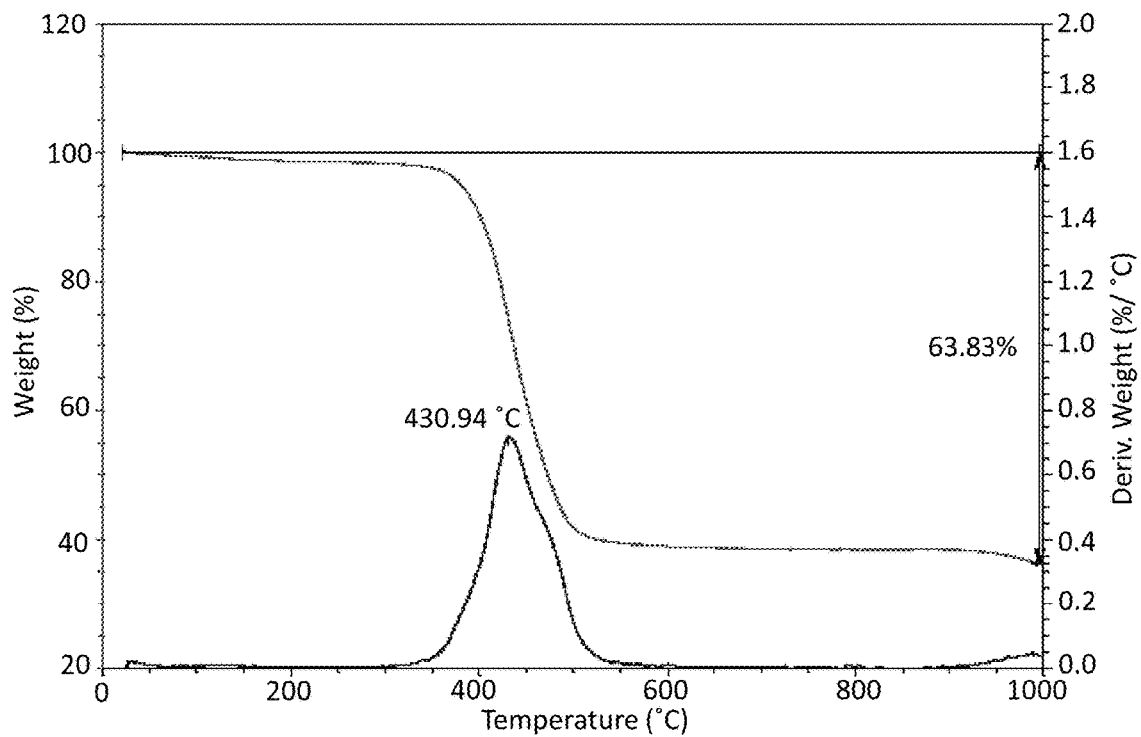
FIG. 16 is a thermogravimetric analysis plot for compound 500.
Figure 17:
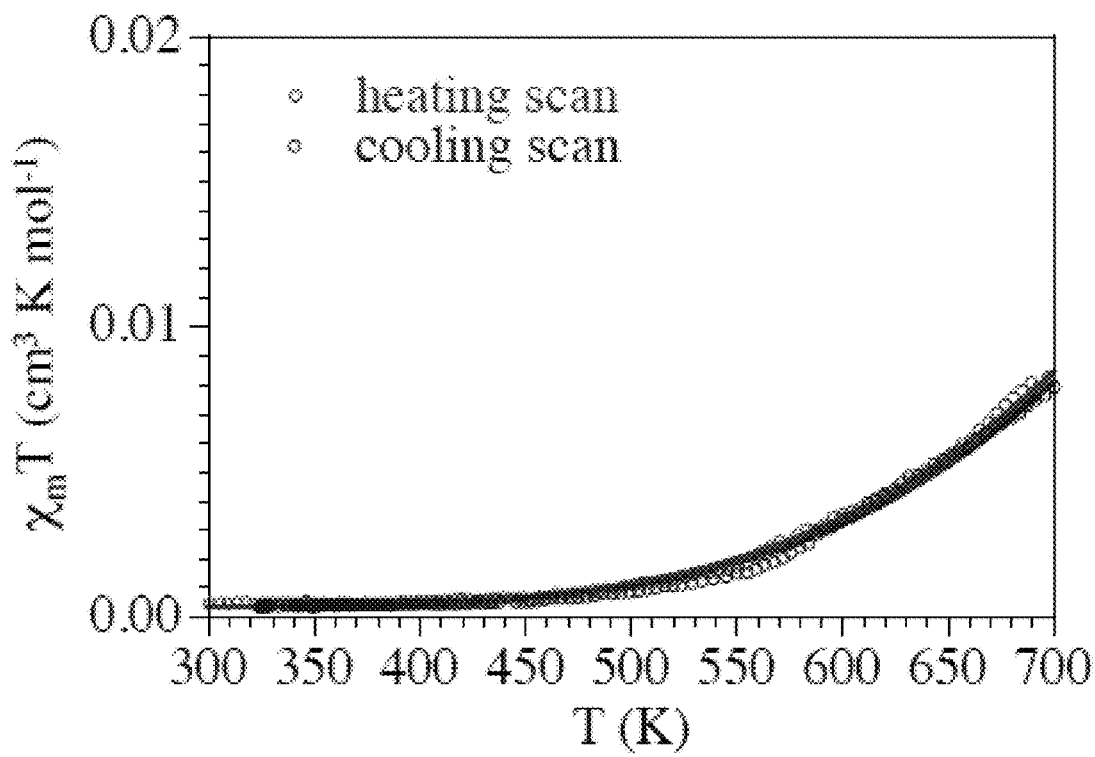
FIG. 17 shows results of using variable temperature SQUID measurements to analyze compound 308d.
Figure 18:
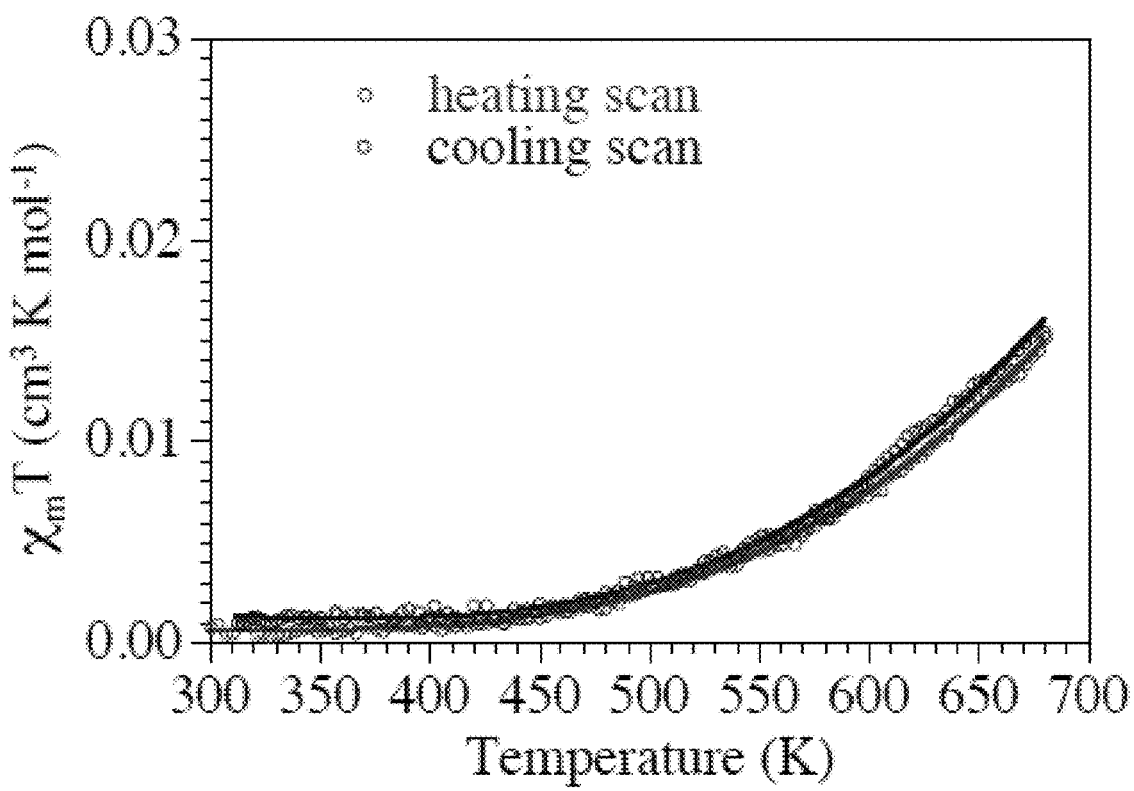
FIG. 18 shows results of using variable temperature SQUID measurements to analyze compound 500.

In yet another embodiment, the magnetic measurements were performed in the 300-700 K temperature range with an applied field of 1 T using a sample space oven with the samples inserted in a 1.5 mm diameter aluminum foil cylinder. Results are shown in FIGS. 11 and 12. The sample masses used for the magnetic measurements are 11.665, 3.868 and 1.469 mg for 406a, 308d and 500, respectively. The susceptibility data were corrected for the same sample holder previously measured using the same conditions and for the diamagnetic contributions of the compound as deduced by using Pascal's constant tables. The magnetic measurements were fitted using the classical Bleaney-Bowers model for an antiferromagnetic S=½ dimer. This model reproduces satisfactorily the magnetic properties of 406a with g=2.0(1), J=−3479 K and a paramagnetic S=½ impurity (p) of ca. 0.6% with a regression factor, R=0.99877 (the Hamiltonian is written as H=−JS$_1$S$_2$). This J value corresponds to a $\Delta E_{ST}$ of ca. −6.9 kcal mol$^{-1}$. Compounds 308d and 500 were measured in the heating and cooling scans in order to verify stability. The magnetic measurements of 308d and 500 were also fitted to the classical Bleaney-Bowers model. FIGS. 13-16 show the results of these measurements. This model for 308d gives (solid lines in FIG. 15): g=2.0(1), J=−4141 K and ρ≈0.1% in the heating scan (R=0.9991) and g=2.0(1), J=−4227 K and p=0.1% in the cooling scan (R=0.9985). These J values correspond to $\Delta E_{ST}$ of ca. −8.2 and −8.4 kcal mol$^{-1}$, for the heating and cooling scans, respectively. For 500, the following was obtained (solid lines in FIG. 16): g=2.0(1), J=−3652 K and p=0.1% in the heating scan (R=0.9994) and g=2.0(1), J=−3533 K and ρ≈0.2% in the cooling scan (R=0.9979). These J values correspond to $\Delta E_{ST}$ of ca. −7.2 and −7.0 kcal mol$^{-1}$, for the heating and cooling scans, respectively. Variable temperature SQUID measurements in the heating and cooling scans are shown in FIG. 17 (compound 308d) and 18 (compound 500).

In all cases the paramagnetic impurities may come from a small fraction of mono-radical present in the sample. Given the low magnetic signal, the J value obtained presents an uncertainty of around 10%, as this error corresponds to the error in the cmT values (and, therefore in the g values that are directly related to them). For the estimated DEST values from the fit to the Bleaney-Bowers model, however, the DEST value mainly depends on the curvature of the plot as T increases; thus, the error in DEST can be evaluated to be around 0.2 kcal mol-1, which is more like 2-3%.

Example 16

In some examples, attempts to generate compound 308c afforded instead the hydrogenated product 308cH$_2$, confirmed by mass spectrometry (MS) and by the appearance of a new singlet at 5.22 ppm in the 1H NMR spectrum. This singlet disappeared when the reaction was spiked with D$_2$O (also confirmed by 2D NMR and MS). Although the methyl/isopropyl groups of compounds 308a and 308b provide steric protection of the carbon centers with high radical character, this clearly is not the case in compound 308c, which allows the radical centers the opportunity to scavenge hydrogen atoms. To prove that compound 308cH$_2$/compound 308cD$_2$ resulted from radical reactivity, repetition of the SnCl$_2$ reaction in the presence of Bu$_3$SnD, a deuterium source known to proceed via a radical mechanism, furnished compound 308cD$_2$ as the sole isolable product.

Example 17

Figure 19:
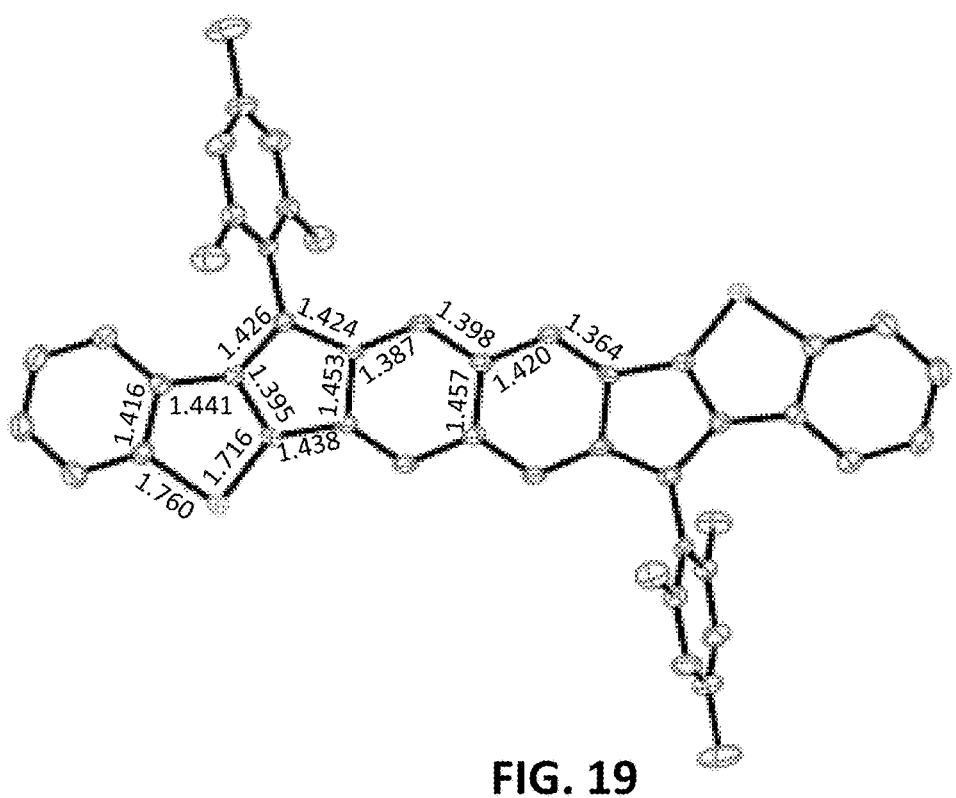
FIG. 19 is an ORTEP image of compound 308a with selected bond distances (in Å) within the hexacyclic core, wherein the ellipsoids are drawn at the 35% probability level and hydrogen atoms omitted for clarity.

Deep blue crystals of compound 308a suitable for X-ray diffraction were obtained by layering CH$_3$CN over a concentrated solution of a compound embodiment in CHCl$_3$ (FIG. 19). The resultant X-ray structure revealed that the carbon-carbon bond length from the apical carbon to the naphthalene core (aforementioned bond 1) is 1.424 Å, which is much longer than the analogous bond length in diindenoanthracene (1.406 Å). This longer bond is indicative of diradical character, as known open-shell structures have significantly reduced double-bond character in this position. For example, the analogous bond lengths in indeno[2,1-b]fluorene and fluoreno[2,3-b]fluorene, molecules with pronounced diradical character and a thermally accessible triplet state, are both 1.437 Å. In contrast, the analogous bond lengths in compound 310 and 6,12-dimesitylindeno[1,2-b]fluorene are 1.409 and 1.380 Å, respectively, reflecting their reduced diradical character, further supporting the notion that compound 308a is an open-shell singlet diradicaloid.

Crystallographic Data for Compound 308a—

C$_{48}$H$_{36}$Cl$_6$S$_2$, C$_{46}$H$_{34}$S$_2$.2(CHCl$_3$), M=889.59, 0.18× 0.17×0.04 mm, T=173(2) K, Triclinic, space group P-1, a=7.9984(2) Å, b=9.6985(2) Å, c=14.2461(3) Å, α=103.997 (1°), β=99.148(1°), γ=90.097(1°), V=1057.72(4) Å$^3$, Z=1, D$_c$=1.397 Mg/m$^3$, ρ(Cu)=4.890 mm$^{-1}$, F(000)=458, 2θ$_{max}$=133.16°, 10265 reflections, 3710 independent reflections [R$_{int}$=0.0429], R1=0.0515, wR2=0.1406 and GOF=1.049 for 3710 reflections (253 parameters) with 1>2σ(I), R1=0.0560, wR2=0.1450 and GOF=1.049 for all reflections, max/min residual electron density+0.698/−0.720 eÅ$^{-3}$. CCDC-1832752 contains the supplementary crystallographic data for this compound.

Crystallographic Data for Compound 500.

C$_{54}$H$_{48}$Cl$_6$S$_2$, C$_{52}$H$_{46}$S$_2$.2(CHCl$_3$), M=973.74, 0.185× 0.073×0.037 mm3, T=200.00(10) K, Monoclinic, space group P21/c, a=8.11560(10) Å, b=9.97380(10) Å, c=29.2458(3) Å, α=90°, b=94.8550(10°), γ=90°, V=2358.76(4) Å3, Z=2, Dc=1.371 Mg/m3, μ(Cu)=4.432 mm-1, F(000)=1012, 2θmax=67.723°, 29112 reflections, 4271 independent reflections [R(int)=0.0397], R1=0.0847, wR2=0.2315 and GOF=1.041 for all reflections, max/min residual electron density+1.232/−0.929 eÅ$^{-3}$. CCDC 1949404.

Example 18

Figure 20:
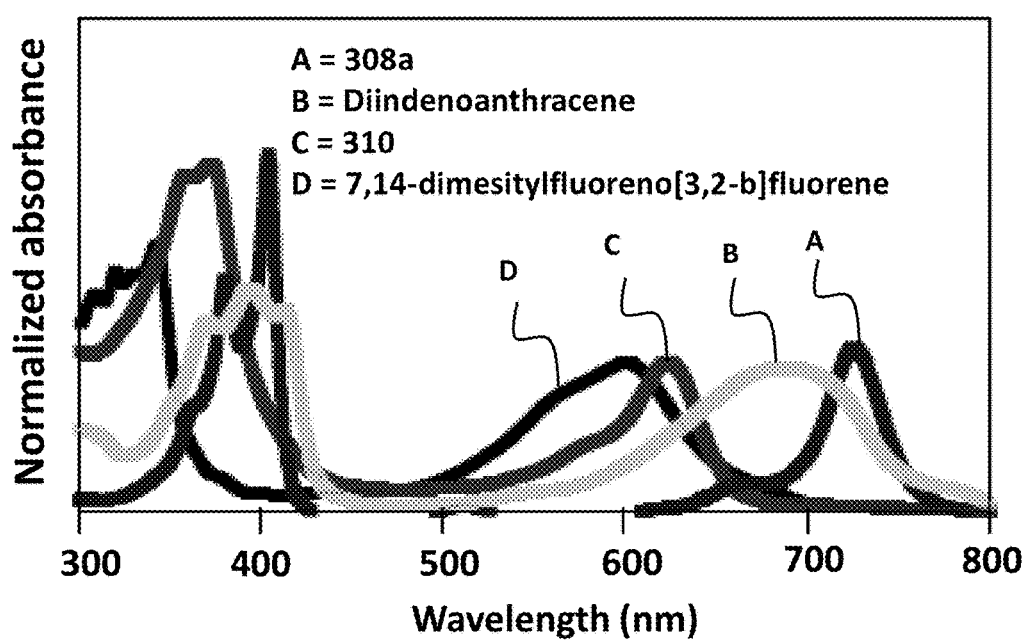
FIG. 20 is graph showing results from comparting the electronic absorption spectrum of compound 308a (line A), diindenoanthracene (line B), compound 310 (line C), and 7,14-dimesitylfluoreno[3,2-b]fluorene (line D) in $CH_2Cl_2$.

Comparison of the UV-vis absorption profile (FIG. 20) of compound 308a (line labeled "A") to 7,14-dimesitylfluoreno [3,2-b]fluorene (line labeled "D") and to compound 310 (line labeled "C") shows that the wavelength maxima of compound 308a are redshifted compared to those of the all-hydrocarbon counterpart, in line with the increase in π-conjugation in the thiophene derivative, as theoretically demonstrated above (see discussion of t$_{ab}$). Additionally, there is a low energy absorption at ~725 nm that is indicative of a narrow HOMO-LUMO gap and a low-energy shoulder at 750 nm that is associated with the one-photon activation of the two-photon absorption band arising from the large diradical contribution to the ground electronic state. Time-dependent density functional theory (TDDFT) calculations at the UB3LYP/6-311G(d) level predict that the first absorption bands of 7,14-dimesitylfluoreno[3,2-b]fluorene and compound 308a are at 618 nm (f=0.734) and 722 nm (f=0.628), both of which are assigned as a one-electron HOMO-LUMO transition. The HOMO-LUMO energy gaps of 7,14-dimesitylfluoreno[3,2-b]fluorene and compound 308a are estimated to be 1.92 eV and 1.57 eV, respectively, at the RB3LYP/6-311G(d) level. The computational results are in good agreement with the experimental λ$_{max}$ values (600 and 725 nm, respectively) and optical energy gaps (1.82 and 1.55 eV, respectively). Comparison of diindenoanthracene (line labeled "B" in FIG. 20) with compound 308a embodiments of the present disclosure shows that compound 308a has a more well-defined absorbance profile; however, both molecules have low energy absorbances characteristic of diradical character.

Figure 21:
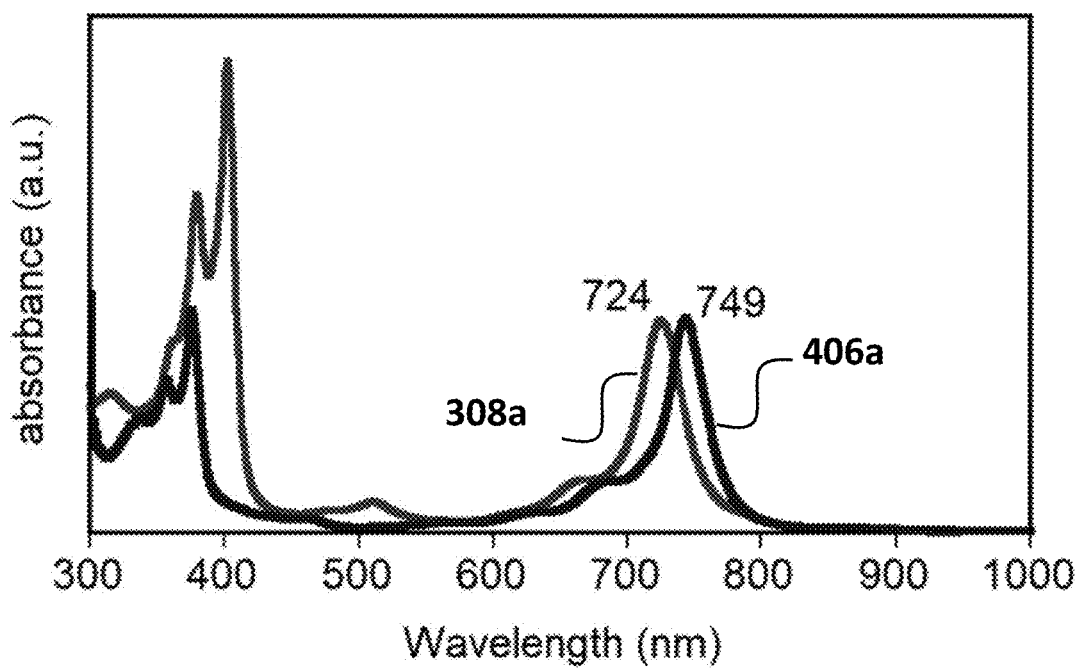
FIG. 21 is graph showing results from comparting the electronic absorption spectrum of compound 308a and compound 406a in $CH_2Cl_2$.

The electronic absorption spectra of compounds 308a and 406a (see FIG. 21) depict a red-shift of +25 nm from 724 to 749 nm going from 308a to 406a, indicating a reduction of the optical gap even though the two compounds are compositionally identical. Quantum chemical calculations (TD-UB3LYP/6-311G* level) also predict a similar red-shift from 703 nm for 308a to 741 nm for 406a of the main lowest energy lying theoretical excitation, which corresponds to a HOMO-LUMO transition. In the lowest energy part of these strong absorptions, weak shoulders can also be observed that are typical of diradical molecules and are associated with double excitations.

Example 19

Figure 22:
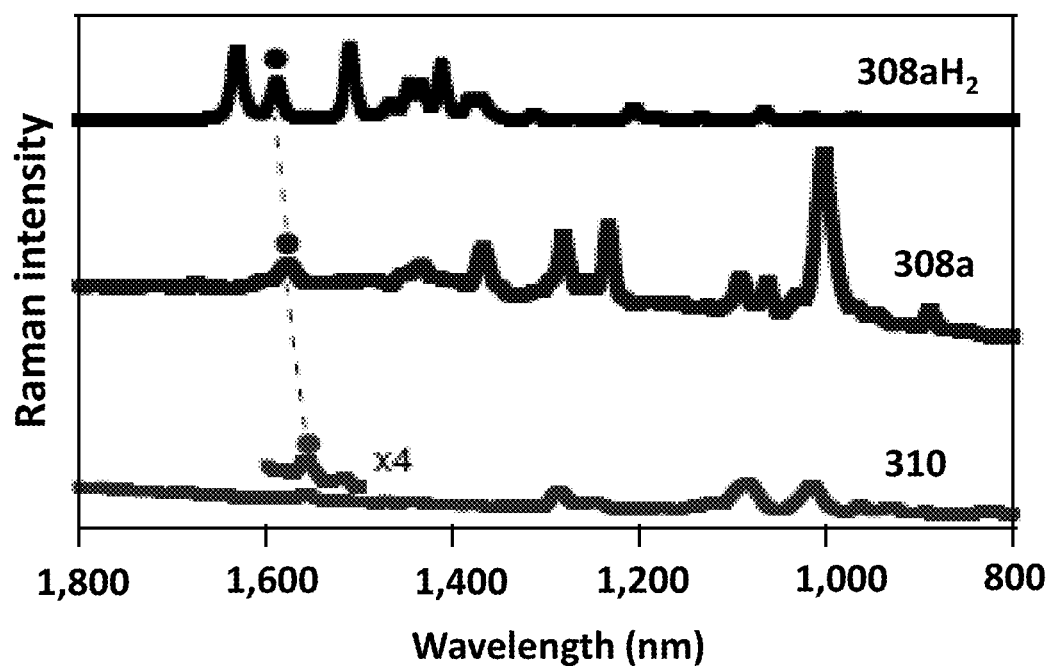
FIG. 22 provides room temperature solid-state 785 nm Raman spectra of compound 310, compound 308a, and compound 308c$H_2$.

The 785 nm resonance Raman spectrum of compound 308a is shown in FIG. 22 together with the spectra of reference compounds compound 310 and compound 308cH$_2$. The emergence of bands in the range 1,600-1,570 cm$^{-1}$ is typical of aromatic acenes, which is relevant in the context of the current discussion as the conversion between the closed-shell and open-shell resonance structures would result in aromatization of the naphthalene core of compound 308a. The Raman spectrum of diindenoanthracene (FIG. 23) displayed medium intensity bands in this region as a result of aromatization of the central anthracene moiety. The spectrum of 310 is characterized by the near absence of the band in the 1,600-1,570 cm$^{-1}$ region, while compound 308a displays a new band at 1,576 cm$^{-1}$, indicating aromatization of the naphthalene core and therefore supporting the diradical nature of the ground electronic state of compound 308a. In comparison, the position of this band is very near that of compound 308cH$_2$ (1,587 cm$^{-1}$), a molecule that possesses a fully aromatized naphthalene core.

Figure 23:
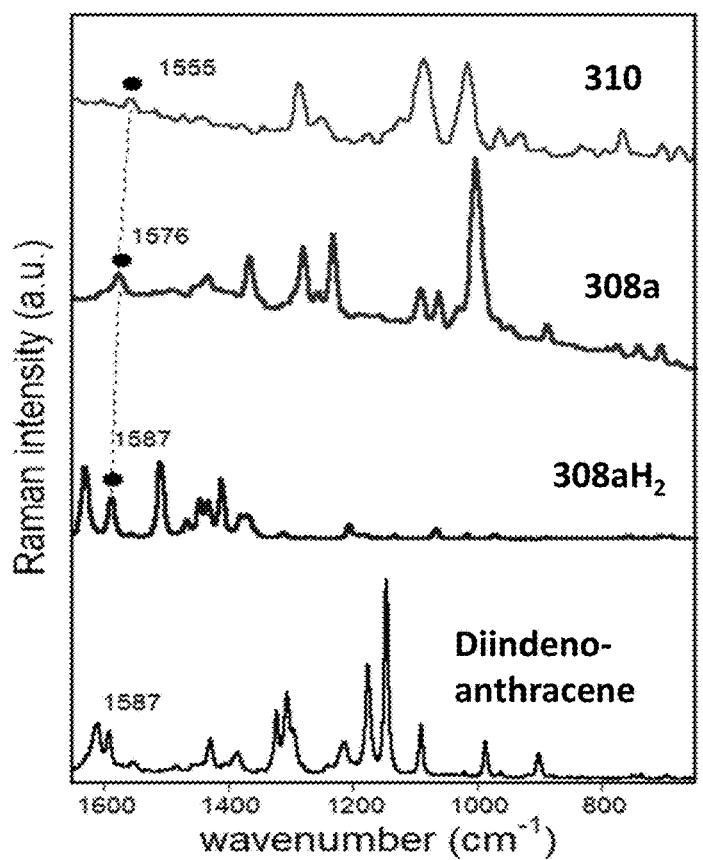
FIG. 23 provides room temperature solid-state 633 nm Raman spectrum of diindenoanthracene and 785 nm Raman spectra of compound 310, compound 308a, and compound 308c$H_2$.

Comparison between Raman spectra of compound 308a and compound 308cH$_2$—The Raman spectrum of compound 308a in its singlet open-shell pseudo-aromatic state (FIG. 23) displays the CC stretching mode of the naphthalene core at 1576 cm$^{-1}$, which is upshifted regarding the same CC stretching mode of the quinoidal benzene core in 310 at 1555 cm$^{-1}$. The frequency upshift from compound 3104 compound 308b reveals the partial aromatization of the naphthalene core. This aromatization process of the naphthalene is not complete as one can clearly seen by comparing with the Raman spectrum of the precursor compound 308cH$_2$, which is characterized by a full aromatized naphthalene moiety and has its CC stretching mode of the naphthalene further upshifted at 1587 cm$^{-1}$. This can be alternatively viewed in terms of the partial quinoidization of the naphthalene core in compound 308a regarding the fully aromatic 10cH$_2$ as a result of the bonding between the unpaired electrons of the diradical of compound 308a. The Raman spectrum of diindenoanthracene is also shown in FIG. 23. It has its CC stretching mode of the anthracene core at 1589 cm$^{-1}$, which is upshifted by +13 cm$^{-1}$ regarding the similar mode in compound 308c, 1576 cm$^{-1}$.

Figure 24:
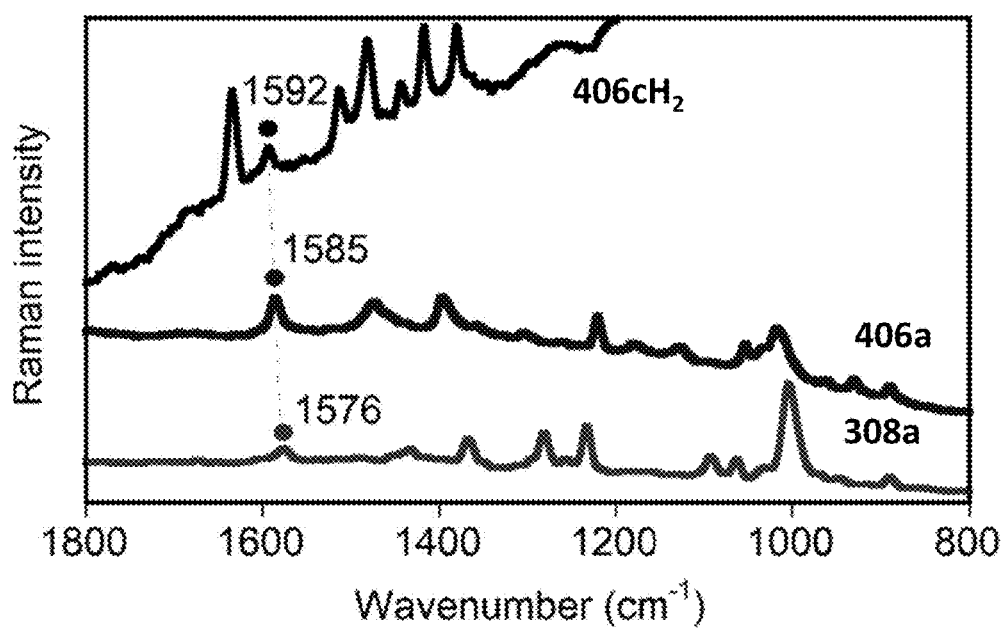
FIG. 24 provides room temperature solid-state 1064 nm Raman spectrum of compound 406a, compound 308a, and compound 308c$H_2$.

The solid-state Raman spectra of 308a and 406a at room temperature are shown in FIG. 24. The characteristic C=C stretching mode of the central naphthalene unit in 308a appears at 1576 cm$^{-1}$ and is representative of a transitional structure from quinoidal to aromatic for this core. This agreed with a medium diradical index of y=0.61, confirming that aromaticity recovery is the main driving force for diradical formation, although it is not fully completed. In the case of 406a (y=0.66), the same yet more intense Raman band emerges at 1585 cm$^{-1}$, upshifted by +9 cm$^{-1}$, indicating an additional gain of aromatization of the naphthalene core in this isomer. In addition, this band is only +7 cm$^{-1}$ away from the same stretching mode in 406cH$_2$ (1592 cm$^{-1}$), a molecule that contains a fully aromatized naphthalene (note that in 308a→308cH$_2$ the upshift is +11 cm$^{-1}$). The emerging interpretation is that the contribution of the 2,6-naphthoquinoidal conjugation to ΔEST does not arise separately from cross-conjugation of the sulfur lone pair and the radical, but there is a synergy between the two.

Example 20

Figure 25:
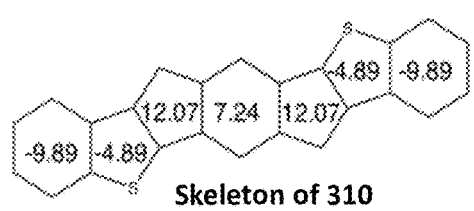
FIG. 25 illustrates NICS(1) values (ppm) for each ring calculated at the UB3LYP/6-311G(d) level of approximation for 7,14-dimesitylfluoreno[3,2-b]fluorene and compounds 308a and 310.
Figure 25:
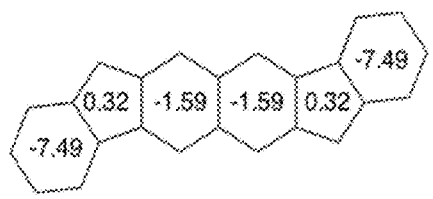
Figure 25:
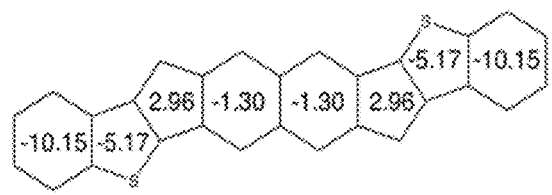
Figure 26:
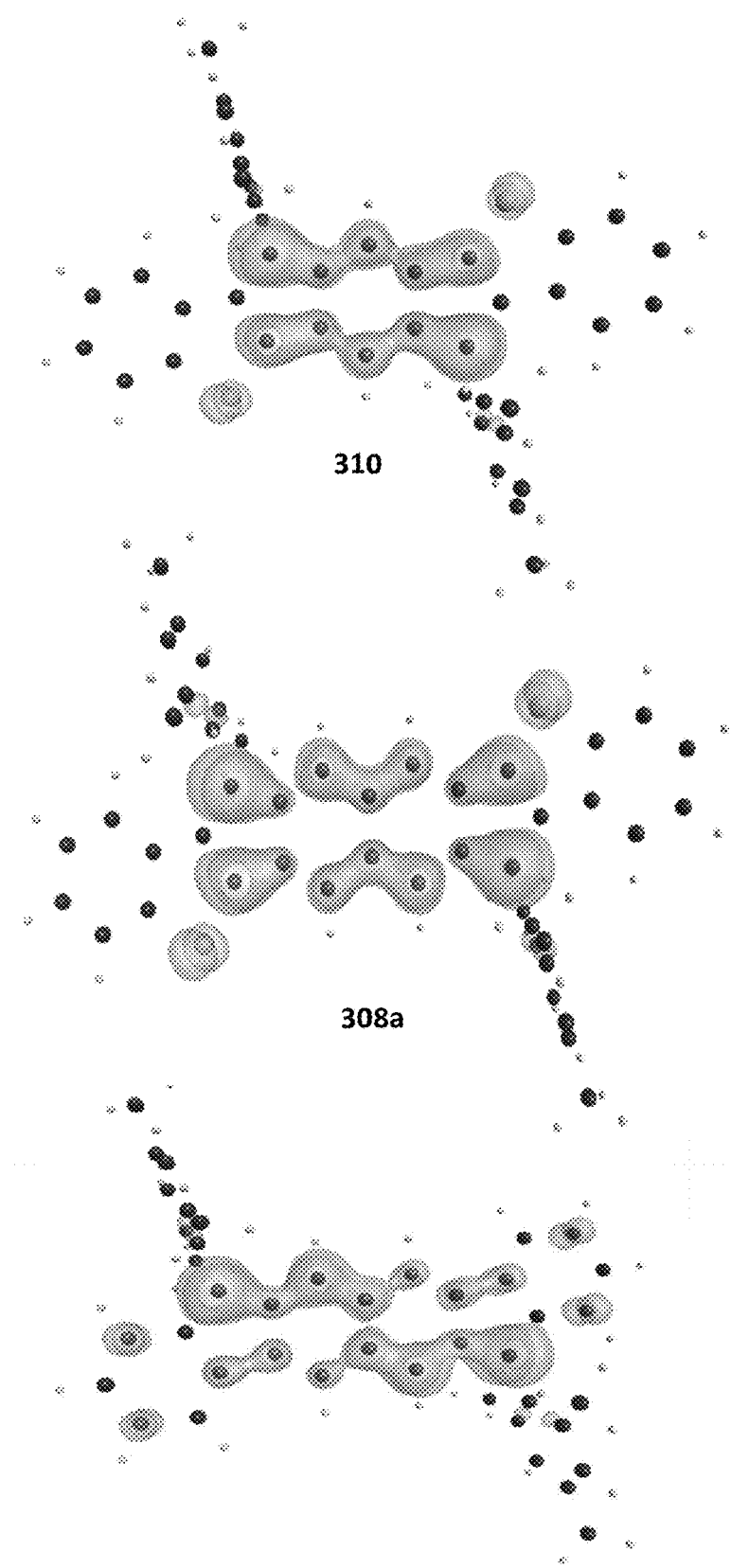
FIG. 26 illustrates odd-electron density maps for 7,14-dimesitylfluoreno[3,2-b]fluorene and compounds 308a and 310 calculated at the LC-UBLYP/6-311G(d) level of approximation, wherein the grey shading represents the isosurface of odd-electron density with the contour value of 0.001 a.u.

To further confirm rearomatization of the central core, nucleus independent chemical shift (NICS(1)) calculations on 7,14-dimesitylfluoreno[3,2-b]fluorene, indacenedi(benzothiophene), and compound 308a were performed at the U(R) B3LYP/6-311G(d) level and are shown in FIG. 25. As previously disclosed, the central core of compound 310 exhibits strong anti-aromatic character (7.24), while the aromaticity of the central unit is modestly recovered in compound 308 (−1.30) when the core is elongated from benzene to naphthalene; a similar result is obtained in 7,14-dimesitylfluoreno[3,2-b]fluorene (−1.59). This tendency shows a good correlation with the results for diradical character and spectroscopic properties. In addition, aromaticity in the terminal benzene rings in compound 310 (−9.89) and compound 308a (−10.1) is larger than in 7,14-dimesitylfluoreno[3,2-b]fluorene (−7.49), and is even comparable to benzene itself (−10.1), whereas the anti-aromaticity of five-membered carbocycles is more intensified in compound 310 (12.1) and compound 308a (2.96) than in 7,14-dimesitylfluoreno[3,2-b]fluorene (0.32). These features suggest that the aromatization effect by the terminal benzene rings on the five-membered carbocycles in 7,14-dimesitylfluoreno[3,2-b]fluorene is significantly reduced in compound 310 and compound 308a by inserting fused benzothiophenes, in agreement with the rupture of aromaticity on the thiophenes (FIG. 7) and with the role of the sulfur atoms as electron donors towards the radical centers. This latter point is nicely represented by the odd-electron density distribution, which indicates the spatial contribution of unpaired electrons to the diradical character (FIG. 26).

Example 21

Cyclic voltammetry (CV) for the two compounds was carried out in a three compartment electrochemical cell in CH$_2$Cl$_2$ with 0.1 M TBAPF$_6$ using a Pt wire as working electrode and a Pt gauze as counter-electrode and a Ag wire as pseudo-reference electrode and the data tested versus the Fc/Fc$^+$ couple. The temperature was kept at 298 K. The exact concentrations of the samples are unknown (approx. 10$^{-4}$ M).

Figure 27A:
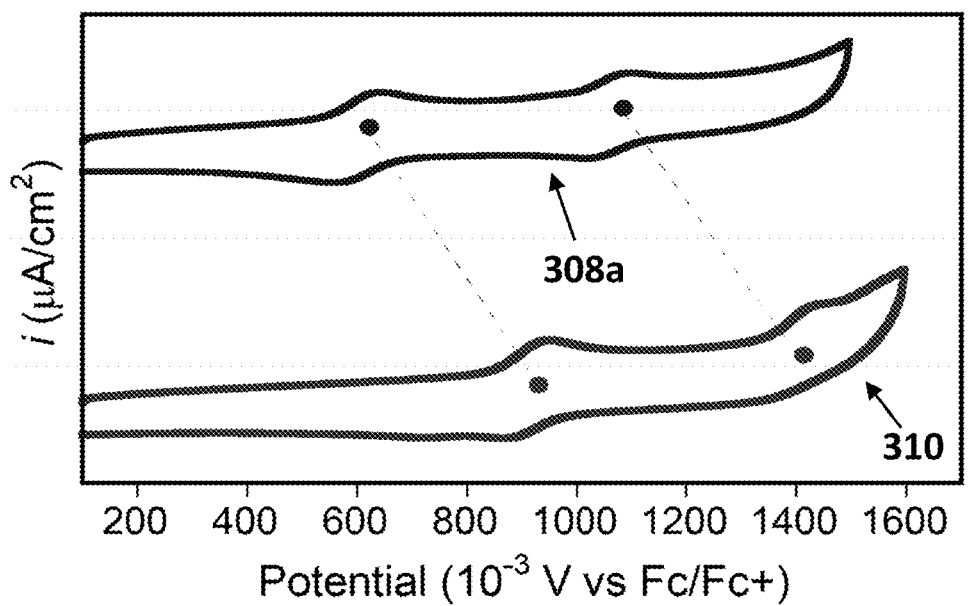
FIGS. 27A and 27B are partial (FIG. 27A) and full (FIG. 27B) cyclic voltammograms of compounds 308a and 310.
Figure 27B:
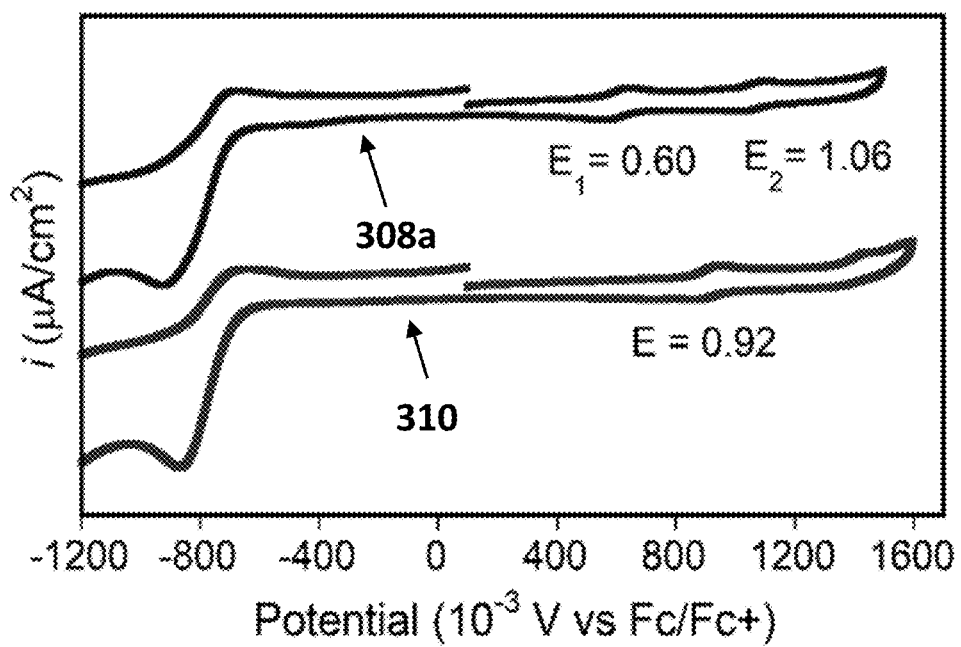

The cyclic voltammetry of compound 308b in FIGS. 27A and 27B shows the electrochemical discharge and the reversible formation of the cation and dication species at lower oxidation potentials than those measured for 310, in line with the increased π-conjugation. Conversely, the formation of anionic species is destabilized owing to the presence of thiophenes, in accordance with the electron repulsion environment around the sulfur atoms.

In view of the many possible embodiments to which the principles of the present disclosure may be applied, it should be recognized that the illustrated embodiments are only preferred examples and should not be taken as limiting the scope of the present disclosure. Rather, the scope is defined by the following claims. We therefore claim as our invention all that comes within the scope and spirit of these claims.

We claim:
1. A compound having a structure satisfying Formula I or II,

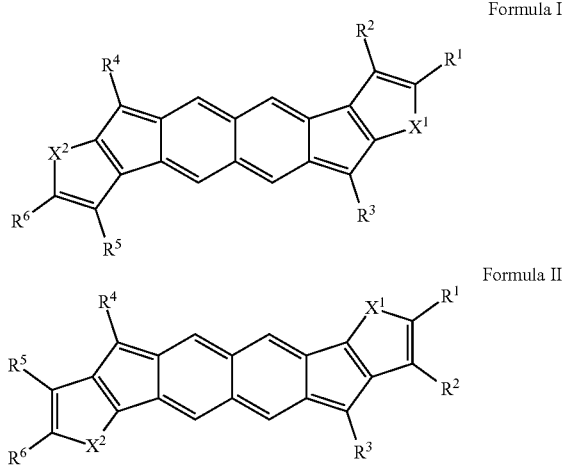

wherein
- each of X$^1$ and X$^2$ independently are selected from S, or oxidized forms thereof; O; or NR, wherein each R independently is selected from hydrogen, aliphatic, heteroaliphatic, haloaliphatic, haloheteroaliphatic, aromatic, or an organic functional group;
- each of R$^3$ and R$^4$ independently is selected from aliphatic, aromatic, heteroaliphatic, or an organic functional group;

each of $R^1$, $R^2$, $R^5$, and $R^6$ independently is selected from hydrogen, aliphatic, aromatic, heteroaliphatic, or an organic functional group; or $R^1$ and $R^2$ together, and/or $R^5$ and $R^6$ together, provide an aromatic ring.

2. The compound of claim 1, wherein each of $X^1$ and $X^2$ independently are S or $SO_2$.

3. The compound of claim 1, wherein each of $X^1$ and $X^2$ are S.

4. The compound of claim 1, wherein each of $R^3$ and $R^4$ independently are aromatic or an organic functional group.

5. The compound of claim 1, wherein each of $R^3$ and $R^4$ independently are aromatic, wherein the aromatic group comprises one or more substituents other than hydrogen.

6. The compound of claim 5, wherein the one or more substituents other than hydrogen are aliphatic, aromatic, heteroaliphatic, or an organic functional group.

7. The compound of claim 4, wherein each organic functional group independently is selected from a combination of an aliphatic, heteroaliphatic, aromatic, haloaliphatic, and/or haloheteroaliphatic group; or aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

8. The compound of claim 1, wherein each of $R^3$ and $R^4$ independently are selected from alkyl; alkynyl; alkenyl; heteroalkyl; heteroalkynyl; heteroalkenyl; phenyl; naphthyl; pyridinyl; or an organic functional group selected from benzyl, amino, halogen, nitro, alkoxy, aroxy, cyano, thiol, thioether, or hydroxyl.

9. The compound of claim 1, where $R^3$ and $R^4$ are 2,4,6-$Me_3C_6H_2$, 2,4,6-$iPr_3C_6H_2$, or 4-$t$-Bu-2,6-$Me_2CH_6H_2$.

10. The compound of claim 1, wherein each of $R^1$, $R^2$, $R^5$, and $R^6$ independently is selected from H, amino, alkyl, alkynyl, alkenyl, heteroalkyl, heteroalkynyl, heteroalkenyl, an organic functional group; or $R^1$ and $R^2$ together provide an aryl or heteroaryl ring and/or $R^5$ and $R^6$ together provide an aryl or heteroaryl ring.

11. The compound of claim 1, wherein $R^1$ and $R^2$ together provide a phenyl group, a naphthyl group, an anthracenyl group, a tetracenyl group, a pentacenyl group, a phenanthrenyl group, a chrysenyl group, a pyrenyl group, or other aromatic ring system.

12. The compound of claim 1, wherein $R^5$ and $R^6$ together provide a phenyl group, a naphthyl group, an anthracenyl group, a tetracenyl group, a pentacenyl group, a phenanthrenyl group, a chrysenyl group, a pyrenyl group, or other aromatic ring system.

13. The compound of claim 1, wherein when any one or more of $R^1$, $R^2$, $R^3$, $R^4$, $R^5$, or $R^6$ are aromatic groups, the aromatic group comprises one or more substituents other than hydrogen.

14. The compound of claim 13, wherein one or more substituents other than hydrogen are selected from aliphatic groups, heteroaliphatic groups, aromatic groups, or an organic functional group.

15. The compound of claim 1, wherein the compound has a structure satisfying one or more of Formulas III or IV

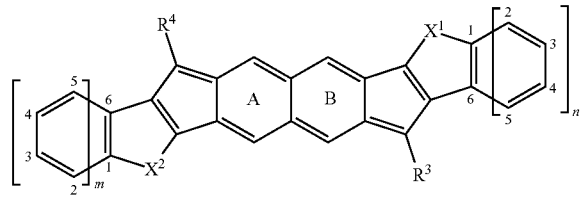

Formula III

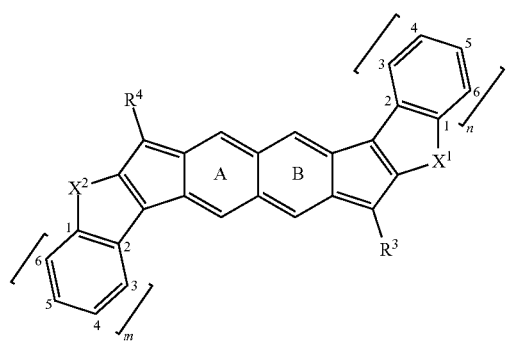

Formula IV wherein n and m independently are an integer ranging from 1 to 5.

16. The compound of claim 1, wherein the compound has a structure satisfying one or more of Formula IIIA or Formula IVA

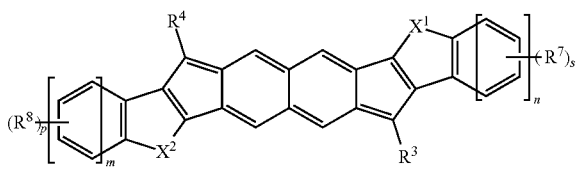

Formula IIIA

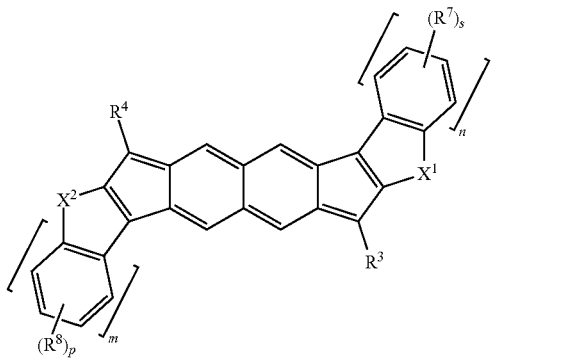

Formula IVA wherein
$R^7$ and $R^8$ independently are selected from an aliphatic group, a heteroaliphatic group, an aromatic group, a haloaliphatic group, or an organic functional group;
p and s independently are an integer ranging from 1 to 12
n and m independently are an integer ranging from 1 to 5.

17. The compound of claim 16, wherein each organic functional group independently is selected from a combination of an aliphatic, heteroaliphatic, aromatic, haloaliphatic, and/or haloheteroaliphatic group; or aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

18. The compound of claim 1, wherein the compound is selected from

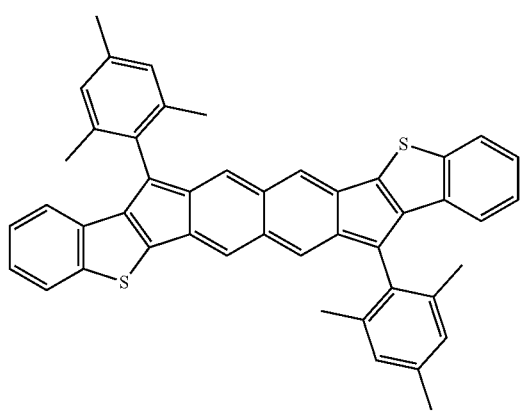

;

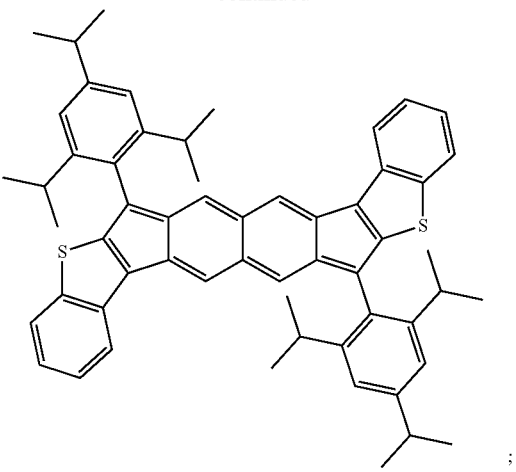

;

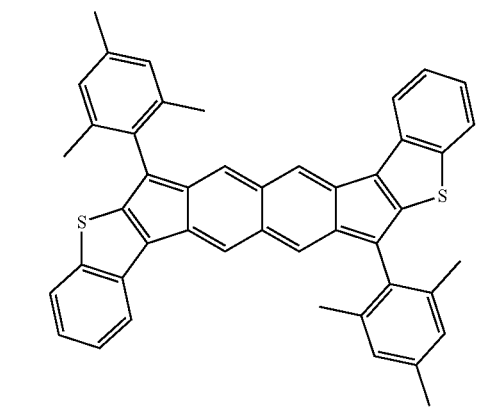

;

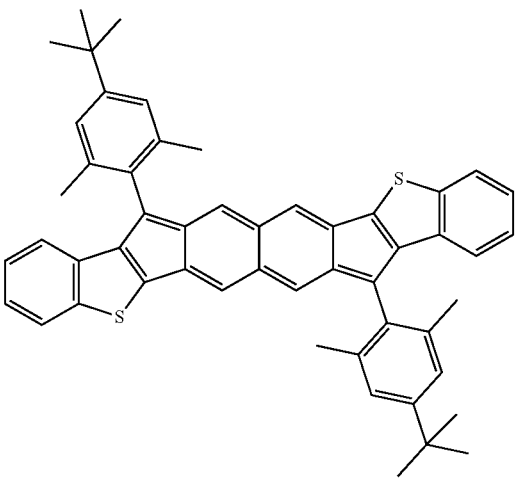

;

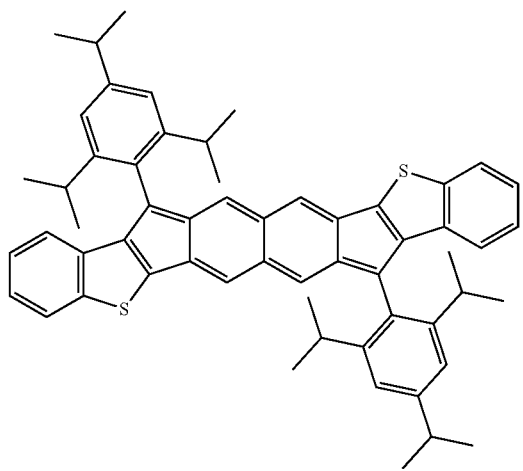

;

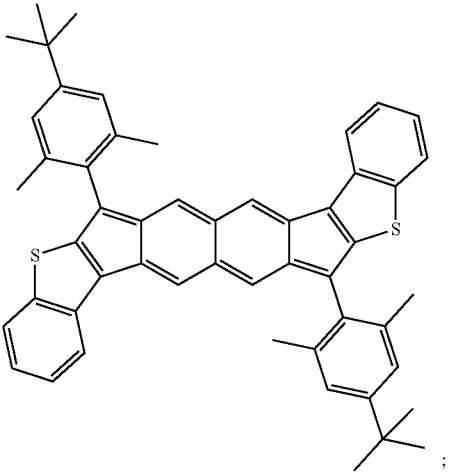

;

83
-continued
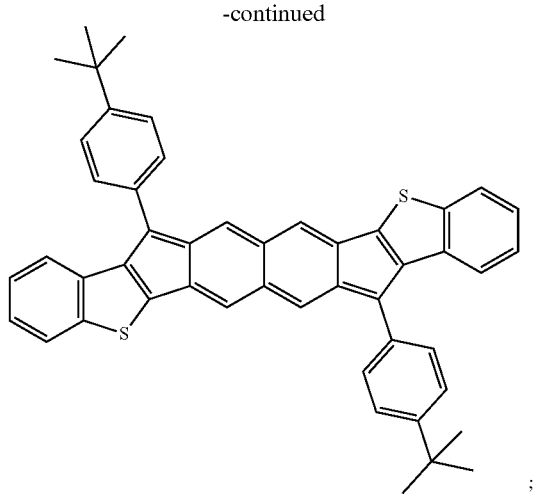
;
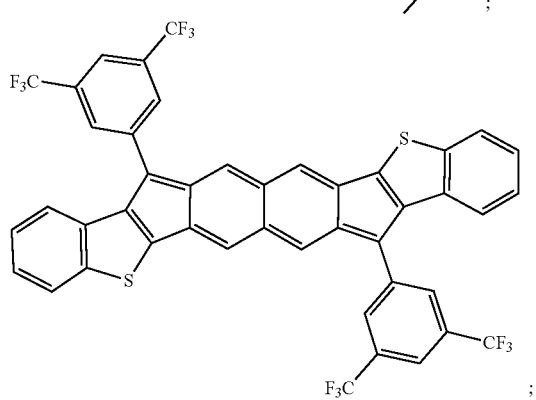
;
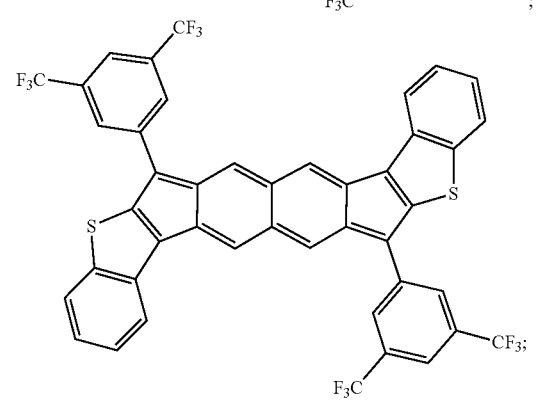
;
84
-continued
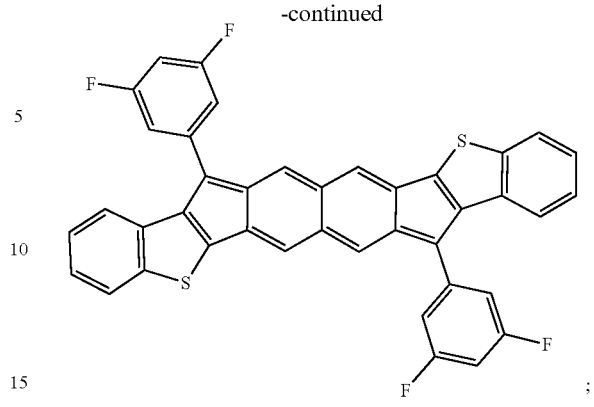
;
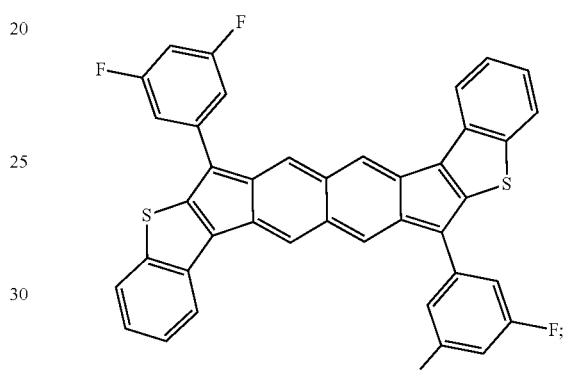
;
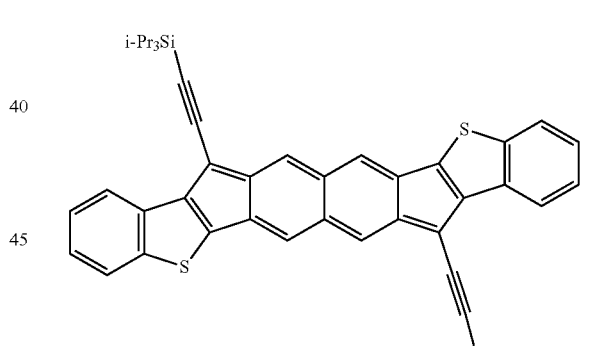
;
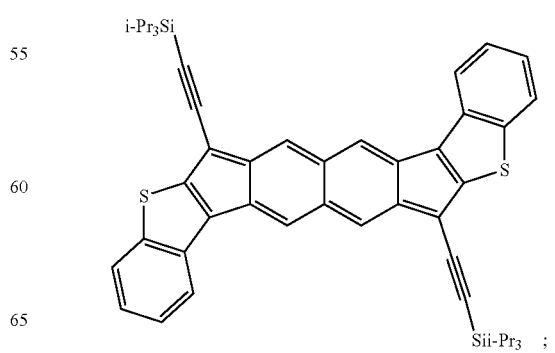
;

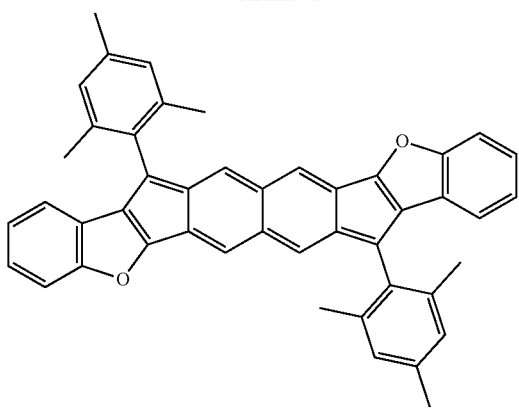
;
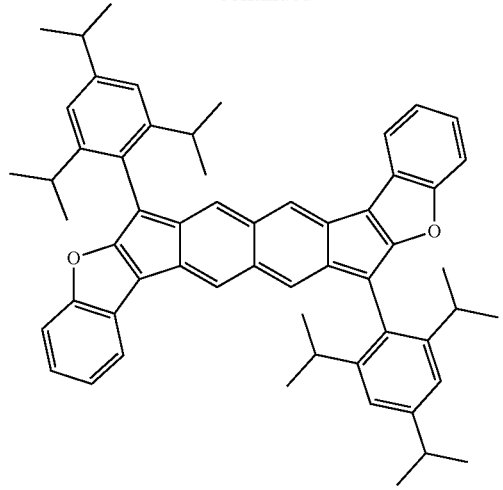
;
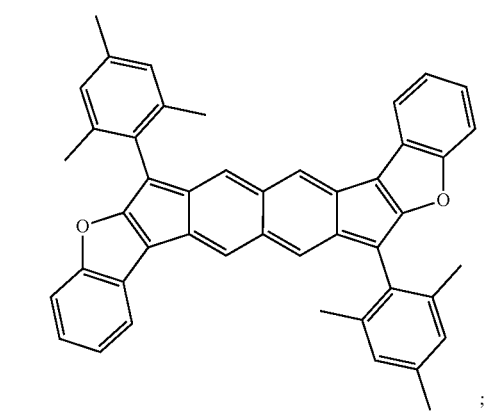
;
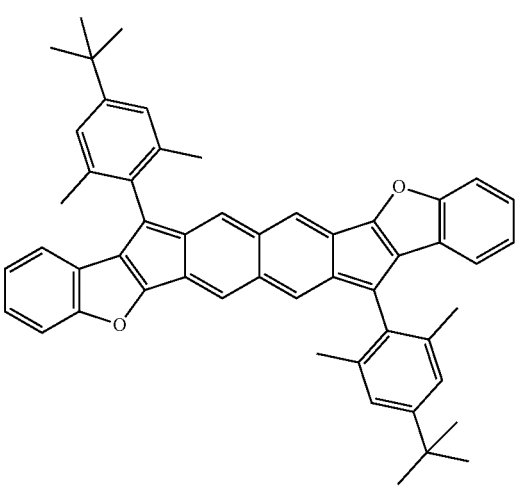
;
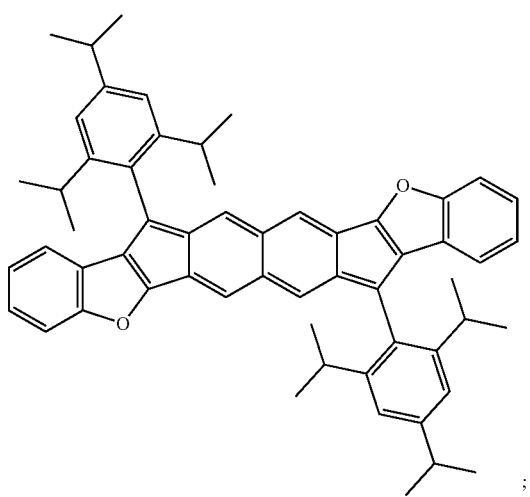
;
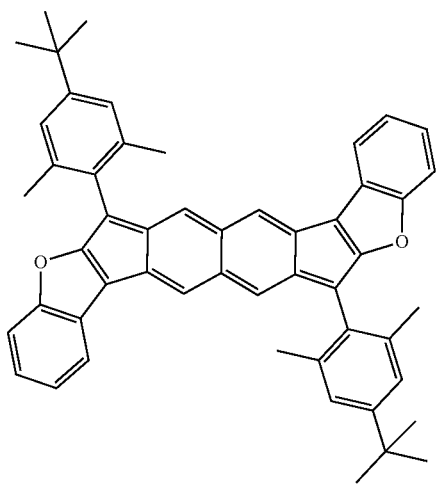
;

87
-continued
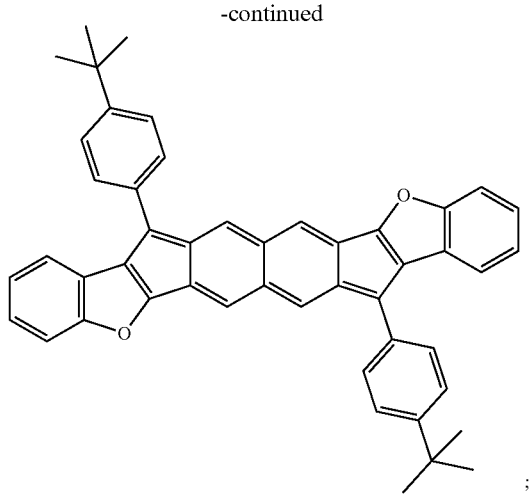
;
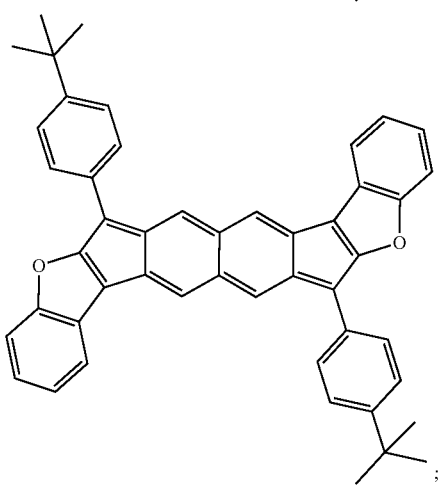
;
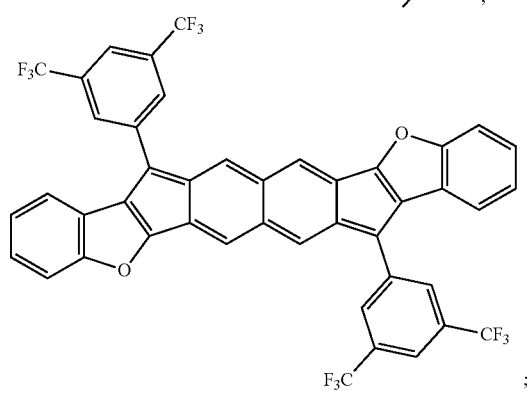
;
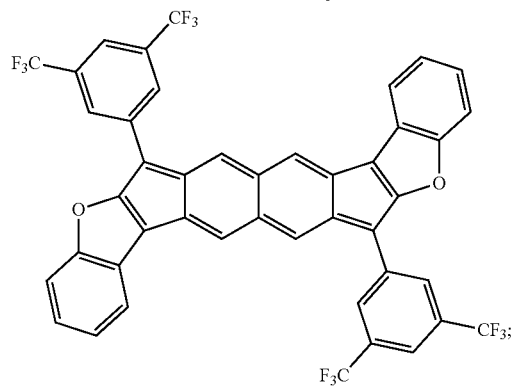
;
88
-continued
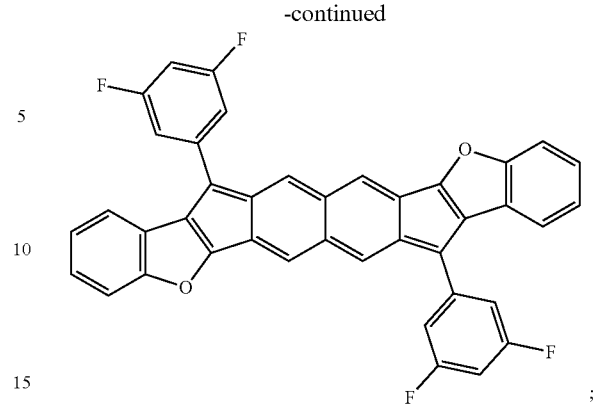
;
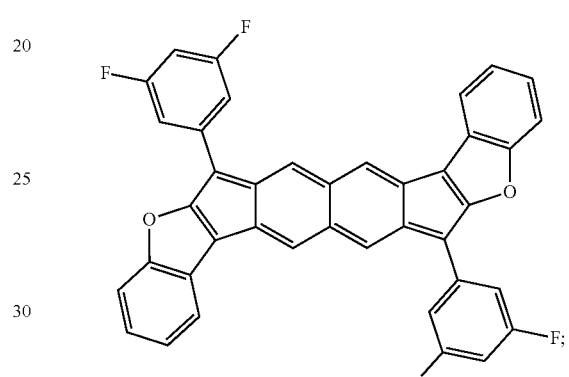
;
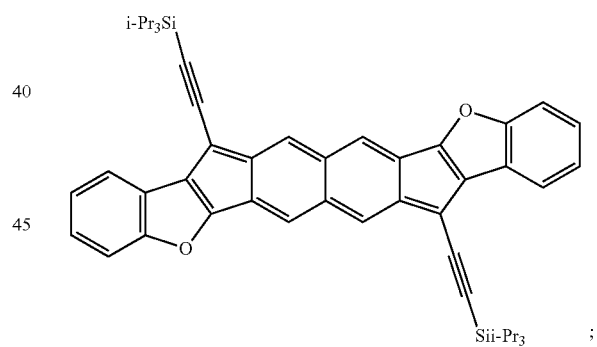
;
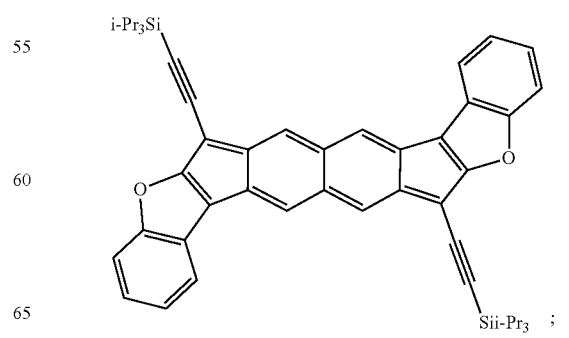
;

89
-continued
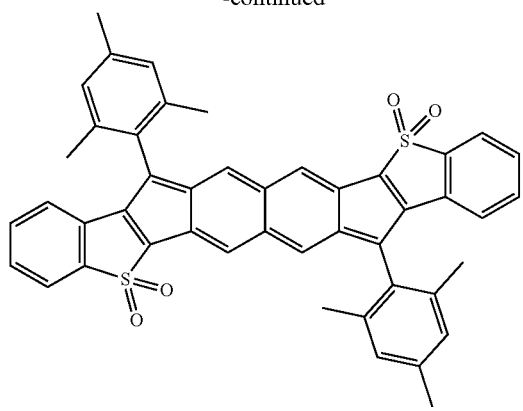
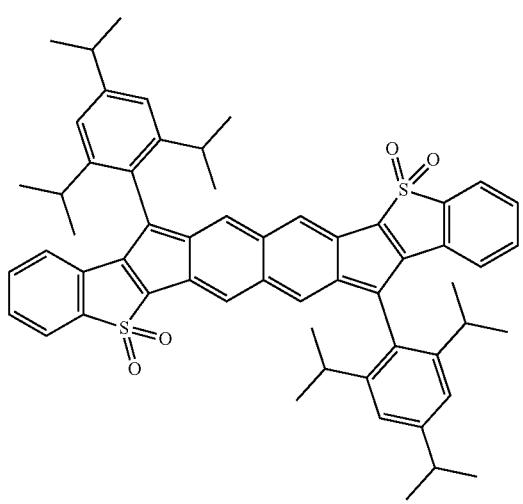
90
-continued
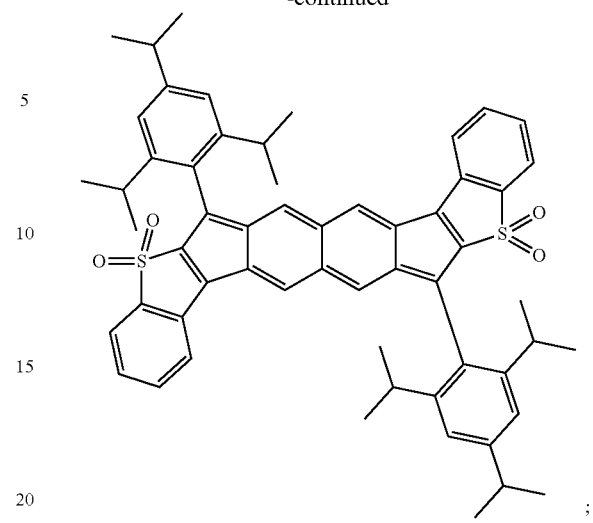
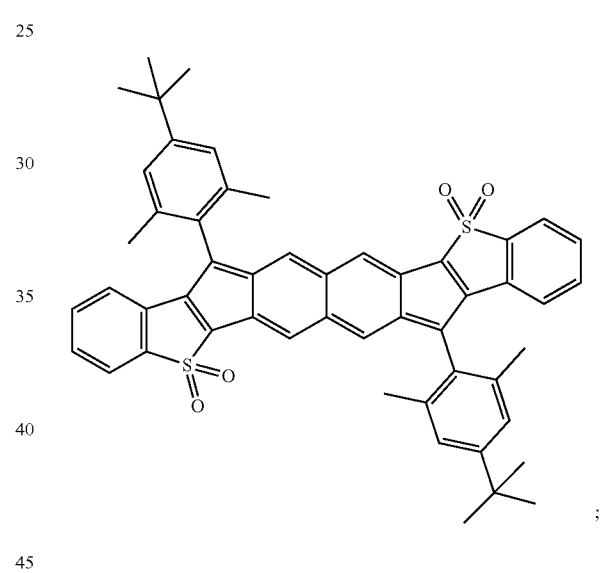
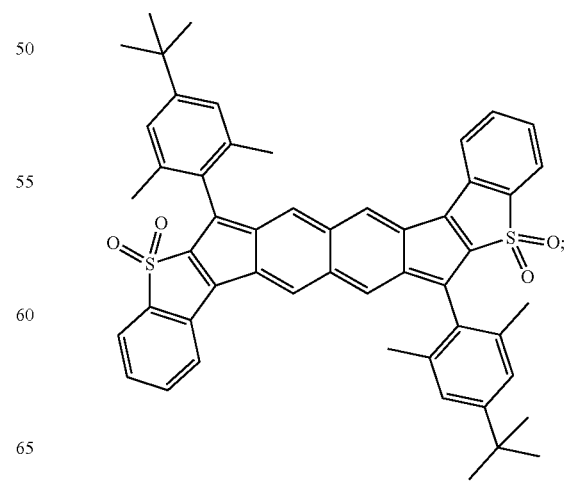

91
-continued
92
-continued
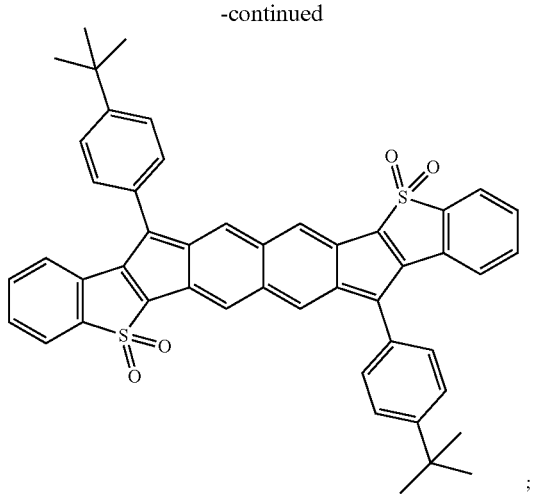
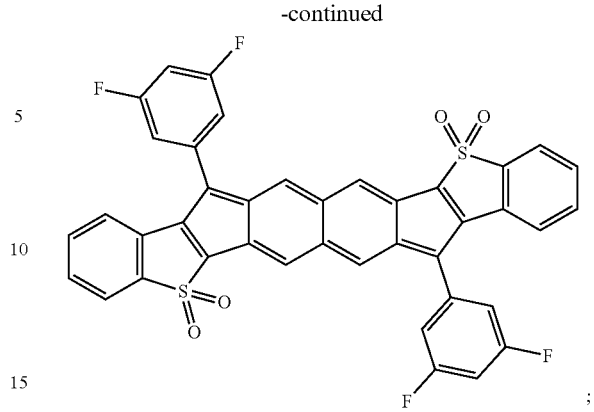
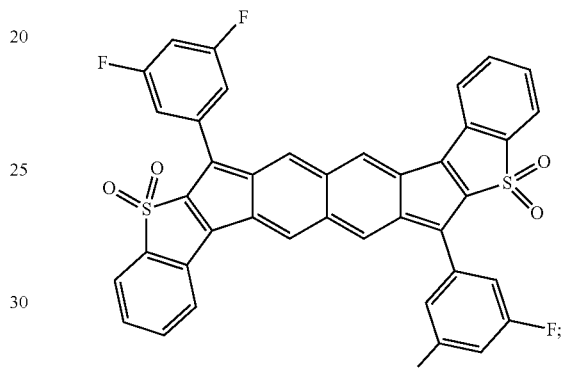
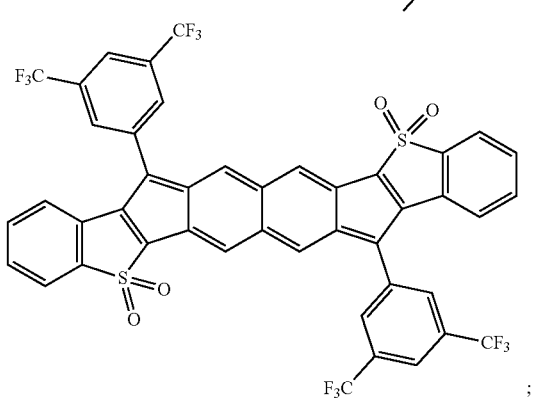
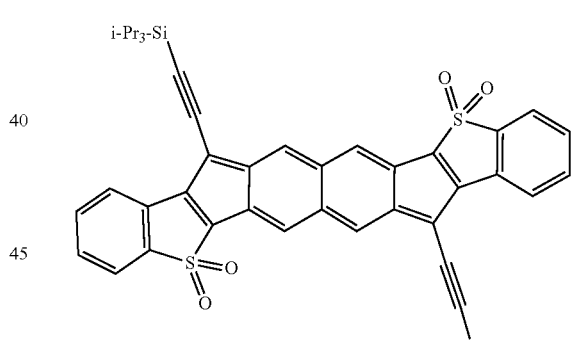
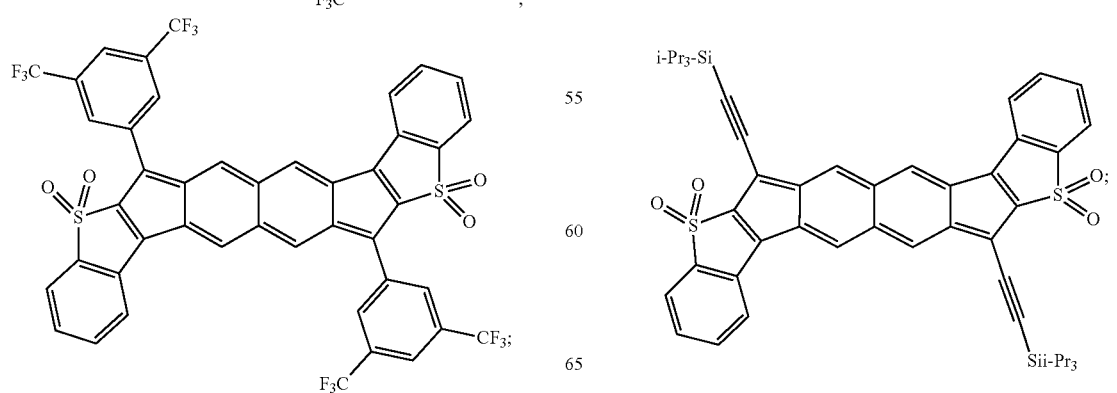

93
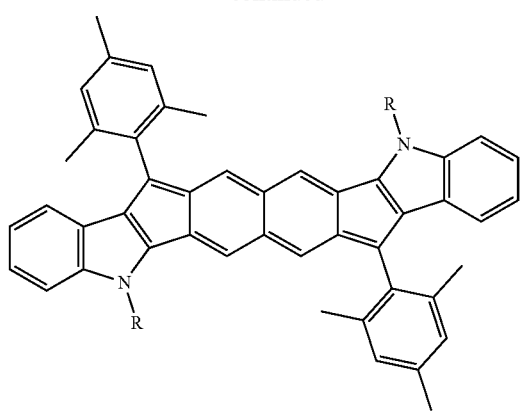
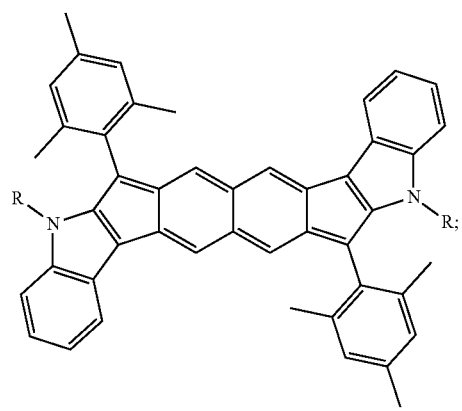
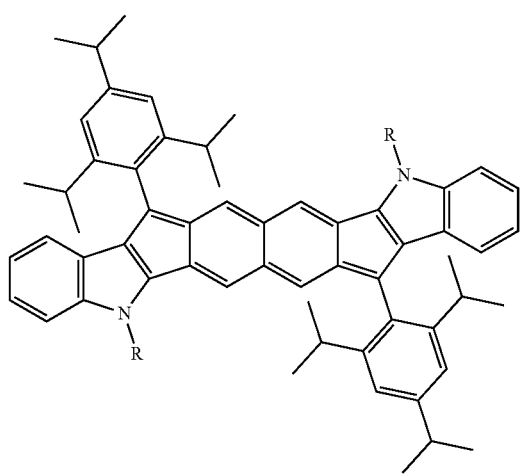
94
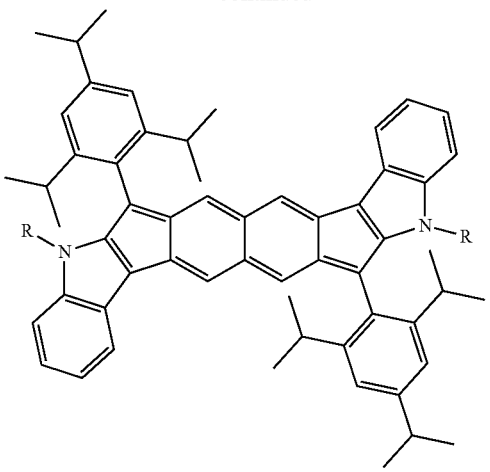
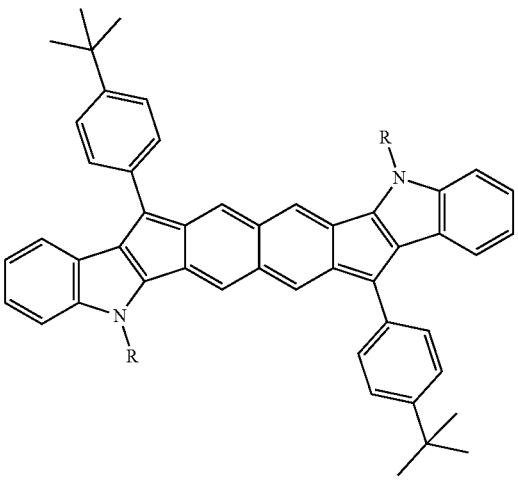
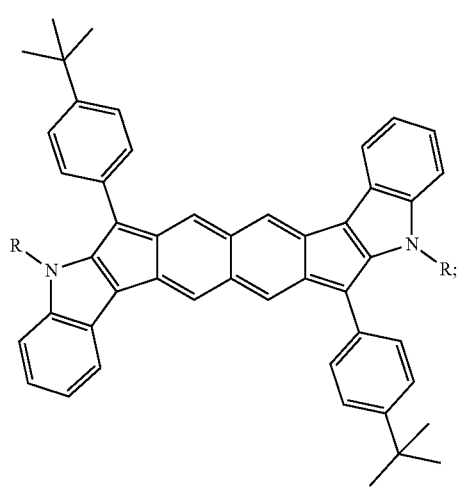

95
-continued
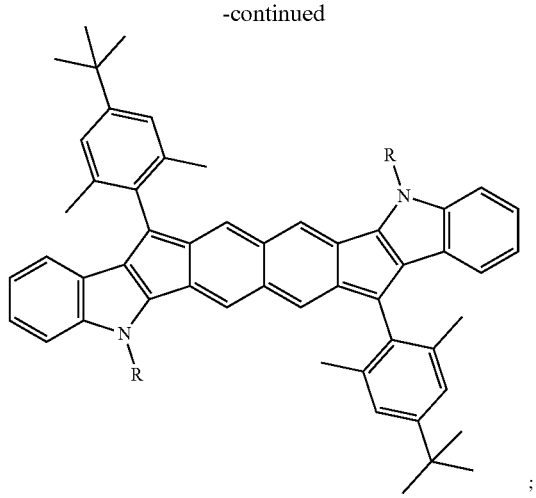
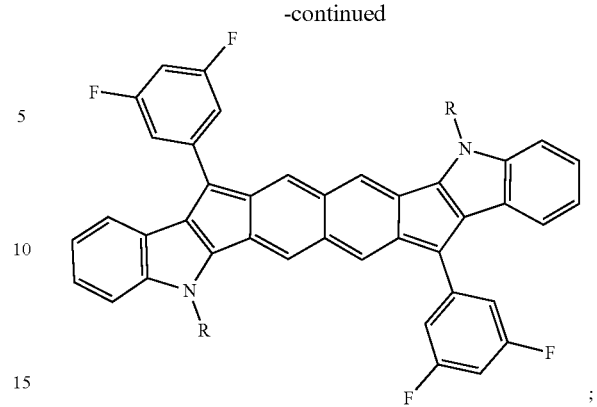
96
-continued
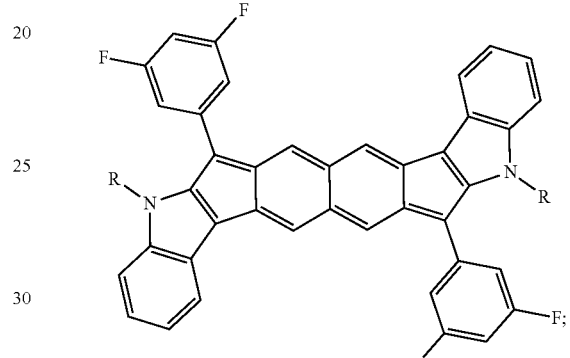
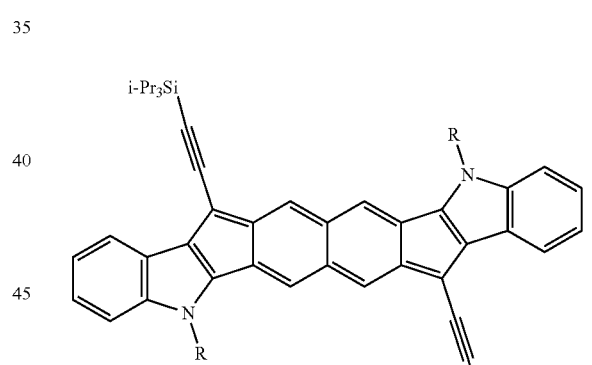
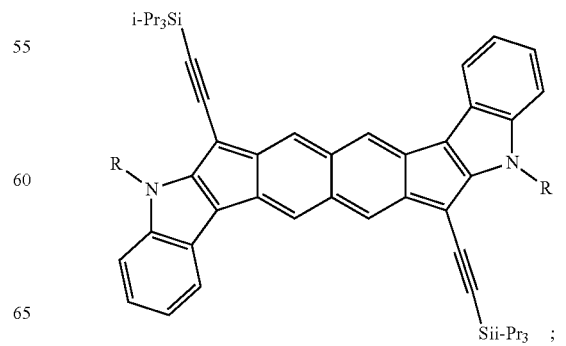

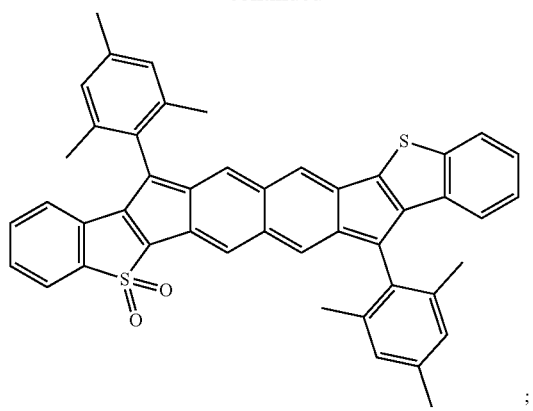
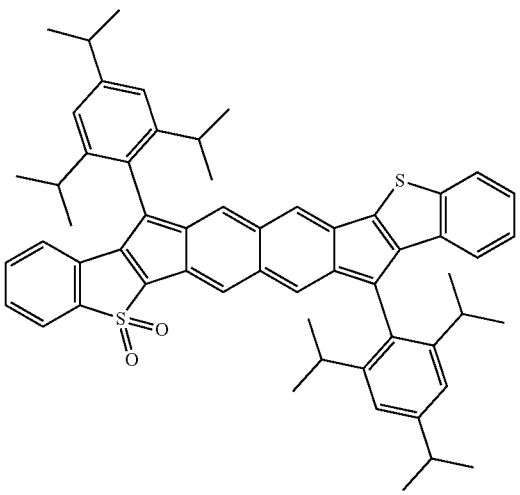
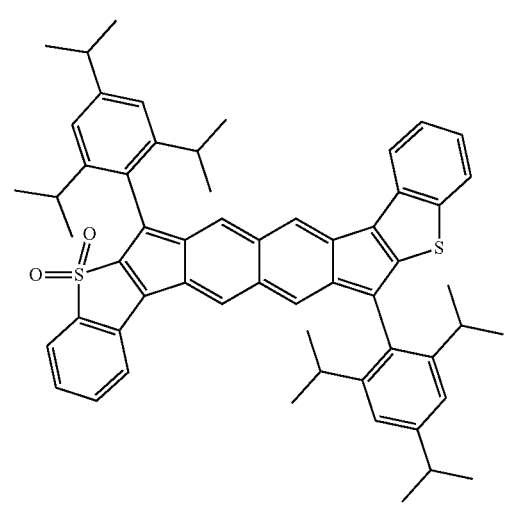
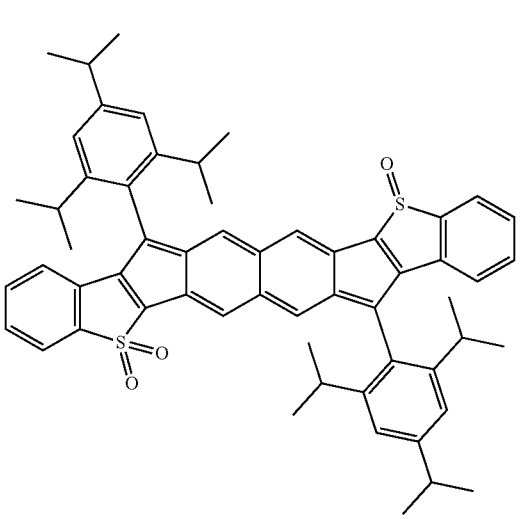

99
-continued
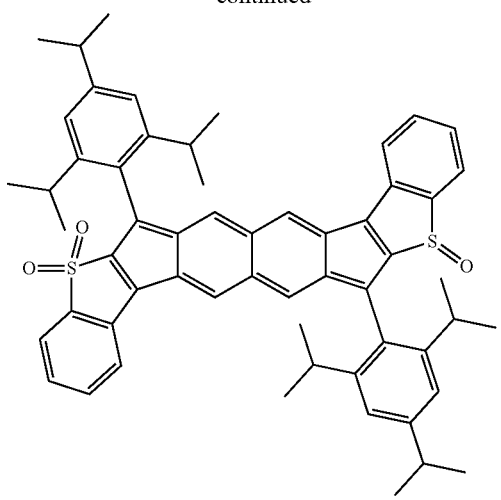
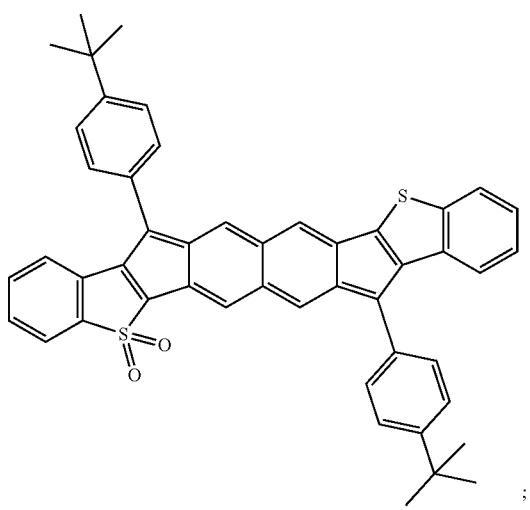
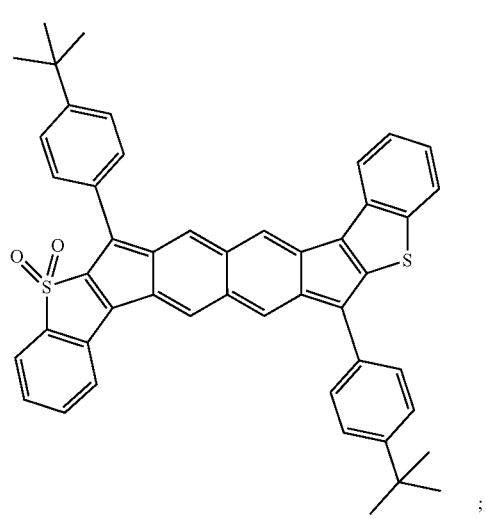
100
-continued
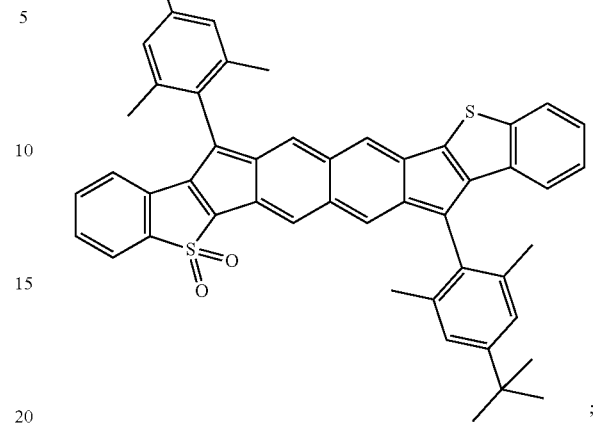
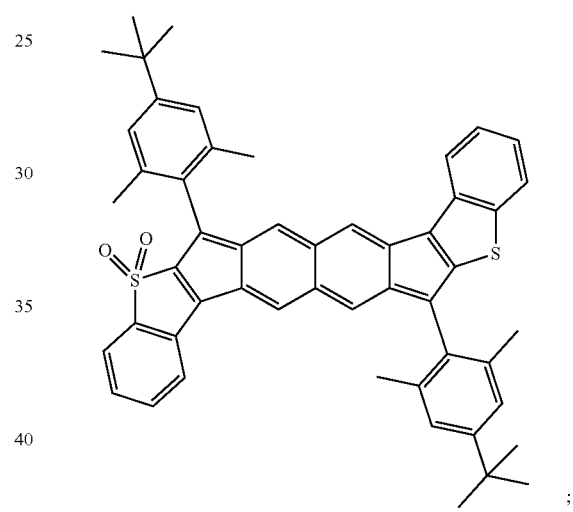
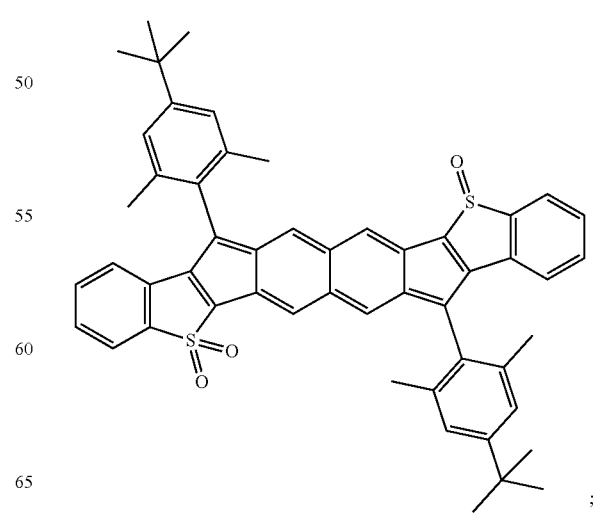

101
-continued
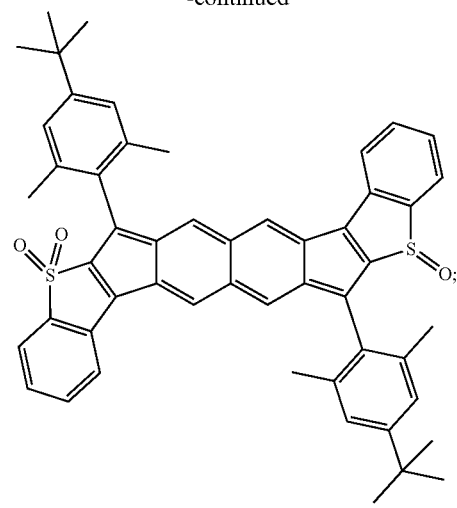
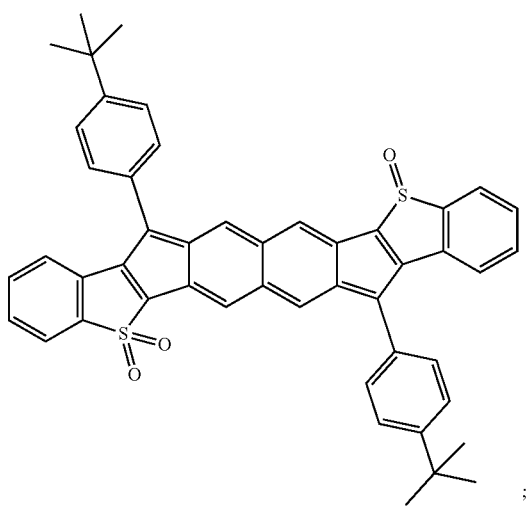
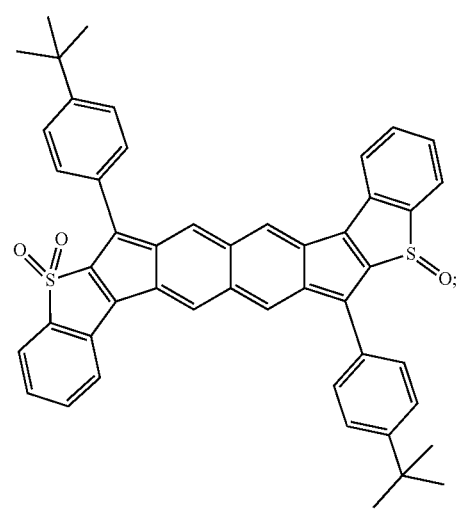
102
-continued
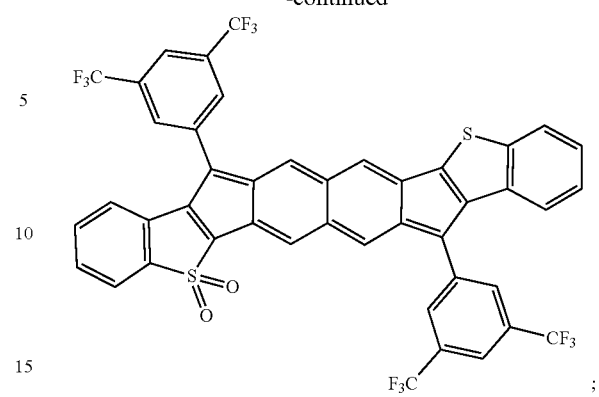
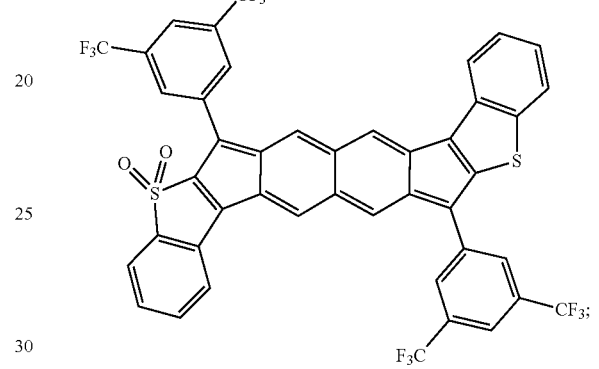
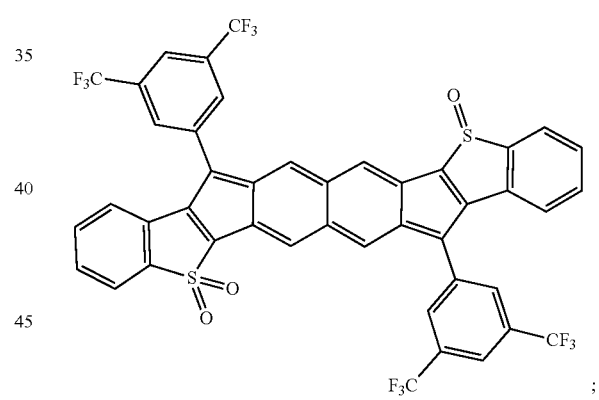
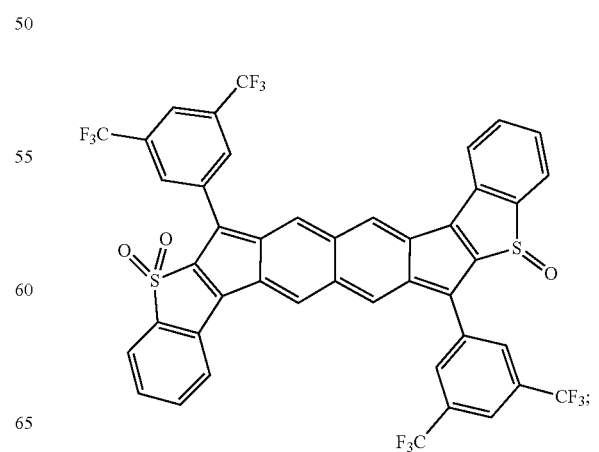

103
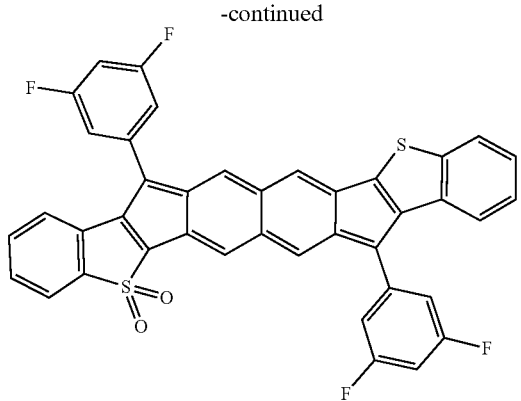
;
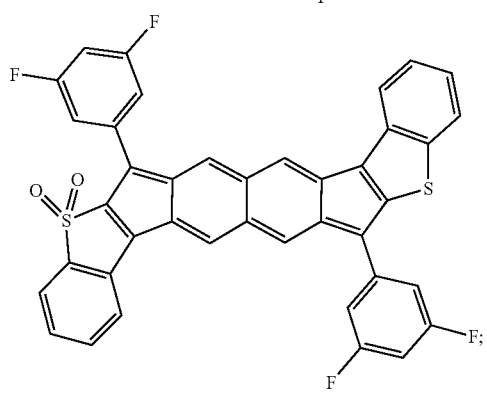
;
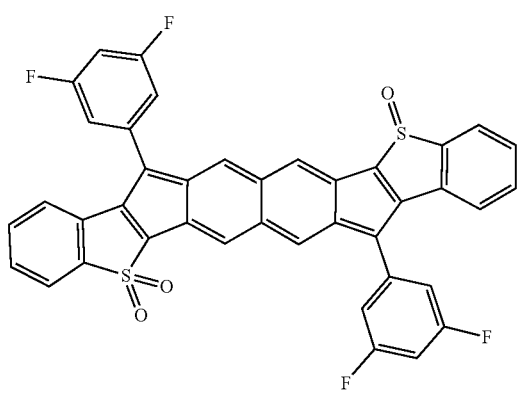
;
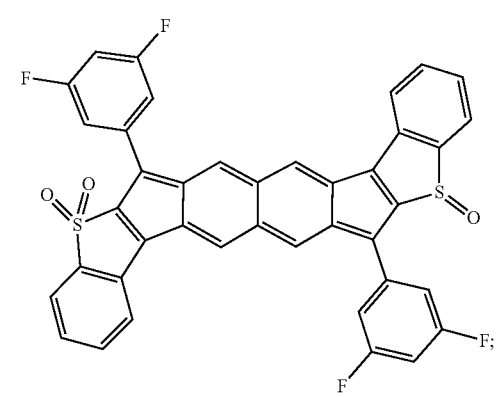
;
104
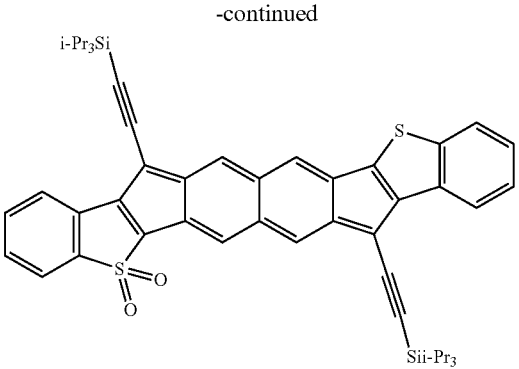
;
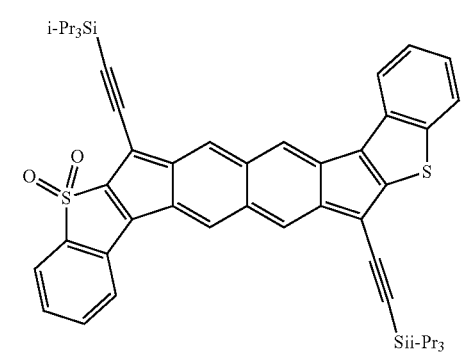
;
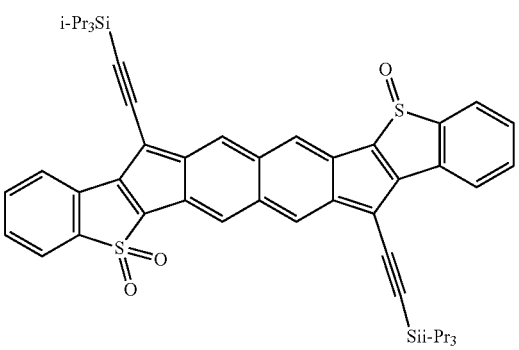
;
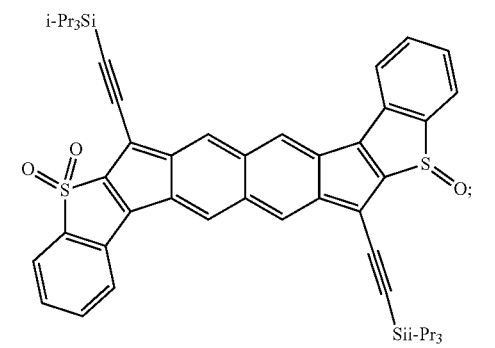

105
-continued
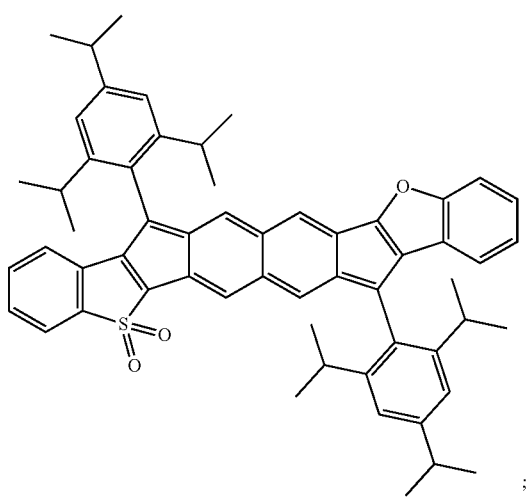
;
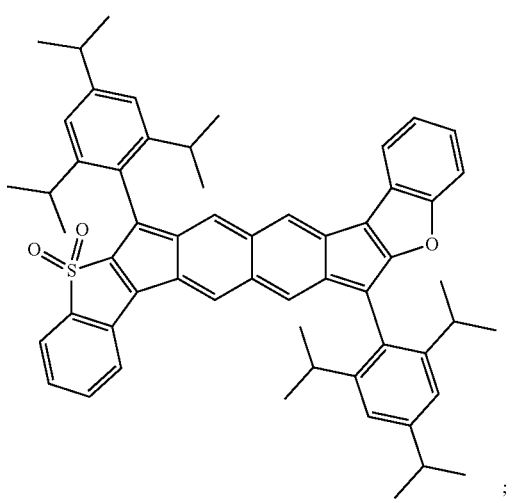
;
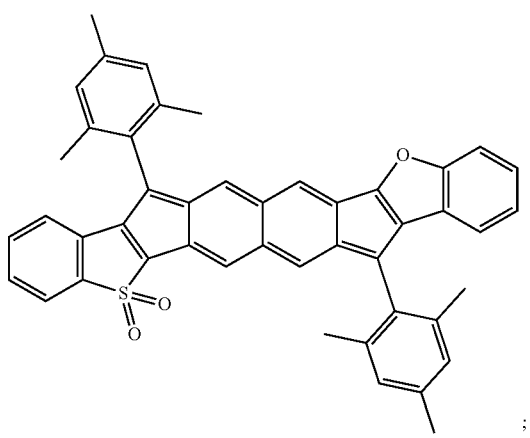
;
106
-continued
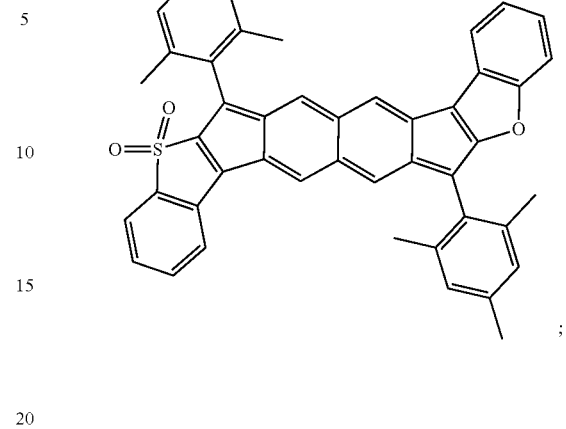
;
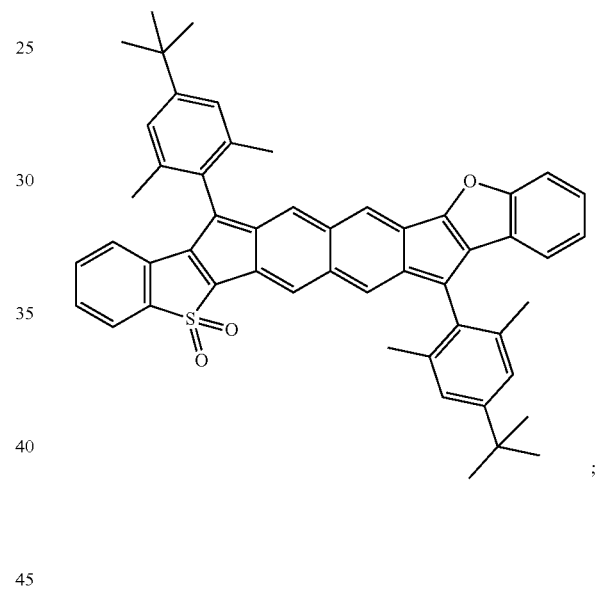
;
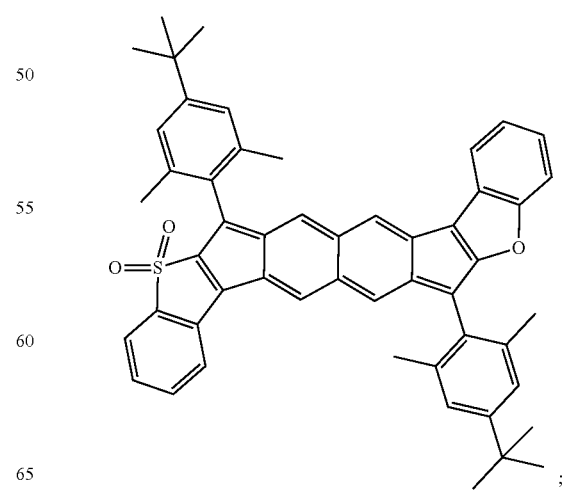
;

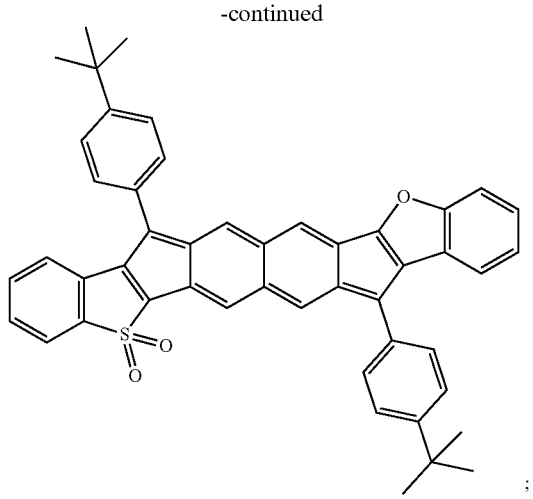
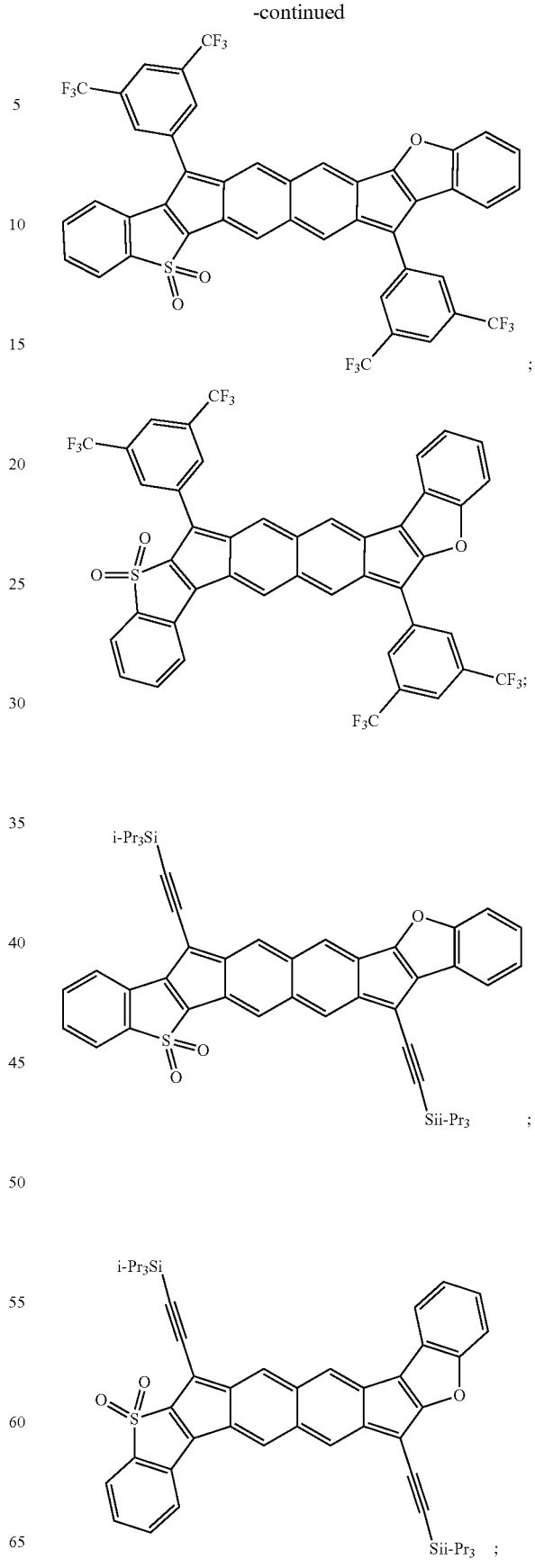

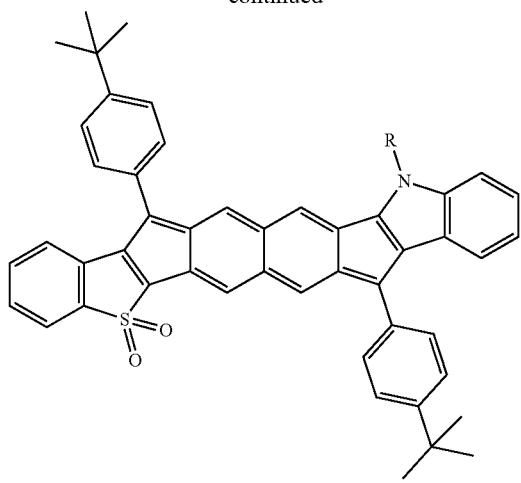
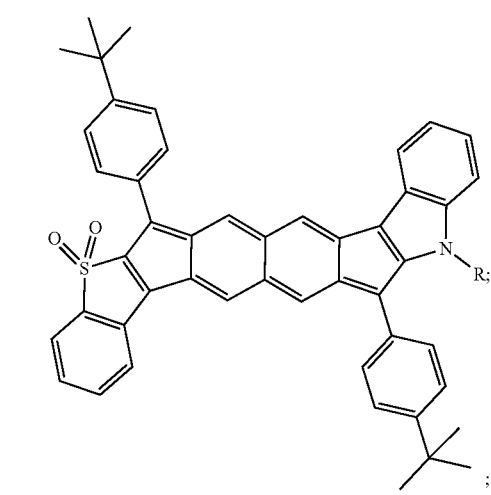
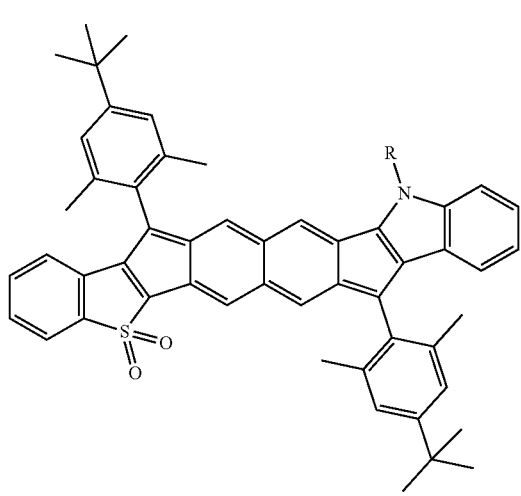
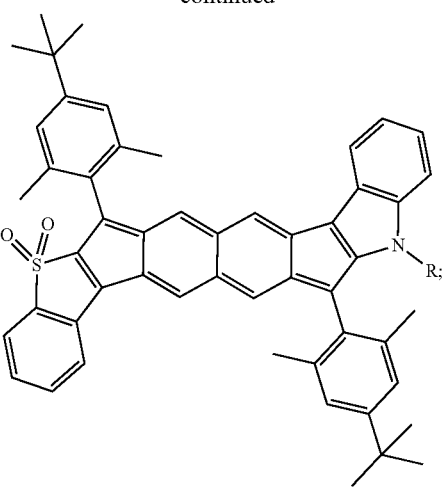
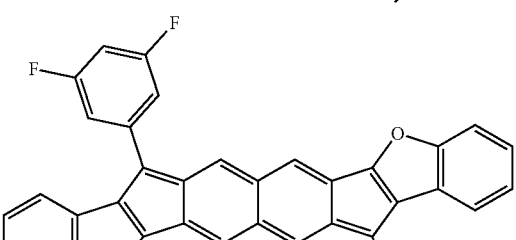
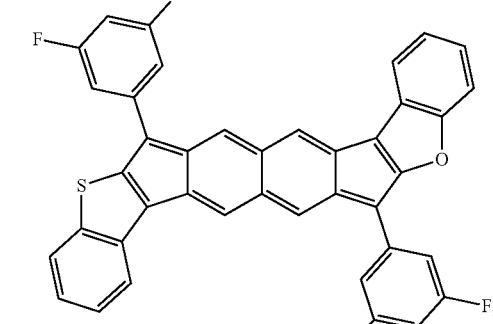
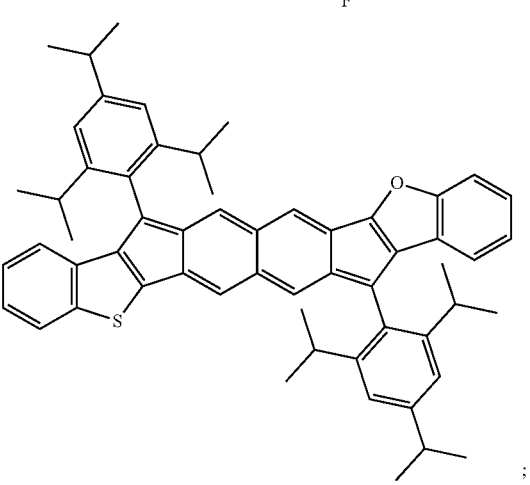

111
-continued
112
-continued
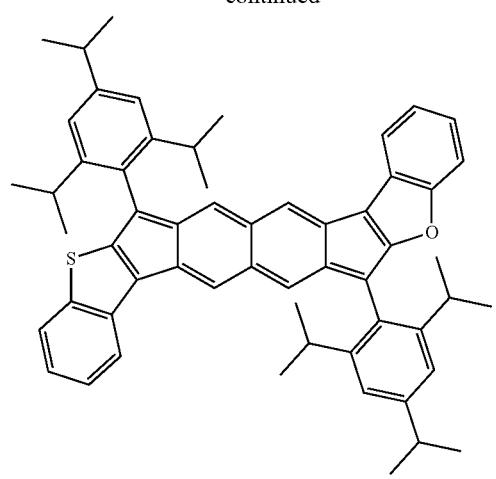
;
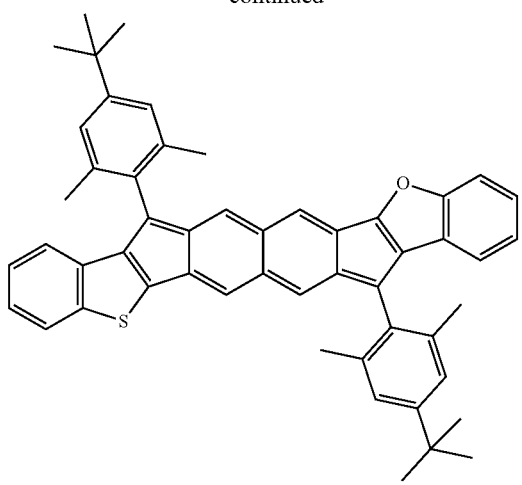
;
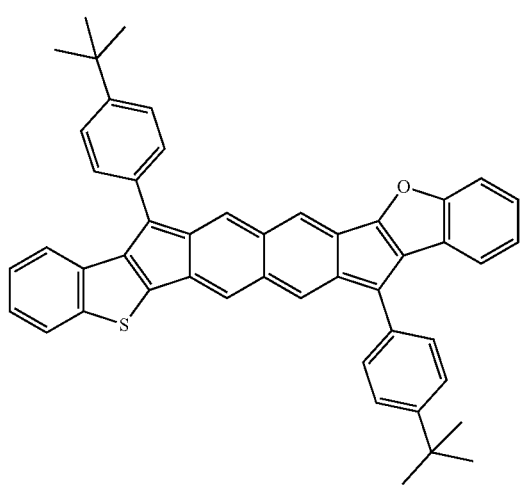
;
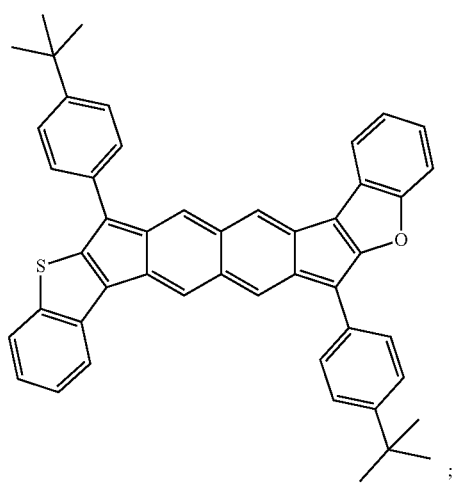
;
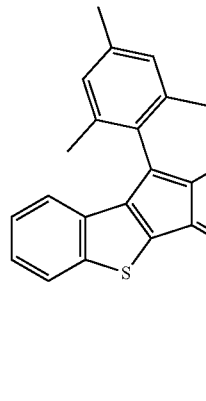
;

113
-continued
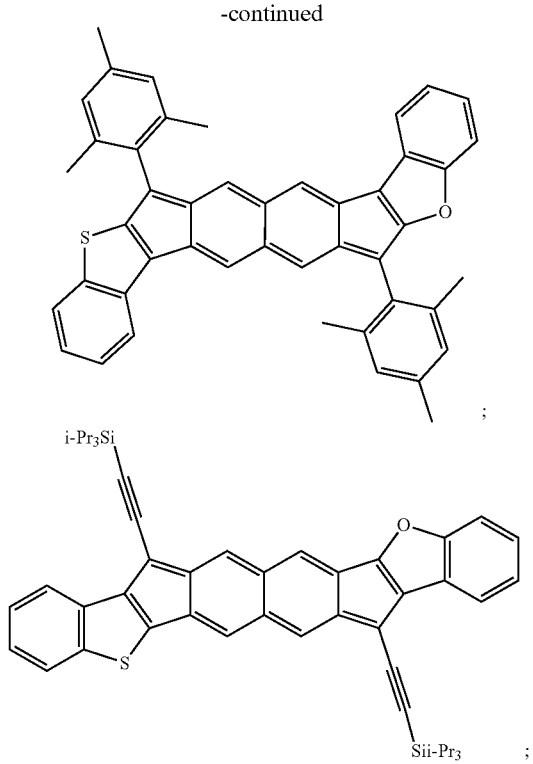
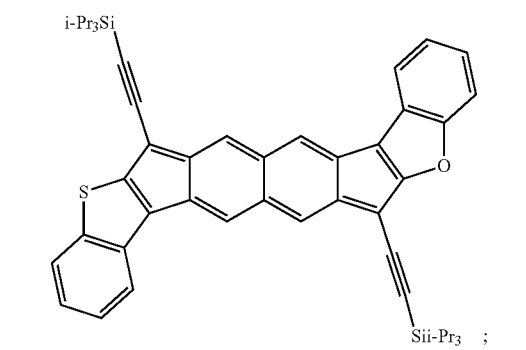
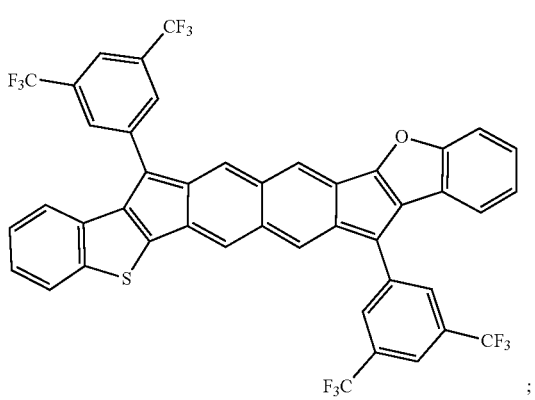
114
-continued
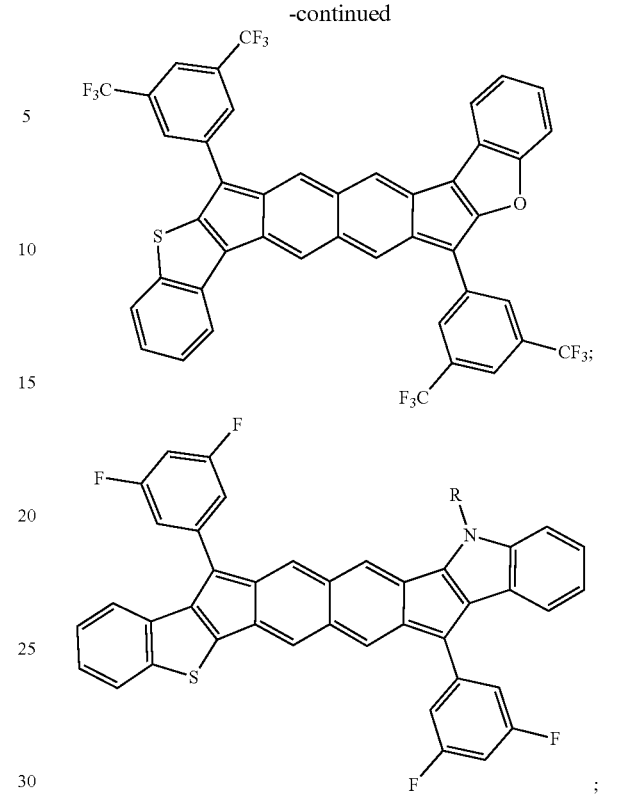
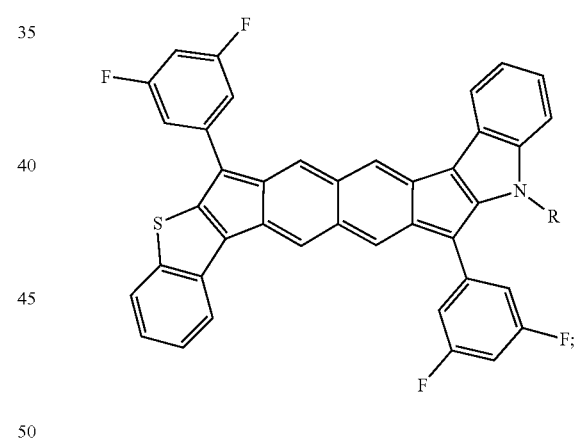
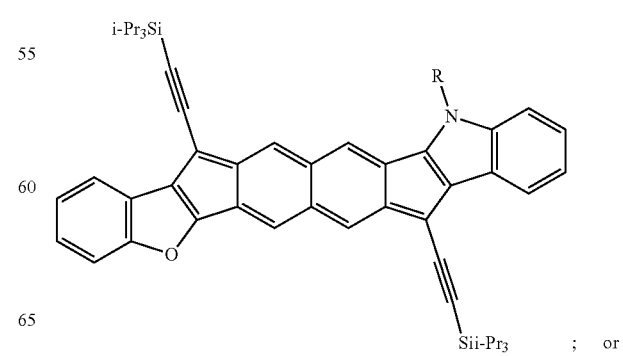
; or -continued
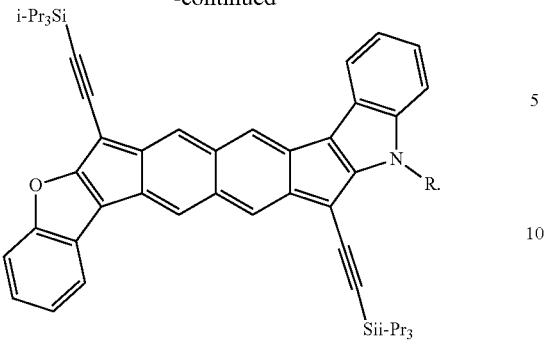
19. An apparatus, comprising an electronic or electrooptical device selected from an organic light-emitting diode (OLED), an organic field-effect transistor (OFET), or an organic photovoltaic cell (OPV) and further comprising a compound of claim 1.
20. A thin film, comprising a compound according to claim 1.
* * * * *